United States Patent
Guillemont et al.

(10) Patent No.: US 8,293,732 B2
(45) Date of Patent: Oct. 23, 2012

(54) ANTIBACTERIAL QUINOLINE DERIVATIVES

(75) Inventors: Jérôme Emile Georges Guillemont, Andé (FR); Ismet Dorange, Nacka (SE); Magali Madeleine Simone Motte, Heudebouville (FR); Koenraad Jozef Lodewijk Marcel Andries, Beerse (BE); Anil Koul, Berchem (BE)

(73) Assignee: Janssen Pharmaceutica N.V., Beerse (BE)

( * ) Notice: Subject to any disclaimer, the term of this patent is extended or adjusted under 35 U.S.C. 154(b) by 267 days.

(21) Appl. No.: 12/516,249

(22) PCT Filed: Dec. 4, 2007

(86) PCT No.: PCT/EP2007/063314
§ 371 (c)(1),
(2), (4) Date: May 26, 2009

(87) PCT Pub. No.: WO2008/068268
PCT Pub. Date: Jun. 12, 2008

(65) Prior Publication Data
US 2010/0029679 A1    Feb. 4, 2010

(30) Foreign Application Priority Data
Dec. 6, 2006 (EP) .................... 06125510

(51) Int. Cl.
| | | |
|---|---|---|
| A61K 31/496 | (2006.01) | |
| A61K 31/47 | (2006.01) | |
| A61K 31/4725 | (2006.01) | |
| A61K 31/4745 | (2006.01) | |
| A61K 31/5377 | (2006.01) | |
| A61K 31/541 | (2006.01) | |
| C07D 215/227 | (2006.01) | |
| C07D 401/06 | (2006.01) | |
| C07D 405/06 | (2006.01) | |
| C07D 487/04 | (2006.01) | |

(52) U.S. Cl. ............. 514/228.2; 514/235.2; 514/253.07; 514/311; 514/312; 514/314; 544/62; 544/128; 544/238; 544/333; 544/405; 544/363; 546/153; 546/176; 546/177; 546/84

(58) Field of Classification Search .................. None
See application file for complete search history.

(56) References Cited

U.S. PATENT DOCUMENTS
5,965,572 A    10/1999    Ellis et al.

FOREIGN PATENT DOCUMENTS

| WO | WO 00/34265 A1 | 6/2000 |
|---|---|---|
| WO | WO 2004/011436 A1 | 2/2004 |
| WO | WO 2005/070430 A1 | 8/2005 |
| WO | WO 2005/075428 A1 | 8/2005 |
| WO | WO 2005/117875 A1 | 12/2005 |
| WO | WO 2006/035051 A1 | 4/2006 |
| WO | WO 2005/070924 A1 | 5/2006 |
| WO | WO 2006/067048 A1 | 6/2006 |
| WO | WO 2006/131519 A1 | 12/2006 |
| WO | WO 2007/000434 A1 | 1/2007 |
| WO | WO 2007/000435 A1 | 1/2007 |

OTHER PUBLICATIONS

Vippagunta et al. Advanced Drug Delivery Reviews, vol. 48, pp. 3-26 (2001).*
Andries, K., et al. "A Diaryiquinotine drug active on the ATP Synthase of Mycobacterium Tuberculosis", Science (Washington D.C.), vol. 307, No. 5707, 2005, pp. 223-227.
Zurenko, G., et al. In vitro activities of U-100592 and U-100766, novel oxazolidinone antibacterial agents. Antimicrob. Agents Chemother. 40, 839-845 (1996).

* cited by examiner

*Primary Examiner* — Emily Bernhardt
(74) *Attorney, Agent, or Firm* — Thomas J. Dodd

(57) ABSTRACT

The present invention relates to novel substituted quinoline derivatives according to the general Formula (Ia) or Formula (Ib):

(Ia)

(Ib)

including any stereochemically isomeric form thereof, a N-oxide thereof, a pharmaceutically acceptable salt thereof or a solvate thereof. The claimed compounds are useful for the treatment of a bacterial infection. Also claimed is a composition comprising a pharmaceutically acceptable carrier and, as active ingredient, a therapeutically effective amount of the claimed compounds, the use of the claimed compounds or compositions for the manufacture of a medicament for the treatment of a bacterial infection and a process for preparing the claimed compounds.

28 Claims, No Drawings

ANTIBACTERIAL QUINOLINE DERIVATIVES

CROSS REFERENCE TO RELATED APPLICATIONS

This application is a national stage application of Patent Application No. PCT/EP2007/063314 filed Dec. 4, 2007, which in turn claims the benefit of EPO Patent Application No. 06125510.5 filed Dec. 6, 2006. The complete disclosures of the aforementioned related patent applications are hereby incorporated herein by reference for all purposes.

The present invention relates to novel substituted quinoline derivatives useful for the treatment of bacterial diseases, including but not limited to diseases caused by pathogenic mycobacteria such as *Mycobacterium tuberculosis, M. bovis, M. leprae, M. avium* and *M. marinum*, or pathogenic Staphylococci or Streptococci.

BACKGROUND OF THE INVENTION

*Mycobacterium tuberculosis* is the causative agent of tuberculosis (TB), a serious and potentially fatal infection with a world-wide distribution. Estimates from the World Health Organization indicate that more than 8 million people contract TB each year, and 2 million people die from tuberculosis yearly. In the last decade, TB cases have grown 20% worldwide with the highest burden in the most impoverished communities. If these trends continue, TB incidence will increase by 41% in the next twenty years. Fifty years since the introduction of an effective chemotherapy, TB remains after AIDS, the leading infectious cause of adult mortality in the world. Complicating the TB epidemic is the rising tide of multi-drug-resistant strains, and the deadly symbiosis with HIV. People who are HIV-positive and infected with TB are 30 times more likely to develop active TB than people who are HIV-negative and TB is responsible for the death of one out of every three people with HIV/AIDS worldwide Existing approaches to treatment of tuberculosis all involve the combination of multiple agents. For example, the regimen recommended by the U.S. Public Health Service is a combination of isoniazid, rifampicin and pyrazinamide for two months, followed by isoniazid and rifampicin alone for a further four months. These drugs are continued for a further seven months in patients infected with HIV. For patients infected with multi-drug resistant strains of *M. tuberculosis*, agents such as ethambutol, streptomycin, kanamycin, amikacin, capreomycin, ethionamide, cycloserine, ciprofoxacin and ofloxacin are added to the combination therapies. There exists no single agent that is effective in the clinical treatment of tuberculosis, nor any combination of agents that offers the possibility of therapy of less than six months' duration.

There is a high medical need for new drugs that improve current treatment by enabling regimens that facilitate patient and provider compliance. Shorter regimens and those that require less supervision are the best way to achieve this. Most of the benefit from treatment comes in the first 2 months, during the intensive, or bactericidal, phase when four drugs are given together; the bacterial burden is greatly reduced, and patients become noninfectious. The 4- to 6-month continuation, or sterilizing, phase is required to eliminate persisting bacilli and to minimize the risk of relapse. A potent sterilizing drug that shortens treatment to 2 months or less would be extremely beneficial. Drugs that facilitate compliance by requiring less intensive supervision also are needed. Obviously, a compound that reduces both the total length of treatment and the frequency of drug administration would provide the greatest benefit.

Complicating the TB epidemic is the increasing incidence of multi-drug-resistant strains or MDR-TB. Up to four percent of all cases worldwide are considered MDR-TB—those resistant to the most effective drugs of the four-drug standard, isoniazid and rifampin. MDR-TB is lethal when untreated and cannot be adequately treated through the standard therapy, so treatment requires up to 2 years of "second-line" drugs. These drugs are often toxic, expensive and marginally effective. In the absence of an effective therapy, infectious MDR-TB patients continue to spread the disease, producing new infections with MDR-TB strains. There is a high medical need for a new drug with a new mechanism of action, which is likely to demonstrate activity against drug resistant, in particular MDR strains.

The term "drug resistant" as used hereinbefore or hereinafter is a term well understood by the person skilled in microbiology. A drug resistant *Mycobacterium* is a *Mycobacterium* which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs.

MDR tuberculosis is a specific form of drug resistant tuberculosis due to a bacterium resistant to at least isoniazid and rifampicin (with or without resistance to other drugs), which are at present the two most powerful anti-TB drugs. Thus, whenever used hereinbefore or hereinafter "drug resistant" includes multi drug resistant.

Another factor in the control of the TB epidemic is the problem of latent TB. In spite of decades of tuberculosis (TB) control programs, about 2 billion people are infected by *M. tuberculosis*, though asymptotically. About 10% of these individuals are at risk of developing active TB during their lifespan. The global epidemic of TB is fuelled by infection of HIV patients with TB and rise of multi-drug resistant TB strains (MDR-TB). The reactivation of latent TB is a high risk factor for disease development and accounts for 32% deaths in HIV infected individuals. To control TB epidemic, the need is to discover new drugs that can kill dormant or latent bacilli. The dormant TB can get reactivated to cause disease by several factors like suppression of host immunity by use of immunosuppressive agents like antibodies against tumor necrosis factor α or interferon-γ. In case of HIV positive patients the only prophylactic treatment available for latent TB is two-three months regimens of rifampicin, pyrazinamide. The efficacy of the treatment regime is still not clear and furthermore the length of the treatments is an important constrain in resource-limited environments. Hence there is a drastic need to identify new drugs, which can act as chemoprophylatic agents for individuals harboring latent TB bacilli.

The tubercle bacilli enter healthy individuals by inhalation; they are phagocytosed by the alveolar macrophages of the lungs. This leads to potent immune response and formation of granulomas, which consist of macrophages infected with *M. tuberculosis* surrounded by T cells. After a period of 6-8 weeks the host immune response cause death of infected cells by necrosis and accumulation of caseous material with certain extracellular bacilli, surrounded by macrophages, epitheloid cells and layers of lymphoid tissue at the periphery. In case of healthy individuals, most of the mycobacteria are killed in these environments but a small proportion of bacilli still survive and are thought to exist in a non-replicating, hypermetabolic state and are tolerant to killing by anti-TB drugs like isoniazid. These bacilli can remain in the altered physiological environments even for individual's lifetime without showing any clinical symptoms of disease. However, in 10% of the cases these latent bacilli may reactivate to cause disease. One of the hypothesis about development of these persistent bacteria is patho-physiological environment in human lesions namely, reduced oxygen tension, nutrient limitation, and acidic pH. These factors have been postulated to render these bacteria phenotypically tolerant to major anti-mycobacterial drugs.

In addition to the management of the TB epidemic, there is the emerging problem of resistance to first-line antibiotic agents. Some important examples include penicillin-resistant *Streptococcus pneumoniae*, vancomycin-resistant enterococci, methicillin-resistant *Staphylococcus aureus*, multi-resistant salmonellae.

The consequences of resistance to antibiotic agents are severe. Infections caused by resistant microbes fail to respond to treatment, resulting in prolonged illness and greater risk of death. Treatment failures also lead to longer periods of infectivity, which increase the numbers of infected people moving in the community and thus exposing the general population to the risk of contracting a resistant strain infection. Hospitals are a critical component of the antimicrobial resistance problem worldwide. The combination of highly susceptible patients, intensive and prolonged antimicrobial use, and cross-infection has resulted in infections with highly resistant bacterial pathogens.

Self-medication with antimicrobials is another major factor contributing to resistance. Self-medicated antimicrobials may be unnecessary, are often inadequately dosed, or may not contain adequate amounts of active drug.

Patient compliance with recommended treatment is another major problem. Patients forget to take medication, interrupt their treatment when they begin to feel better, or may be unable to afford a full course, thereby creating an ideal environment for microbes to adapt rather than be killed.

Because of the emerging resistance to multiple antibiotics, physicians are confronted with infections for which there is no effective therapy. The morbidity, mortality, and financial costs of such infections impose an increasing burden for health care systems worldwide.

Therefore, there is a high need for new compounds to treat bacterial infections, especially mycobacterial infections including drug resistant and latent mycobacterial infections, and also other bacterial infections especially those caused by resistant bacterial strains.

WO2004/011436, WO2005/070924, WO2005/070430 and WO2005/075428 disclose certain substituted quinoline derivatives having activity against *Mycobacteria*, in particular against *Mycobacterium tuberculosis*. WO2005/117875 describes substituted quinoline derivatives having activity against resistant Mycobacterial strains. WO2006/067048 describes substituted quinoline derivatives having activity against latent tuberculosis. One particular compound of these substituted quinoline derivatives is described in Science (2005), 307, 223-227 and its mode of action is described in WO2006/035051.

Other substituted quinolines are disclosed in U.S. Pat. No. 5,965,572 (The United States of America) for treating antibiotic resistant infections and in WO00/34265 to inhibit the growth of bacterial microorganisms.

The purpose of the present invention is to provide novel compounds, in particular substituted quinoline derivatives, having the property of inhibiting bacterial growth especially of Streptococci, Staphylococci or mycobacteria and therefore useful for the treatment of bacterial diseases, particularly those diseases caused by pathogenic bacteria such as *Streptococcus pneumonia, Staphylococcus aureus* or *Mycobacterium tuberculosis* (including the latent disease and including drug resistant *M. tuberculosis* strains), *M. bovis, M. leprae, M. avium* and *M. marinum*.

SUMMARY OF THE INVENTION

The present invention relates to novel substituted quinoline derivatives according to formula (Ia) or (Ib):

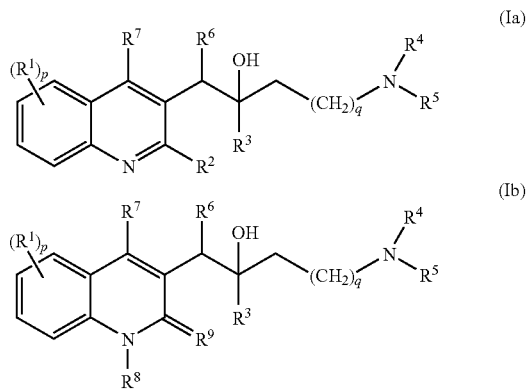

including any stereochemically isomeric form thereof, wherein p is an integer equal to 1, 2, 3 or 4;
q is an integer equal to zero, 1, 2, 3 or 4;
$R^1$ is hydrogen, cyano, halo, alkyl, haloalkyl, hydroxy, alkyloxy, alkylthio, alkylthioalkyl, arylalkyl, di(aryl)alkyl, aryl, or Het;
$R^2$ is hydrogen, alkyloxy, aryl, aryloxy, hydroxy, mercapto, alkyloxyalkyloxy, alkylthio, mono or di(alkyl)amino, pyrrolidino or a radical of formula

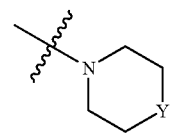

wherein Y is $CH_2$, O, S, NH or N-alkyl;
$R^3$ is alkyl, arylalkyl, aryl-O-alkyl, aryl-alkyl-O-alkyl, aryl, aryl-aryl, Het, Het-alkyl, Het-O-alkyl, Het-alkyl-O-alkyl or

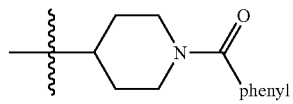

$R^4$ and $R^5$ each independently are hydrogen, alkyl or benzyl; or
$R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, each radical optionally substituted with alkyl, halo, haloalkyl, hydroxy, alkyloxy, amino, mono- or dialkylamino, alkylthio, alkyloxyalkyl, alkylthioalkyl and pyrimidinyl;

$R^6$ is aryl$^1$ or Het;
$R^7$ is hydrogen, halo, alkyl, aryl or Het;
$R^8$ is hydrogen or alkyl;
$R^9$ is oxo; or
$R^8$ and $R^9$ together form the radical —CH═CH—N═;

aryl is a homocycle selected from phenyl, naphthyl, acenaphthyl or tetrahydronaphthyl, each being optionally substituted with 1, 2 or 3 substituents, each substituent being independently selected from hydroxy, halo, cyano, nitro, amino, mono- or dialkylamino, alkyl, $C_{2-6}$alkenyl optionally substituted with phenyl, haloalkyl, alkyloxy, haloalkyloxy, carboxyl, alkyloxycarbonyl, aminocarbonyl, morpholinyl or mono- or dialkylaminocarbonyl;

aryl$^1$ is a homocycle selected from phenyl, naphthyl, acenaphthyl or tetrahydronaphthyl, each being optionally substituted with 1, 2 or 3 substituents, each substituent being independently selected from hydroxy, halo, cyano, nitro, amino, mono- or dialkylamino, alkyl, haloalkyl, alkyloxy, alkylthio, haloalkyloxy, carboxyl, alkyloxycarbonyl, aminocarbonyl, morpholinyl, Het or mono- or dialkylaminocarbonyl;

Het is a monocyclic heterocycle selected from N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl or pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle being optionally substituted with 1, 2 or 3 substituents, each substituent independently selected from halo, hydroxy, alkyl or alkyloxy;

provided that if $R^3$ is alkyl, arylalkyl, aryl, Het, Het-alkyl or

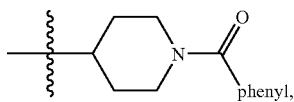

then $R^6$ is Het; phenyl substituted with Het; naphthyl substituted with Het; or acenaphthyl or tetrahydronaphthyl, each being optionally substituted with 1, 2 or 3 substituents, each substituent being independently selected from hydroxy, halo, cyano, nitro, amino, mono- or dialkylamino, alkyl, haloalkyl, alkyloxy, alkylthio, haloalkyloxy, carboxyl, alkyloxycarbonyl, aminocarbonyl, morpholinyl, Het or mono- or dialkylaminocarbonyl;

the N-oxides thereof, the pharmaceutically acceptable salts thereof or the solvates thereof.

Whenever used herein, the term "compounds of formula (Ia) or (Ib)" or "compounds according to the invention" is meant to also include their pharmaceutically acceptable salts or their N-oxide forms.

The compounds of formula (Ia) and (Ib) are interrelated in that e.g. a compound according to formula (Ib), with $R^9$ equal to oxo and $R^8$ equal to hydrogen, is the tautomeric equivalent of a compound according to formula (Ia) with $R^2$ equal to hydroxy (keto-enol tautomerism).

In the definition of Het, it is meant to include all the possible isomeric forms of the heterocycles, for instance, pyrrolyl comprises 1H-pyrrolyl and 2H-pyrrolyl.

The aryl, aryl$^1$ or Het listed in the definitions of the substituents of the compounds of formula (Ia) or (Ib) (see for instance $R^3$) as mentioned hereinbefore or hereinafter may be attached to the remainder of the molecule of formula (Ia) or (Ib) through any ring carbon or heteroatom as appropriate, if not otherwise specified. Thus, for example, when Het is imidazolyl, it may be 1-imidazolyl, 2-imidazolyl, 4-imidazolyl and the like.

Lines drawn from substituents into ring systems indicate that the bond may be attached to any of the suitable ring atoms.

The pharmaceutically acceptable salts as mentioned hereinbefore or hereinafter are meant to comprise the therapeutically active non-toxic acid addition salt forms which the compounds according to formula (Ia) or formula (Ib) are able to form. Said acid addition salts can be obtained by treating the base form of the compounds according to formula (Ia) or formula (Ib) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds of formula (Ia) or (Ib) containing acidic protons may be converted into their therapeutically active non-toxic metal or amine addition salt forms by treatment with appropriate organic and inorganic bases. The pharmaceutically acceptable salts as mentioned hereinbefore or hereinafter are meant to also comprise the therapeutically active non-toxic metal or amine addition salt forms (base addition salt forms) which the compounds of formula (Ia) or (Ib) are able to form. Appropriate base addition salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like.

Conversely, said acid or base addition salt forms can be converted into the free forms by treatment with an appropriate base or acid.

The term pharmaceutically acceptable salt also comprises the quaternary ammonium salts (quaternary amines) which the compounds of formula (Ia) or (Ib) are able to form by reaction between a basic nitrogen of a compound of formula (Ia) or (Ib) and an appropriate quaternizing agent, such as, for example, an optionally substituted $C_{1-6}$alkylhalide, aryl$C_{1-6}$alkylhalide, $C_{1-6}$alkylcarbonylhalide, arylcarbonylhalide, Het$C_{1-6}$alkylhalide or Hetcarbonylhalide, e.g. methyliodide or benzyliodide. Preferably, Het represents a monocyclic heterocycle selected from furanyl or thienyl; or a bicyclic heterocycle selected from benzofuranyl or benzothienyl; each monocyclic and bicyclic heterocycle may optionally be substituted with 1, 2 or 3 substituents, each substituent independently selected from the group of halo, alkyl and aryl. Preferably, the quaternizing agent is $C_{1-6}$alkylhalide. Other reactants with good leaving groups may also be used, such as $C_{1-6}$alkyl trifluoromethanesulfonates, $C_{1-6}$alkyl methanesulfonates, and $C_{1-6}$alkyl p-toluenesulfonates. A quaternary amine has a positively charged nitrogen. Pharmaceutically acceptable counterions include chloro, bromo, iodo, trifluoroacetate, acetate, triflate, sulfate, sulfonate. Preferably, the counterion is iodo. The counterion of choice can be introduced using ion exchange resins.

The term solvate comprises the hydrates and solvent addition forms which the compounds of formula (Ia) or (Ib) are able to form, as well as the salts thereof. Examples of such forms are e.g. hydrates, alcoholates and the like.

In the framework of this application, a compound according to the invention is inherently intended to comprise all stereochemically isomeric forms thereof. The term "stereochemically isomeric forms" as used hereinbefore or hereinafter defines all the possible stereoisomeric forms which the compounds of formula (Ia) and (Ib), and their N-oxides, pharmaceutically acceptable salts or physiologically functional derivatives may possess. Unless otherwise mentioned or indicated, the chemical designation of compounds denotes the mixture of all possible stereochemically isomeric forms. In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (Ia) and (Ib) are obviously intended to be embraced within the scope of this invention. Of special interest are those compounds of formula (Ia) or (Ib) which are stereochemically pure.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s). Thus, when a compound of formula (Ia) or (Ib) is for instance specified as (R,S), this means that the compound is substantially free of the (S,R) isomer.

Compounds of either formula (Ia) and (Ib) and some of the intermediate compounds invariably have at least two stereogenic centers in their structure which may lead to at least 4 stereochemically different structures.

The compounds of either formula (Ia) and (Ib) may be synthesized in the form of mixtures, in particular racemic mixtures, of enantiomers which can be separated from one another following art-known resolution procedures. The racemic compounds of either formula (Ia) and (Ib) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of either formula (Ia) and (Ib) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomeric forms of the compounds of formula (Ia) or (Ib) are meant to comprise those compounds of formula (Ia) or (Ib) wherein e.g. an enol group is converted into a keto group (keto-enol tautomerism). Tautomeric forms of the compounds of formula (Ia) and (Ib) or of intermediates of the present invention are intended to be embraced by the ambit of this invention.

The N-oxide forms of the present compounds are meant to comprise the compounds of formula (Ia) or (Ib) wherein one or several tertiary nitrogen atoms are oxidized to the so-called N-oxide.

The compounds of formula (Ia) and (Ib) may be converted to the corresponding N-oxide forms following art-known procedures for converting a trivalent nitrogen into its N-oxide form. Said N-oxidation reaction may generally be carried out by reacting the starting material of formula (Ia) or (Ib) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

In the framework of this application, a compound according to the invention is inherently intended to comprise all isotopic combinations of its chemical elements. In the framework of this application, a chemical element, in particular when mentioned in relation to a compound according to formula (Ia) or (Ib), comprises all isotopes and isotopic mixtures of this element, either naturally occurring or synthetically produced, either with natural abundance or in an isotopically enriched form. In particular, when hydrogen is mentioned, it is understood to refer to $^1H$, $^2H$, $^3H$ and mixtures thereof; when carbon is mentioned, it is understood to refer to $^{11}C$, $^{12}C$, $^{13}C$, $^{14}C$ and mixtures thereof; when nitrogen is mentioned, it is understood to refer to $^{13}N$, $^{14}N$, $^{15}N$ and mixtures thereof; when oxygen is mentioned, it is understood to refer to $^{14}$O, $^{15}$O, $^{16}$O, $^{17}$O, $^{18}$O and mixtures thereof; and when fluor is mentioned, it is understood to refer to $^{18}$F, $^{19}$F and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to formula (Ia) or (Ib), a pharmaceutically acceptable salt thereof or an N-oxide form thereof, which contains at least one radioactive atom. For example, a compound can be labelled with positron or with gamma emitting radioactive isotopes. For radioligand-binding techniques (membrane receptor assay), the $^3$H-atom or the $^{125}$I-atom is the atom of choice to be replaced. For imaging, the most commonly used positron emitting (PET) radioactive isotopes are $^{11}$C, $^{18}$F, $^{15}$O and $^{13}$N, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}$F, $^{99m}$Tc, $^{201}$Tl and $^{123}$I. The handling of these radioactive isotopes, their production, isolation and incorporation in a molecule are known to the skilled person.

In particular, the radioactive atom is selected from the group of hydrogen, carbon, nitrogen, sulfur, oxygen and halogen. Preferably, the radioactive atom is selected from the group of hydrogen, carbon and halogen.

In particular, the radioactive isotope is selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

In the framework of this application, alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with cyano, hydroxy, $C_{1-6}$alkyloxy or oxo. Preferably alkyl is a straight or branched saturated hydrocarbon radical having from 1 to 6 carbon atoms; or is a cyclic saturated hydrocarbon radical having from 3 to 6 carbon atoms; wherein each carbon atom can be optionally substituted with hydroxyl or $C_{1-6}$alkyloxy.

Preferably, alkyl is methyl, ethyl or cyclohexylmethyl, more preferably methyl or ethyl. An interesting embodiment of alkyl in all definitions used hereinbefore or hereinafter is $C_{1-6}$alkyl which represents a straight or branched saturated hydrocarbon radical having from 1 to 6 carbon atoms such as for example methyl, ethyl, propyl, 2-methyl-ethyl, pentyl, hexyl and the like. A preferred subgroup of $C_{1-6}$alkyl is $C_{1-4}$alkyl which represents a straight or branched saturated hydrocarbon radical having from 1 to 4 carbon atoms such as for example methyl, ethyl, propyl, 2-methyl-ethyl and the like.

In the framework of this application, $C_{2-6}$alkenyl is a straight or branched hydrocarbon radical having from 2 to 6 carbon atoms containing a double bond such as ethenyl, propenyl, butenyl, pentenyl, hexenyl and the like; $C_{3-6}$cycloalkyl is a cyclic saturated hydrocarbon radical having from 3 to 6 carbon atoms and is generic to cyclopropyl, cyclobutyl, cyclopentyl, cyclohexyl In the framework of this application, halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms or a cyclic saturated hydrocarbon radical having from 3 to 6 carbon atoms attached to a straight or branched saturated hydrocarbon radical having from 1 to 6 carbon atoms; wherein one or more carbon atoms are substituted with one or more halo atoms. Preferably, halo is bromo, fluoro or chloro; in particular chloro or bromo. Preferably, haloalkyl is polyhalo$C_{1-6}$alkyl which is defined as mono- or polyhalosubstituted $C_{1-6}$alkyl, for example, methyl with one or more fluoro atoms, for example, difluoromethyl or trifluoromethyl, 1,1-difluoroethyl and the like. In case more than one halo atom is attached to an alkyl or $C_{1-6}$alkyl group within the definition of haloalkyl or polyhalo$C_{1-6}$alkyl, they may be the same or different.

A first interesting embodiment relates to a compound of formula (Ia) or (Ib) wherein
  p is an integer equal to 1, 2, 3 or 4;
  q is an integer equal to zero, 1, 2, 3 or 4;
  $R^1$ is hydrogen, cyano, halo, alkyl, haloalkyl, hydroxy, alkyloxy, alkylthio, alkylthioalkyl, arylalkyl, di(aryl)alkyl, aryl, or Het;
  $R^2$ is hydrogen, alkyloxy, aryl, aryloxy, hydroxy, mercapto, alkyloxyalkyloxy, alkylthio, mono or di(alkyl)amino, pyrrolidino or a radical of formula

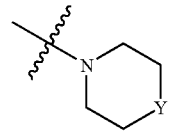

wherein Y is $CH_2$, O, S, NH or N-alkyl;
  $R^3$ is alkyl, arylalkyl, aryl-O-alkyl, aryl-alkyl-O-alkyl, aryl, Het, Het-alkyl, Het-O-alkyl, Het-alkyl-O-alkyl or

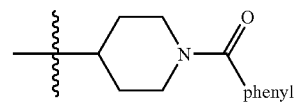

$R^4$ and $R^5$ each independently are hydrogen, alkyl or benzyl; or
  $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, each radical optionally substituted with alkyl, halo, haloalkyl, hydroxy, alkyloxy, amino, mono- or dialkylamino, alkylthio, alkyloxyalkyl, alkylthioalkyl and pyrimidinyl;
  $R^6$ is aryl$^1$ or Het;
  $R^7$ is hydrogen, halo, alkyl, aryl or Het;
  $R^8$ is hydrogen or alkyl;
  $R^9$ is oxo; or
  $R^8$ and $R^9$ together form the radical —CH=CH—N=;
  aryl is a homocycle selected from phenyl, naphthyl, acenaphthyl or tetrahydronaphthyl, each being optionally substituted with 1, 2 or 3 substituents, each substituent being independently selected from hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl or mono- or dialkylaminocarbonyl;

aryl¹ is a homocycle selected from phenyl, naphthyl, acenaphthyl or tetrahydronaphthyl, each being optionally substituted with 1, 2 or 3 substituents, each substituent being independently selected from hydroxy, halo, cyano, nitro, amino, mono- or dialkylamino, alkyl, haloalkyl, alkyloxy, alkylthio, haloalkyloxy, carboxyl, alkyloxycarbonyl, aminocarbonyl, morpholinyl, Het or mono- or dialkylaminocarbonyl;

Het is a monocyclic heterocycle selected from N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl or pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle being optionally substituted with 1, 2 or 3 substituents, each substituent independently selected from halo, hydroxy, alkyl or alkyloxy;

provided that if $R^3$ is alkyl, arylalkyl, aryl, Het, Het-alkyl or

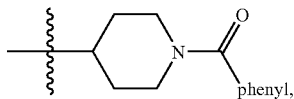

then $R^6$ is Het; phenyl substituted with Het; naphthyl substituted with Het; or acenaphthyl or tetrahydronaphthyl, each being optionally substituted with 1, 2 or 3 substituents, each substituent being independently selected from hydroxy, halo, cyano, nitro, amino, mono- or dialkylamino, alkyl, haloalkyl, alkyloxy, alkylthio, haloalkyloxy, carboxyl, alkyloxycarbonyl, aminocarbonyl, morpholinyl, Het or mono- or dialkylaminocarbonyl.

A second interesting embodiment relates to a compound of formula (Ia) or (Ib) wherein p is an integer equal to 1, 2, 3 or 4;

q is an integer equal to zero, 1, 2, 3 or 4;

$R^1$ is hydrogen, cyano, halo, $C_{1-6}$alkyl, polyhalo$C_{1-6}$alkyl, hydroxy, $C_{1-6}$alkyloxy, $C_{1-6}$alkylthio, $C_{1-6}$alkyloxy$C_{1-6}$alkyl, $C_{1-6}$alkylthio$C_{1-6}$alkyl, hydroxy$C_{1-6}$alkyl, aryl$C_{1-6}$alkyl, di(aryl)$C_{1-6}$alkyl, aryl, or Het;

$R^2$ is hydrogen, $C_{1-6}$alkyloxy, aryl, aryloxy, hydroxy, mercapto, $C_{1-6}$alkyloxy$C_{1-6}$alkyloxy, $C_{1-6}$alkylthio, mono or di($C_{1-6}$alkyl)amino, pyrrolidino or a radical of formula

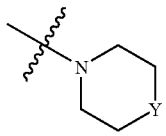

wherein Y is $CH_2$, O, S, NH or N—$C_{1-6}$alkyl;

$R^3$ is $C_{1-6}$alkyl, $C_{3-6}$cycloalkyl, aryl$C_{1-6}$alkyl, aryl-O—$C_{1-6}$alkyl, aryl$C_{1-6}$alkyl-O—$C_{1-6}$alkyl, aryl, aryl-aryl, Het, Het-$C_{1-6}$alkyl, Het-O—$C_{1-6}$alkyl or Het$C_{1-6}$alkyl-O—$C_{1-6}$alkyl, or

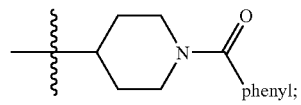

$R^4$ and $R^5$ each independently are hydrogen, $C_{1-6}$alkyl or benzyl; or $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, each radical optionally substituted with $C_{1-6}$alkyl, halo, polyhalo$C_{1-6}$alkyl, hydroxy, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl and pyrimidinyl;

$R^6$ is aryl¹ or Het;

$R^7$ is hydrogen, halo, $C_{1-6}$alkyl, aryl or Het;

$R^8$ is hydrogen or $C_{1-6}$alkyl;

$R^9$ is oxo; or $R^8$ and $R^9$ together form the radical —CH=CH—N=;

aryl is a homocycle selected from phenyl, naphthyl, acenaphthyl or tetrahydronaphthyl, each being optionally substituted with 1, 2 or 3 substituents, each substituent being independently selected from hydroxy, halo, cyano, nitro, amino, mono- or di($C_{1-6}$alkyl)amino, $C_{1-6}$alkyl, $C_{2-6}$alkenyl optionally substituted with phenyl, polyhalo$C_{1-6}$alkyl, $C_{1-6}$alkyloxy, halo$C_{1-6}$alkyloxy, carboxyl, $C_{1-6}$alkyloxycarbonyl, aminocarbonyl, morpholinyl or mono- or di($C_{1-6}$alkyl)aminocarbonyl;

aryl¹ is a homocycle selected from phenyl, naphthyl, acenaphthyl or tetrahydronaphthyl, each being optionally substituted with 1, 2 or 3 substituents, each substituent being independently selected from hydroxy, halo, cyano, nitro, amino, mono- or di($C_{1-6}$alkyl)amino, $C_{1-6}$alkyl, polyhalo$C_{1-6}$alkyl, $C_{1-6}$alkyloxy, $C_{1-6}$alkylthio, halo$C_{1-6}$alkyloxy, carboxyl, $C_{1-6}$alkyloxycarbonyl, aminocarbonyl, morpholinyl, Het or mono- or di($C_{1-6}$alkyl)aminocarbonyl;

Het is a monocyclic heterocycle selected from N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl or pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle being optionally substituted with 1, 2 or 3 substituents, each substituent independently selected from halo, hydroxy, $C_{1-6}$alkyl or $C_{1-6}$alkyloxy;

provided that if $R^3$ is $C_{1-6}$alkyl, $C_{3-6}$cycloalkyl, aryl$C_{1-6}$alkyl, aryl, Het, Het-$C_{1-6}$alkyl or

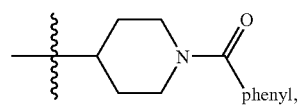

then $R^6$ is Het; phenyl substituted with Het; naphthyl substituted with Het; or acenaphthyl or tetrahydronaphthyl, each being optionally substituted with 1, 2 or 3 substituents, each substituent being independently selected from hydroxy, halo, cyano, nitro, amino, mono- or di(C$_{1-6}$alkyl)amino, C$_{1-6}$alkyl, polyhaloC$_{1-6}$alkyl, C$_{1-6}$alkyloxy, C$_{1-6}$alkylthio, haloC$_{1-6}$alkyloxy, carboxyl, C$_{1-6}$alkyloxycarbonyl, aminocarbonyl, morpholinyl, Het or mono- or di(C$_{1-6}$alkyl)aminocarbonyl.

A third interesting embodiment relates to a compound of formula (Ia) or (Ib) wherein
p is an integer equal to 1, 2, 3 or 4;
q is an integer equal to zero, 1, 2, 3 or 4;
R$^1$ is hydrogen, cyano, halo, C$_{1-6}$alkyl, polyhaloC$_{1-6}$alkyl, hydroxy, C$_{1-6}$alkyloxy, C$_{1-6}$alkylthio, C$_{1-6}$alkyloxyC$_{1-6}$alkyl, C$_{1-6}$alkylthioC$_{1-6}$alkyl, hydroxyC$_{1-6}$alkyl, arylC$_{1-6}$alkyl, di(aryl)C$_{1-6}$alkyl, aryl, or Het;
R$^2$ is hydrogen, C$_{1-6}$alkyloxy, aryl, aryloxy, hydroxy, mercapto, C$_{1-6}$alkyloxyC$_{1-6}$alkyloxy, C$_{1-6}$alkylthio, mono or di(C$_{1-6}$alkyl)amino, pyrrolidino or a radical of formula

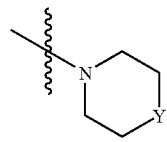

wherein Y is CH$_2$, O, S, NH or N—C$_{1-6}$alkyl;
R$^3$ is C$_{1-6}$alkyl, C$_{3-6}$cycloalkyl, arylC$_{1-6}$alkyl, aryl-O—C$_{1-6}$alkyl, arylC$_{1-6}$alkyl-O—C$_{1-6}$alkyl, aryl Het, Het-C$_{1-6}$alkyl, Het-O—C$_{1-6}$alkyl or HetC$_{1-6}$alkyl-O—C$_{1-6}$alkyl, or

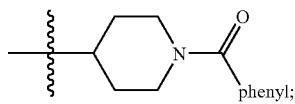

R$^4$ and R$^5$ each independently are hydrogen, C$_{1-6}$alkyl or benzyl; or
R$^4$ and R$^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, each radical optionally substituted with C$_{1-6}$alkyl, halo, polyhaloC$_{1-6}$alkyl, hydroxy, C$_{1-6}$alkyloxy, amino, mono- or di(C$_{1-6}$alkyl)amino, C$_{1-6}$alkylthio, C$_{1-6}$alkyloxyC$_{1-6}$alkyl, C$_{1-6}$alkylthioC$_{1-6}$alkyl and pyrimidinyl;
R$^6$ is aryl$^1$ or Het;
R$^7$ is hydrogen, halo, C$_{1-6}$alkyl, aryl or Het;
R$^8$ is hydrogen or C$_{1-6}$alkyl;
R$^9$ is oxo; or
R$^8$ and R$^9$ together form the radical —CH=CH—N=;
aryl is a homocycle selected from phenyl, naphthyl, acenaphthyl or tetrahydronaphthyl, each being optionally substituted with 1, 2 or 3 substituents, each substituent being independently selected from hydroxy, halo, cyano, nitro, amino, mono- or di(C$_{1-6}$alkyl)amino, C$_{1-6}$alkyl, polyhaloC$_{1-6}$alkyl, C$_{1-6}$alkyloxy, haloC$_{1-6}$alkyloxy, carboxyl, C$_{1-6}$alkyloxycarbonyl, aminocarbonyl, morpholinyl or mono- or di(C$_{1-6}$alkyl)aminocarbonyl;
aryl$^1$ is a homocycle selected from phenyl, naphthyl, acenaphthyl or tetrahydronaphthyl, each being optionally substituted with 1, 2 or 3 substituents, each substituent being independently selected from hydroxy, halo, cyano, nitro, amino, mono- or di(C$_{1-6}$alkyl)amino, C$_{1-6}$alkyl, polyhaloC$_{1-6}$alkyl, C$_{1-6}$alkyloxy, C$_{1-6}$alkylthio, haloC$_{1-6}$alkyloxy, carboxyl, C$_{1-6}$alkyloxycarbonyl, aminocarbonyl, morpholinyl, Het or mono- or di(C$_{1-6}$alkyl)aminocarbonyl;
Het is a monocyclic heterocycle selected from N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl or pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle being optionally substituted with 1, 2 or 3 substituents, each substituent independently selected from halo, hydroxy, C$_{1-6}$alkyl or C$_{1-6}$alkyloxy;
provided that if R$^3$ is C$_{1-6}$alkyl, C$_{3-6}$cycloalkyl, arylC$_{1-6}$alkyl, aryl, Het, Het-C$_{1-6}$alkyl or

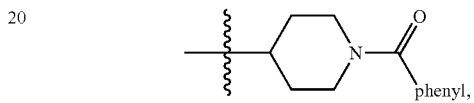

then R$^6$ is Het; phenyl substituted with Het; naphthyl substituted with Het; or acenaphthyl or tetrahydronaphthyl, each being optionally substituted with 1, 2 or 3 substituents, each substituent being independently selected from hydroxy, halo, cyano, nitro, amino, mono- or di(C$_{1-6}$alkyl)amino, C$_{1-6}$alkyl, polyhaloC$_{1-6}$alkyl, C$_{1-6}$alkyloxy,
C$_{1-6}$alkylthio, haloC$_{1-6}$alkyloxy, carboxyl, C$_{1-6}$alkyloxycarbonyl, aminocarbonyl, morpholinyl, Het or mono- or di(C$_{1-6}$alkyl)aminocarbonyl.

A fourth interesting embodiment relates to a compound of formula (Ia) or (Ib) or any subgroup thereof as mentioned hereinbefore as interesting embodiment wherein R$^1$ is hydrogen, halo, aryl, Het, alkyl or alkyloxy; more in particular R$^1$ is hydrogen or halo. Most preferably, R$^1$ is halo, in particular bromo.

A fifth interesting embodiment relates to a compound of formula (Ia) or (Ib) or any subgroup thereof as mentioned hereinbefore as interesting embodiment wherein p is equal to 1.

A sixth interesting embodiment relates to a compound of formula (Ia) or (Ib) or any subgroup thereof as mentioned hereinbefore as interesting embodiment wherein R$^2$ is hydrogen, alkyloxy or alkylthio, in particular hydrogen, C$_{1-6}$alkyloxy or C$_{1-6}$alkylthio. More in particular, R$^2$ is C$_{1-6}$alkyloxy, preferably methyloxy.

A seventh interesting embodiment relates to a compound of formula (Ia) or (Ib) or any subgroup thereof as mentioned hereinbefore as interesting embodiment wherein R$^3$ is aryl-O—C$_{1-6}$alkyl, arylC$_{1-6}$alkyl-O—C$_{1-6}$alkyl, aryl, aryl-aryl, Het, Het-C$_{1-6}$alkyl, Het-O—C$_{1-6}$alkyl, HetC$_{1-6}$alkyl-O—C$_{1-6}$ alkyl; in particular R$^3$ is aryl-O—C$_{1-6}$alkyl, arylC$_{1-6}$alkyl-O—C$_{1-6}$alkyl, Het-C$_{1-6}$alkyl, Het-O—C$_{1-6}$alkyl, HetC$_{1-6}$ alkyl-O—C$_{1-6}$alkyl; more in particular R$^3$ is aryl-O—C$_{1-6}$ alkyl, arylC$_{1-6}$alkyl-O—C$_{1-6}$alkyl, aryl-aryl, Het-O—C$_{1-6}$ alkyl, HetC$_{1-6}$alkyl-O—C$_{1-6}$alkyl; even more in particular R$^3$ is aryl-O—C$_{1-6}$alkyl, arylC$_{1-6}$alkyl-O—C$_{1-6}$alkyl, Het-O—C$_{1-6}$alkyl or HetC$_{1-6}$alkyl-O—C$_{1-6}$alkyl; or R$^3$ is aryl-O—C$_{1-6}$alkyl or arylC$_{1-6}$alkyl-O—C$_{1-6}$alkyl; or R$^3$ is aryl.

An eighth interesting embodiment relates to a compound of formula (Ia) or (Ib) or any subgroup thereof as mentioned hereinbefore as interesting embodiment wherein q is equal to 1, 3 or 4.

A ninth interesting embodiment relates to a compound of formula (Ia) or (Ib) or any subgroup thereof as mentioned hereinbefore as interesting embodiment wherein $R^4$ and $R^5$ each independently represent hydrogen or $C_{1-6}$alkyl, in particular $C_{1-6}$alkyl, more in particular methyl or ethyl. Preferably $R^4$ and $R^5$ are methyl.

A tenth interesting embodiment relates to a compound of formula (Ia) or (Ib) or any subgroup thereof as mentioned hereinbefore as interesting embodiment wherein $R^4$ and $R^5$ together with the nitrogen atom to which they are attached form a radical selected from the group consisting of piperidino, piperazino, morpholino, imidazolyl, triazolyl, each of said rings optionally substituted with $C_{1-6}$alkyl; more in particular piperidino, piperazino or morpholino, each of said rings optionally substituted with $C_{1-4}$alkyl; even more in particular piperidino or piperazino optionally substituted with $C_{1-4}$alkyl.

An eleventh interesting embodiment relates to a compound of formula (Ia) or (Ib) or any subgroup thereof as mentioned hereinbefore as interesting embodiment wherein $R^6$ is Het or optionally substituted phenyl; in particular Het, or phenyl optionally substituted with halo, cyano, Het or $C_{1-6}$alkyloxy; more in particular Het, or phenyl optionally substituted with halo or Het wherein Het represents preferably pyridyl, thienyl, furanyl, quinolinyl or pyrazolyl, each of said rings representing Het optionally being substituted with $C_{1-6}$alkyl; even more in particular benzo[1,3]dioxolyl, or phenyl optionally substituted with halo or Het wherein Het represents preferably pyridyl, thienyl, furanyl, quinolinyl or pyrazolyl, each of said rings representing Het optionally being substituted with $C_{1-6}$alkyl.

A twelfth interesting embodiment relates to a compound of formula (Ia) or (Ib) or any subgroup thereof as mentioned hereinbefore as interesting embodiment wherein $R^7$ is hydrogen.

A thirteenth interesting embodiment relates to a compound of formula (Ia) or (Ib) or any subgroup thereof as mentioned hereinbefore as interesting embodiment wherein the compound is a compound of formula (Ia).

A fourteenth interesting embodiment relates to a compound of formula (Ia) or (Ib) or any subgroup thereof as mentioned hereinbefore as interesting embodiment wherein the compound is a compound of formula (Ib) and wherein $R^8$ is hydrogen and $R^9$ is oxo.

A fifteenth interesting embodiment relates to a compound of formula (Ia) or (Ib) or any subgroup thereof as mentioned hereinbefore as interesting embodiment wherein the compound is a compound of formula (Ib), in particular wherein $R^8$ is alkyl, more preferable $C_{1-6}$alkyl, e.g. methyl.

A sixteenth interesting embodiment is a compound of formula (Ia) or (Ib) or any subgroup thereof as mentioned hereinbefore as interesting embodiment wherein aryl is naphthyl or phenyl, more preferably phenyl, each optionally substituted with one or two substituents selected from halo, for example chloro; cyano; alkyl for example methyl; or alkyloxy, for example methyloxy; or Het, for example pyridyl, thienyl, furanyl, quinolinyl or imidazolyl, each of said rings representing Het optionally being substituted with $C_{1-6}$alkyl.

A seventeenth interesting embodiment relates to a compound of formula (Ia) or (Ib) or any subgroup thereof as mentioned hereinbefore as interesting embodiment wherein $R^1$ is placed in position 6 of the quinoline ring.

In the framework of this application, the quinoline ring of the compounds of formula (Ia) or (Ib) is numbered as follows:

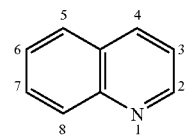

An eighteenth interesting embodiment is the use of a compound of formula (Ia) or (Ib) or any subgroup thereof as mentioned hereinbefore as interesting embodiment for the manufacture of a medicament for the treatment of a bacterial infection with a gram-positive and/or a gram-negative bacterium, preferably a bacterial infection with a gram-positive bacterium.

A nineteenth interesting embodiment is the use of a compound of formula (Ia) or (Ib) or any subgroup thereof as mentioned hereinbefore as interesting embodiment for the manufacture of a medicament for the treatment of a bacterial infection wherein the compound of formula (Ia) or (Ib) has a $IC_{90}<15$ µl/ml against at least one bacterium, in particular a gram-positive bacterium; preferably a $IC_{90}<10$ µl/ml; more preferably a $IC_{90}<5$ µl/ml; the $IC_{90}$ value being determined as described hereinafter.

A twentieth interesting embodiment relates to a compound of formula (Ia) or any subgroup thereof as mentioned hereinbefore as interesting embodiment wherein one or more, preferably all, of the following definitions apply:

$R^1$ is hydrogen or halo; in particular hydrogen or bromo;
$R^2$ is alkyloxy, in particular $C_{1-6}$alkyloxy; more in particular methyloxy;
$R^3$ is aryl-O—$C_{1-6}$alkyl, aryl$C_{1-6}$alkyl-O—$C_{1-6}$alkyl, aryl, or aryl-aryl;
$R^4$ and $R^5$ are $C_{1-6}$alkyl; in particular methyl; or $R^4$ and $R^5$ together with the nitrogen atom to which they are attached form a radical selected from the group consisting of piperidino or piperazino, each of said rings optionally substituted with $C_{1-6}$alkyl;
$R^6$ is Het or optionally substituted phenyl; in particular Het, or phenyl optionally substituted with halo or Het; more in particular benzo[1,3]dioxolyl, furanyl, or phenyl optionally substituted with halo or Het wherein Het represents pyridyl, thienyl, furanyl, quinolinyl or pyrazolyl, each of said rings representing Het optionally being substituted with $C_{1-6}$alkyl;
$R^7$ is hydrogen;
q is 1, 3 or 4;
p is 1.

Preferably, in the compounds of formula (Ia) and (Ib) or any subgroup thereof as mentioned hereinbefore as interesting embodiment, the term "alkyl" represents $C_{1-6}$alkyl, more preferably $C_{1-4}$alkyl, and the term haloalkyl represents polyhalo$C_{1-6}$alkyl.

Preferably, the compound of formula (Ia) or (Ib) is a particular mixture of enantiomers (hereinafter indicated as a particular A or B diastereoisomer) and hence is substantially free of the other diastereoisomer(s). In case the compound of formula (Ia) or (Ib) has two chiral centers this means that the compound is a mixture, in particular a racemic mixture, of the (R,S) and (S,R) enantiomers or a mixture, in particular a racemic mixture, of the (R,R) and (S,S) enantiomer. Hereinafter, the mixtures, in particular the racemic mixtures, of 2 enantiomers are indicated as diastereoisomer A or B. Whether the racemic mixture is indicated as A or B depends on whether it is first isolated in the synthesis protocol (i.e. A) or second (i.e. B). More preferably, the compound of formula (Ia) or (Ib) is a particular enantiomer (substantially free of the other enantiomers). In case the compound of formula (Ia) or (Ib)

has two chiral centers this means that the compound is the (R,S), (S,R), (R,R) or (S,S) enantiomer. Hereinafter, said particular enantiomers are indicated as A1, A2, B1 or B2. Whether the enantiomer is indicated as A1, A2, B1 or B2 depends on whether it is isolated first or second (1 or 2) in the synthesis protocol and whether it is separated from the A (A1, A2) or B (B1, B2) diastereoisomer.

Preferred compounds of the present invention are selected from

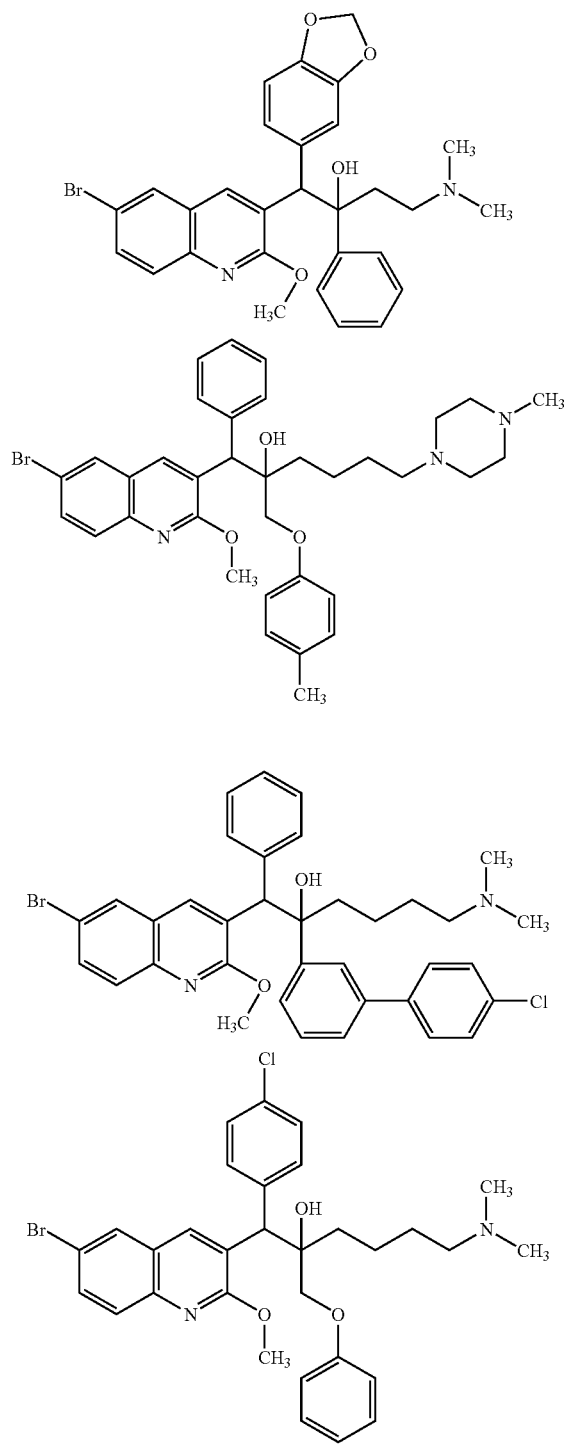

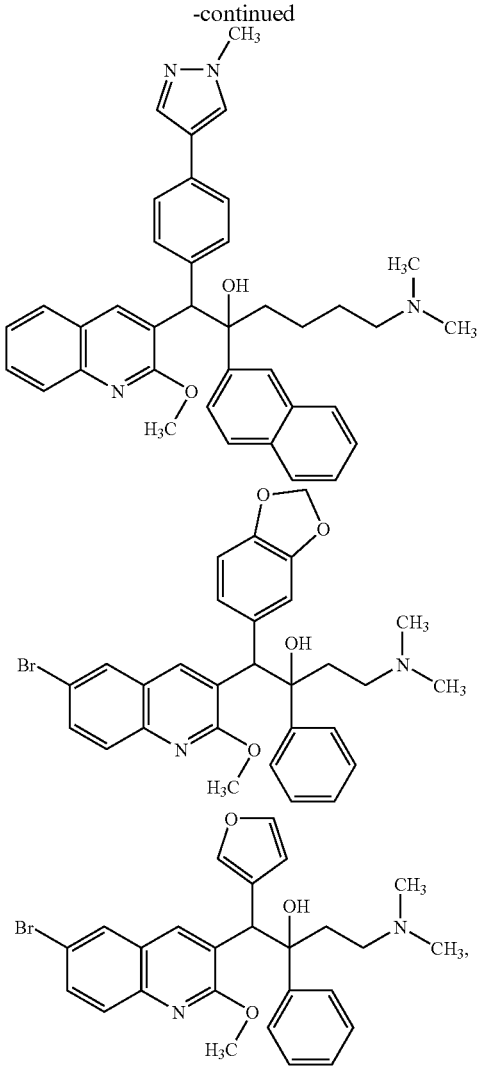

including any stereochemically isomeric form thereof, a N-oxide thereof, a pharmaceutically acceptable salt thereof or a solvate thereof.

In particular preferred compounds of formula (Ia) or (Ib) are compounds 7, 9, 10 and 29 (see Tables hereinafter); a pharmaceutically acceptable salt thereof, a solvate thereof or a N-oxide form thereof, or compounds 29, 23, 34, 11, 4, 52, and 30 (see Tables hereinafter); a pharmaceutically acceptable salt thereof, a solvate thereof or a N-oxide form thereof.

Pharmacology

The compounds according to the invention have surprisingly been shown to be suitable for the treatment of a bacterial infection including a mycobacterial infection, particularly those diseases caused by pathogenic mycobacteria such as *Mycobacterium tuberculosis* (including the latent and drug resistant form thereof), *M. bovis, M. leprae, M. avium, M. leprae* and *M. marinum*. The present invention thus also relates to compounds of formula (Ia) or (Ib) as defined hereinabove, the pharmaceutically acceptable salts thereof, the solvates thereof or the N-oxide forms thereof, for use as a medicine, in particular for use as a medicine for the treatment of a bacterial infection including a mycobacterial infection.

Further, the present invention also relates to the use of a compound of formula (Ia) or (Ib), the pharmaceutically acceptable salts thereof, the solvates thereof or the N-oxide forms thereof, as well as any of the pharmaceutical compositions thereof as described hereinafter for the manufacture of a medicament for the treatment of a bacterial infection including a mycobacterial infection.

Accordingly, in another aspect, the invention provides a method of treating a patient suffering from, or at risk of, a bacterial infection, including a mycobacterial infection, which comprises administering to the patient a therapeutically effective amount of a compound or pharmaceutical composition according to the invention.

In addition to their activity against mycobacteria, the compounds according to the invention are also active against other bacteria. In general, bacterial pathogens may be classified as either gram-positive or gram-negative pathogens. Antibiotic compounds with activity against both gram-positive and gram-negative pathogens are generally regarded as having a broad spectrum of activity. The compounds of the present invention are regarded as active against gram-positive and/or gram-negative bacterial pathogens, in particular against gram-positive bacterial pathogens. In particular, the present compounds are active against at least one gram-positive bacterium, preferably against several gram-positive bacteria, more preferably against one or more gram-positive bacteria and/or one or more gram-negative bacteria.

The present compounds have bactericidal or bacteriostatic activity.

Examples of gram-positive and gram-negative aerobic and anaerobic bacteria, include Staphylococci, for example *S. aureus*; Enterococci, for example *E. faecalis*; Streptococci, for example *S. pneumoniae, S. mutans, S. pyogenes*; Bacilli, for example *Bacillus subtilis; Listeria*, for example *Listeria monocytogenes; Haemophilus*, for example *H. influenza; Moraxella*, for example *M. catarrhalis; Pseudomonas*, for example *Pseudomonas aeruginosa*; and *Escherichia*, for example *E. coli*. Gram-positive pathogens, for example Staphylococci, Enterococci and Streptococci are particularly important because of the development of resistant strains which are both difficult to treat and difficult to eradicate from for example a hospital environment once established. Examples of such strains are methicillin resistant *Staphylococcus aureus* (MRSA), methicillin resistant coagulase negative staphylococci (MRCNS), penicillin resistant *Streptococcus pneumoniae* and multiple resistant *Enterococcus faecium*.

The compounds of the present invention also show activity against resistant bacterial strains.

The compounds of the present invention are especially active against *Streptococcus pneumoniae* and *Staphylococcus aureus*, including resistant *Staphylococcus aureus* such as for example methicillin resistant *Staphylococcus aureus* (MRSA).

Therefore, the present invention also relates to the use of a compound of formula (Ia) or (Ib), the pharmaceutically acceptable salts thereof, the solvates thereof or the N-oxide forms thereof, as well as any of the pharmaceutical compositions thereof as described hereinafter for the manufacture of a medicament for the treatment of a bacterial infection including an infection caused by Staphylococci and/or Streptococci.

Accordingly, in another aspect, the invention provides a method of treating a patient suffering from, or at risk of, a bacterial infection, including an infection caused by Staphylococci and/or Streptococci, which comprises administering to the patient a therapeutically effective amount of a compound or pharmaceutical composition according to the invention.

Without being bound to any theory, it is taught that the activity of the present compounds lies in inhibition of the F1F0 ATP synthase, in particular the inhibition of the F0 complex of the F1F0 ATP synthase, more in particular the inhibition of subunit c of the F0 complex of the F1F0 ATP synthase, leading to killing of the bacteria by depletion of the cellular ATP levels of the bacteria. Therefore, in particular, the compounds of the present invention are active on those bacteria of which the viability depends on proper functioning of F1F0 ATP synthase.

Bacterial infections which may be treated by the present compounds include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients.

Whenever used hereinbefore or hereinafter, that the compounds can treat a bacterial infection it is meant that the compounds can treat an infection with one or more bacterial strains.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight, even more preferably from 0.1 to 50% by weight of the active ingredient(s), and, from 1 to 99.95% by weight, more preferably from 30 to 99.9% by weight, even more preferably from 50 to 99.9% by weight of a pharmaceutically acceptable carrier, all percentages being based on the total weight of the composition.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will, of course, vary with the compound employed, the mode of administration, the treatment desired and the mycobacterial disease indicated. However, in general, satisfactory results will be obtained when the compound according to the invention is administered at a daily dosage not exceeding 1 gram, e.g. in the range from 10 to 50 mg/kg body weight.

Given the fact that the compounds of formula (Ia) or Formula (Ib) are active against bacterial infections, the present compounds may be combined with other antibacterial agents in order to effectively combat bacterial infections.

Therefore, the present invention also relates to a combination of (a) a compound according to the invention, and (b) one or more other antibacterial agents.

The present invention also relates to a combination of (a) a compound according to the invention, and (b) one or more other antibacterial agents, for use as a medicine.

The present invention also relates to the use of a combination or pharmaceutical composition as defined directly above for the treatment of a bacterial infection.

A pharmaceutical composition comprising a pharmaceutically acceptable carrier and, as active ingredient, a therapeutically effective amount of (a) a compound according to the invention, and (b) one or more other antibacterial agents, is also comprised by the present invention.

The weight ratio of (a) the compound according to the invention and (b) the other antibacterial agent(s) when given as a combination may be determined by the person skilled in the art. Said ratio and the exact dosage and frequency of administration depends on the particular compound according to the invention and the other antibacterial agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (Ia) or (Ib) and another antibacterial agent may range from 1/10 to 10/1, more in particular from 1/5 to 5/1, even more in particular from 1/3 to 3/1.

The compounds according to the invention and the one or more other antibacterial agents may be combined in a single preparation or they may be formulated in separate preparations so that they can be administered simultaneously, separately or sequentially. Thus, the present invention also relates to a product containing (a) a compound according to the invention, and (b) one or more other antibacterial agents, as a combined preparation for simultaneous, separate or sequential use in the treatment of a bacterial infection.

The other antibacterial agents which may be combined with the compounds of formula (Ia) or (Ib) are for example antibacterial agents known in the art. The other antibacterial agents comprise antibiotics of the α-lactam group such as natural penicillins, semisynthetic penicillins, natural cephalosporins, semisynthetic cephalosporins, cephamycins, 1-oxacephems, clavulanic acids, penems, carbapenems, nocardicins, monobactams; tetracyclines, anhydrotetracyclines, anthracyclines; aminoglycosides; nucleosides such as N-nucleosides, C-nucleosides, carbocyclic nucleosides, blasticidin S; macrolides such as 12-membered ring macrolides, 14-membered ring macrolides, 16-membered ring macrolides; ansamycins; peptides such as bleomycins, gramicidins, polymyxins, bacitracins, large ring peptide antibiotics containing lactone linkages, actinomycins, amphomycin, capreomycin, distamycin, enduracidins, mikamycin, neocarzinostatin, stendomycin, viomycin, virginiamycin; cycloheximide; cycloserine; variotin; sarkomycin A; novobiocin; griseofulvin; chloramphenicol; mitomycins; fumagillin; monensins; pyrrolnitrin; fosfomycin; fusidic acid; D-(p-hydroxyphenyl)glycine; D-phenylglycine; enediynes.

Specific antibiotics which may be combined with the present compounds of formula (Ia) or (Ib) are for example benzylpenicillin (potassium, procaine, benzathine), phenoxymethylpenicillin (potassium), phenethicillin potassium, propicillin, carbenicillin (disodium, phenyl sodium, indanyl sodium), sulbenicillin, ticarcillin disodium, methicillin sodium, oxacillin sodium, cloxacillin sodium, dicloxacillin, flucloxacillin, ampicillin, mezlocillin, piperacillin sodium, amoxicillin, ciclacillin, hectacillin, sulbactam sodium, talampicillin hydrochloride, bacampicillin hydrochloride, pivmecillinam, cephalexin, cefaclor, cephaloglycin, cefadroxil, cephradine, cefroxadine, cephapirin sodium, cephalothin sodium, cephacetrile sodium, cefsulodin sodium, cephaloridine, cefatrizine, cefoperazone sodium, cefamandole, vefotiam hydrochloride, cefazolin sodium, ceftizoxime sodium, cefotaxime sodium, cefmenoxime hydrochloride, cefuroxime, ceftriaxone sodium, ceftazidime, cefoxitin, cefmetazole, cefotetan, latamoxef, clavulanic acid, imipenem, aztreonam, tetracycline, chlortetracycline hydrochloride, demethylchlortetracycline, oxytetracycline, methacycline, doxycycline, rolitetracycline, minocycline, daunorubicin hydrochloride, doxorubicin, aclarubicin, kanamycin sulfate, bekanamycin, tobramycin, gentamycin sulfate, dibekacin, amikacin, micronomicin, ribostamycin, neomycin sulfate, paromomycin sulfate, streptomycin sulfate, dihydrostreptomycin, destomycin A, hygromycin B, apramycin, sisomicin, netilmicin sulfate, spectinomycin hydrochloride, astromicin sulfate, validamycin, kasugamycin, polyoxin, blasticidin S, erythromycin, erythromycin estolate, oleandomycin phosphate, tracetyloleandomycin, kitasamycin, josamycin, spiramycin, tylosin, ivermectin, midecamycin, bleomycin sulfate, peplomycin sulfate, gramicidin S, polymyxin B, bacitracin, colistin sulfate, colistinmethanesulfonate sodium, enramycin, mikamycin, virginiamycin, capreomycin sulfate, viomycin, enviomycin, vancomycin, actinomycin D, neocarzinostatin, bestatin, pepstatin, monensin, lasalocid, salinomycin, amphotericin B, nystatin, natamycin, trichomycin, mithramycin, lincomycin, clindamycin, clindamycin palmitate hydrochloride, flavophospholipol, cycloserine, pecilocin, griseofulvin, chloramphenicol, chloramphenicol palmitate, mitomycin C, pyrrolnitrin, fosfomycin, fusidic acid, bicozamycin, tiamulin, siccanin.

Other Mycobacterial agents which may be combined with the compounds of formula (Ia) or (Ib) are for example rifampicin (=rifampin); isoniazid; pyrazinamide; amikacin; ethionamide; ethambutol; streptomycin; para-aminosalicylic acid; cycloserine; capreomycin; kanamycin; thioacetazone; PA-824; quinolones/fluoroquinolones such as for example moxifloxacin, gatifloxacin, ofloxacin, ciprofloxacin, sparfloxacin; macrolides such as for example clarithromycin, clofazimine, amoxycillin with clavulanic acid; rifamycins; rifabutin; rifapentine; the compounds disclosed in WO2004/011436.

General Preparation

The compounds according to the invention can generally be prepared by a succession of steps, each of which is known to the skilled person.

The starting materials and the intermediates are compounds that are either commercially available or may be prepared according to conventional reaction procedures generally known in the art. For example, the compounds of formula (Ia) or (Ib) can be prepared according to the methods described in WO 2004/011436, WO2005/070924, WO2005/070430 or WO2005/075428, the contents of which are incorporated herein by reference.

In particular, the compounds of formula (Ia) or (Ib) can be prepared by reacting an intermediate of formula (IIa) or (IIb) with an intermediate of formula (III) according to the following reaction scheme (1):

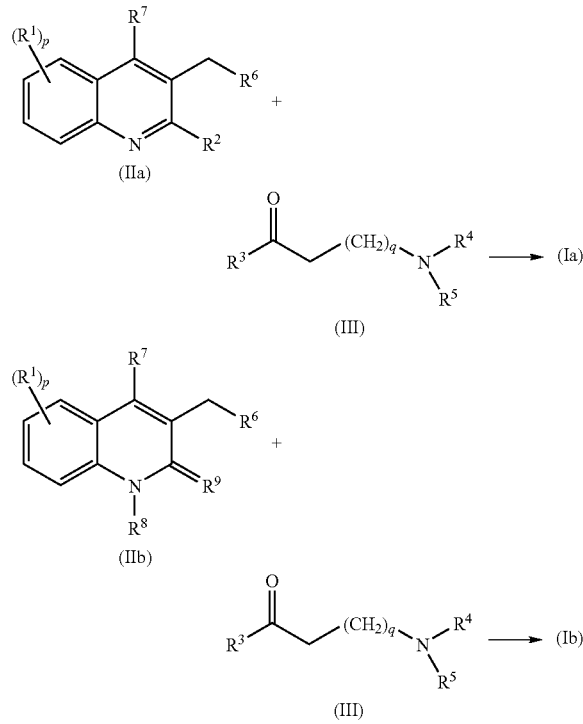

using nBuLi in a mixture of a suitable base, such as for example diisopropyl amine, and a suitable solvent, such as for example tetrahydrofuran, wherein all variables are defined as in formula (Ia) or (Ib). Stirring may enhance the rate of the reaction. The reaction may conveniently be carried out at a temperature ranging between −20 and −70° C.

Compounds of formula (Ia) or (Ib) wherein $R^6$ represents phenyl substituted with Het, and wherein $R^3$ represents alkyl, arylalkyl, aryl, Het, Het-alkyl or

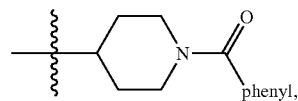

said $R^3$ being represented by $R^{3'}$ and said compounds being represented by formula (Ia-1) or (Ib-1), can be prepared by reacting an intermediate of formula (IV-a) or (IV-b) wherein $W^1$ represents a suitable leaving group, such as for example halo, e.g. chloro or bromo, with Het-B(OH)$_2$ in the presence of a suitable catalyst, such as for example Pd(PPh$_3$)$_4$, in the presence of a suitable base, such as for example Na$_2$CO$_3$, and a suitable solvent, such as for example toluene or 1,2-dimethoxyethane (DME) and an alcohol, for example methanol according to the following reaction scheme (2):

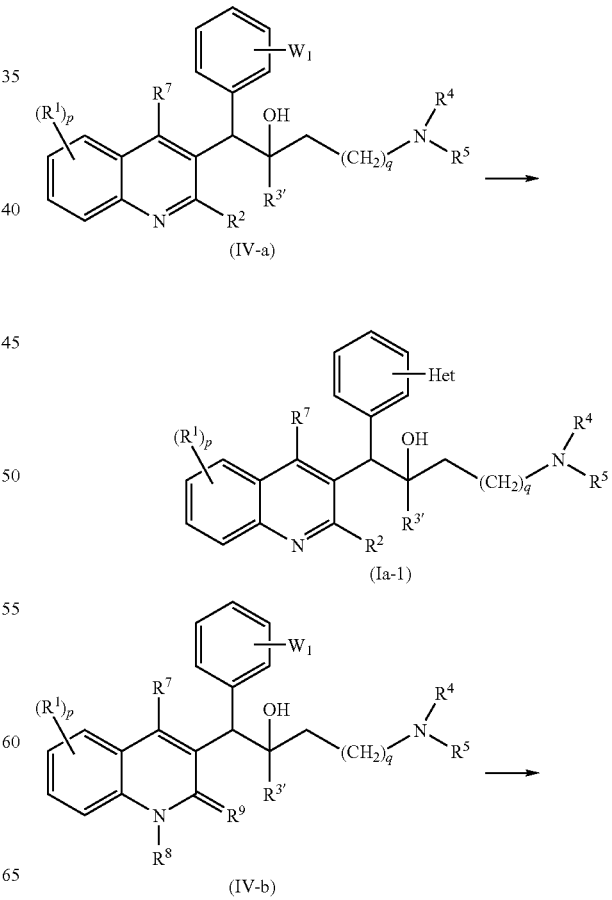

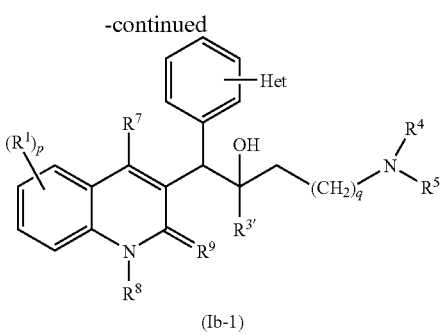

(Ib-1)

Compounds of formula (Ia) or (b) wherein q is equal to 2, 3 or 4, said compounds being represented by formula (Ia-2) or (Ib-2), can be prepared by reacting an intermediate of formula (V-a) or (V-b) wherein q' is 0, 1 or 2, with a primary or secondary amine $HNR^4R^5$ in the presence of a suitable catalyst, such as for example $Rh(cod)_2BF_4$, optionally in the presence of a second catalyst (for the reduction), such as for example $Ir(cod)_2BF_4$, in the presence of a suitable ligand, such as for example Xantphos, in a suitable solvent, such as for example tetrahydrofuran and an alcohol, e.g. methanol, in the presence of CO and $H_2$ (under pressure) at elevated temperature. This reaction is preferably done for intermediates of formula (V) wherein q' is 1.

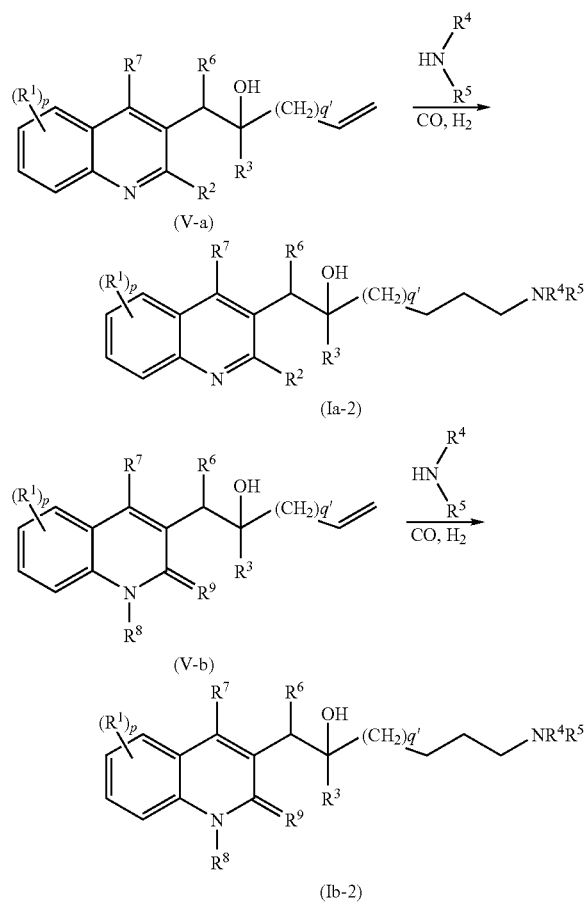

Compounds of formula (Ia) or (Ib) can also be prepared by reacting an intermediate of formula (VI-a) or (VI-b) wherein $W_2$ represents a suitable leaving group, such as for example halo, e.g. chloro or bromo, with a suitable primary or secondary amine $HNR^4R^5$, optionally in the presence of a suitable solvent, such as for example acetonitrile.

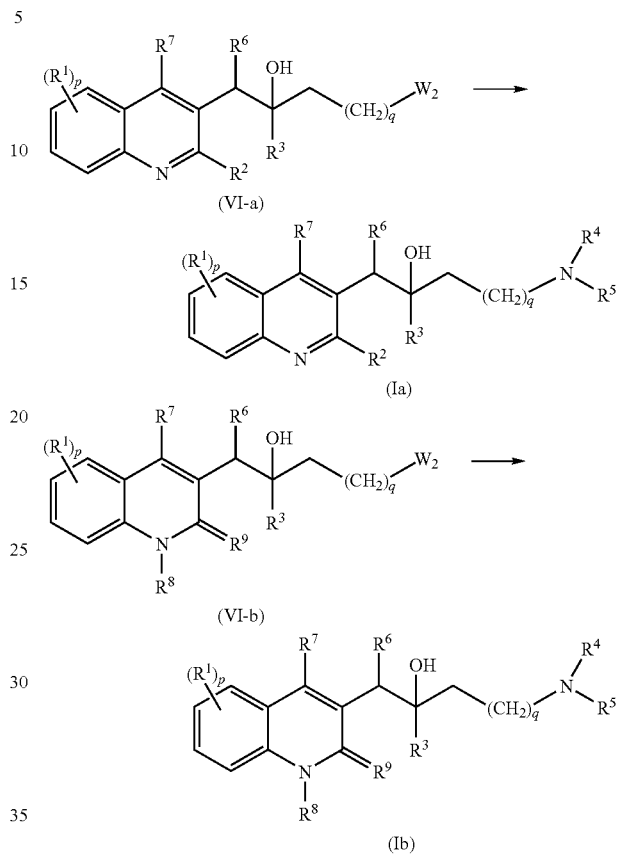

It is considered within the knowledge of the skilled man to explore the appropriate temperatures, dilutions, and reaction times in order to optimize the above reactions in order to obtain a desired compound.

The compounds of formula (Ia) or (Ib) may further be prepared by converting compounds of formula (Ia) or (Ib) into each other according to art-known group transformation reactions.

The compounds of formula (Ia) or (Ib) may be converted to the corresponding N-oxide forms following art-known procedures for converting a trivalent nitrogen into its N-oxide form. Said N-oxidation reaction may generally be carried out by reacting the starting material of formula (Ia) or (Ib) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (Ia) or (Ib) wherein $R^1$ represents halo, e.g. bromo, can be converted into a compound of formula (Ia) or (Ib) wherein $R^1$ represents Het, by reaction with Het-B(OH)$_2$ in the presence of a suitable catalyst, such as for example Pd(OAc)$_2$ or Pd(PPh$_3$)$_4$, in the presence of a suitable base, such as for example K$_3$PO$_4$ or Na$_2$CO$_3$, and a suitable solvent, such as for example toluene or 1,2-dimethoxyethane (DME).

Similarly, compounds of formula (Ia) or (Ib) in which R$^1$ is halo, for example bromo, may be converted into compounds of formula (Ia) or (Ib) in which R$^1$ is alkyl, for example methyl, by treatment with an appropriate alkylating agent such as CH$_3$B(OH)$_2$ or (CH$_3$)$_4$Sn in the presence of a suitable catalyst, such as for example Pd(PPh$_3$)$_4$, in a suitable solvent such as for example toluene or 1,2-dimethoxyethane (DME).

Compounds of formula (Ia) or (Ib) wherein R$^1$ is halo, in particular bromo, can be converted into a compound of formula (Ia) or (Ib) wherein R$^1$ is hydrogen, by reaction with HCOONH$_4$ in the presence of a suitable catalyst such as for example palladium on charcoal, and in the presence of a suitable solvent, such as for example an alcohol, e.g. methanol. The same reaction conditions can be used to convert a compound of formula (Ia) or (Ib) wherein R$^4$ is benzyl into a compound of formula (Ia) or (Ib) wherein R$^4$ is hydrogen.

Compounds of formula (Ia) or (Ib) wherein R$^6$ represents phenyl substituted with halo, can be converted into a compound of formula (Ia) or (Ib) wherein R$^6$ represents phenyl substituted with Het, by reaction with Het-B(OH)$_2$ in the presence of a suitable catalyst, such as for example Pd (PPh$_3$)$_4$, in the presence of a suitable base, such as for example Na$_2$CO$_3$, and a suitable solvent, such as for example toluene or 1,2-dimethoxyethane (DME) and an alcohol, for example methanol.

A compound of formula (Ia) wherein R$^2$ represents methoxy, can be converted into the corresponding compound of formula (Ib) wherein R$^8$ is hydrogen and R$^9$ is oxo, by hydrolysis in the presence of a suitable acid, such as for example hydrochloric acid, and a suitable solvent, such as for example dioxane.

Compounds of formula (Ia) or (Ib) can also be converted into a quaternary amine by reaction with a suitable quaternizing agent, such as, for example, an optionally substituted C$_{1-6}$alkylhalide, arylC$_{1-6}$alkylhalide, C$_{1-6}$alkylcarbonylhalide, arylcarbonylhalide, Het$^1$C$_{1-6}$alkylhalide or Het$^1$carbonylhalide, e.g. methyliodide or benzyliodide, in the presence of a suitable solvent, such as for example acetone wherein Het$^1$ represents furanyl or thienyl; or a bicyclic heterocycle selected from benzofuranyl or benzothienyl; each monocyclic and bicyclic heterocycle may optionally be substituted with 1, 2 or 3 substituents, each substituent independently selected from the group of halo, C$_{1-6}$alkyl and aryl.

Said quaternary amines are represented by the below formula wherein R$^{10}$ represents C$_{1-6}$alkyl, C$_{1-6}$alkylcarbonyl, arylC$_{1-6}$ alkyl, arylcarbonyl, Het$^1$C$_{1-6}$alkyl or Het$^1$carbonyl and wherein A$^-$ represents a pharmaceutically acceptable counterion, such as for example iodide.

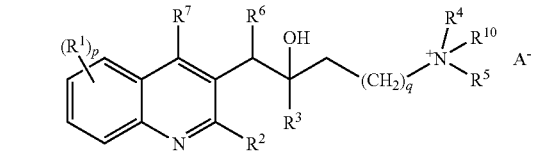

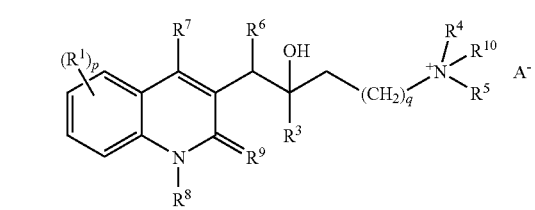

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC, chiral chromatography. Individual diastereoisomers or individual enantiomers can also be obtained by Supercritical Fluid Chromatography (SCF).

The starting materials and the intermediates are compounds that are either commercially available or may be prepared according to conventional reaction procedures generally known in the art. For example, the intermediates of formula (II-a) or (II b) or (III) can be prepared according to the methods described in WO2004/011436, WO2005/070924, WO2005/070430 or WO2005/075428, the contents of which are incorporated herein by reference.

In particular, the intermediates of formula (IIa) may be prepared according to the following reaction scheme (3):

Scheme 3

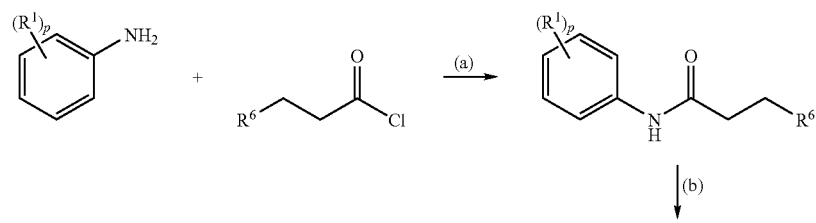

-continued

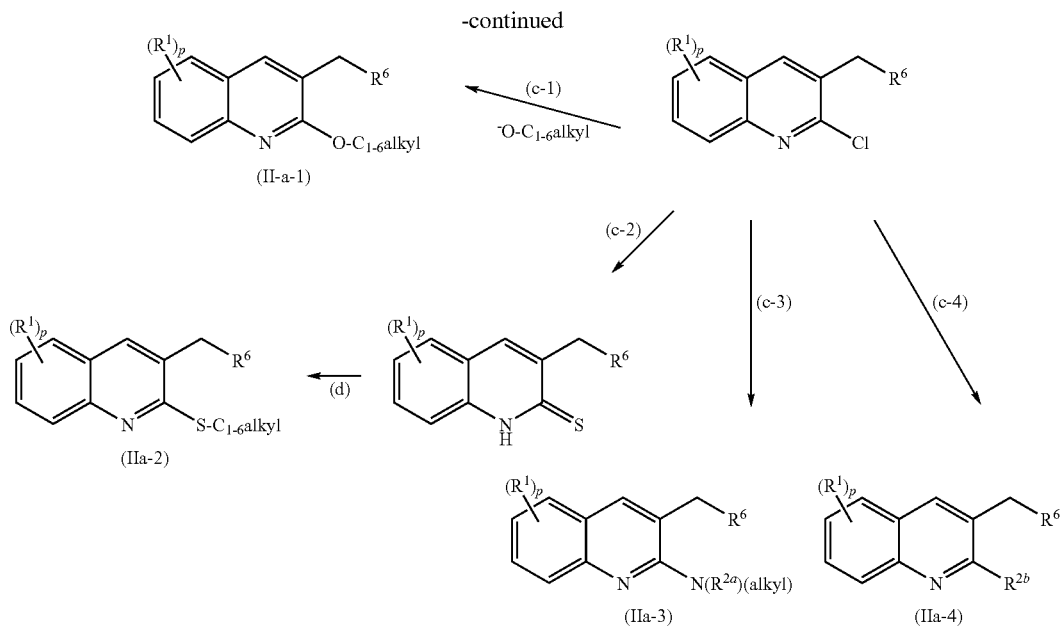

wherein all variables are defined as in formula (Ia). Reaction scheme (3) comprises step (a) in which an appropriately substituted aniline is reacted with an appropriate acylchloride such as for example 3-phenylpropionyl chloride, 3-fluorobenzenepropionyl chloride or p-chlorobenzenepropionyl chloride, in the presence of a suitable base, such as triethylamine, and a suitable reaction-inert solvent, such as methylene chloride or ethylene dichloride. The reaction may conveniently be carried out at a temperature ranging between room temperature and reflux temperature. In a next step (b) the adduct obtained in step (a) is reacted with phosphoryl chloride ($POCl_3$) in the presence of N,N-dimethylformamide (Vilsmeier-Haack formylation followed by cyclization). The reaction may conveniently be carried out at a temperature ranging between room temperature and reflux temperature. In a next step (c-1), a specific $R^2$-group, wherein $R^2$ is for example a $C_{1-6}$alkyloxy radical is introduced by reacting the intermediate compound obtained in step (b) with $^-O\text{---}C_{1-6}$alkyl in the presence of a suitable solvent, such as for example $HO\text{---}C_{1-6}$alkyl. The intermediate obtained in step (b) can also be converted into an intermediate wherein $R^2$ is for example a $C_{1-6}$alkylthio radical by reaction with $S=C(NH_2)_2$ in the presence of a suitable solvent, such as for example an alcohol, e.g. ethanol, or an alcohol/water mixture, optionally in the presence of a suitable base, such as for example KOH, (see step (c-2)) followed by reaction with $C_{1-6}$alkyl-I in the presence of a suitable base, such as for example $K_2CO_3$ and a suitable solvent, such as for example 2-propanone (see step (d)). The intermediate obtained in step (b) can also be converted into an intermediate wherein $R^2$ is —$N(R^{2a})$(alkyl) wherein $R^{2a}$ is hydrogen or alkyl, by reaction with a suitable salt of $NH(R^{2a})$(alkyl) in the presence of a suitable base, such as for example potassium carbonate, and a suitable solvent, such as for example acetonitrile (step (c-3)). The intermediate obtained in step (b) can also be converted into an intermediate wherein $R^2$ is $C_{1-6}$alkyloxy$C_{1-6}$ alkyloxy optionally substituted with $C_{1-6}$alkyloxy, said $R^2$ being represented by $R^{2b}$, by reaction with $C_{1-6}$alkyloxy$C_{1-6}$yalkylOH optionally substituted with $C_{1-6}$alkyloxy, in the presence of NaH and a suitable solvent, such as for example tetrahydrofuran (step (c-4)).

Intermediates of formula (IIa) wherein $R^2$ and $R^7$ represent hydrogen, said intermediates being represented by formula (IIa-5), may be prepared according to the following reaction scheme (4), wherein in a first step (a) a substituted indole-2,3-dione is reacted with an optionally substituted 3-phenylpropionaldehyde in the presence of a suitable base such as sodium hydroxide (Pfitzinger reaction), after which the carboxylic acid compound is decarboxylated in a next step (b) at high temperature in the presence of a suitable reaction-inert solvent such as diphenylether.

Scheme 4

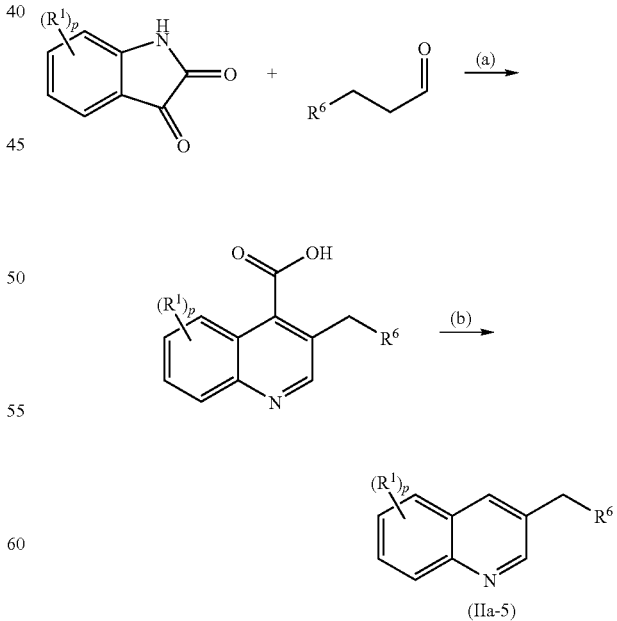

Intermediates of formula (IIa) wherein $R^6$ represents Het, said intermediates being represented by formula (IIa-6), can be prepared according to the following reaction scheme 4a.

Scheme 4a

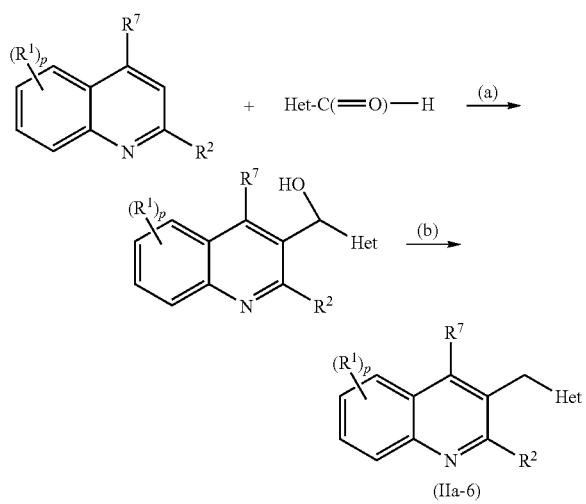

Reaction scheme (4a) comprises step (a) in which an appropriate quinoline moiety is reacted with Het-C(=O)—H using nBuLi in a mixture of a suitable base, such as for example 2,2,6,6-tetramethylpiperidine, and a suitable solvent, such as for example tetrahydrofuran. Stirring may enhance the rate of the reaction. The reaction may conveniently be carried out at a temperature ranging between –20 and –70° C. In a next step (b), the product obtained in step (a) is converted in an intermediate of formula (IIa-6) by reaction with a suitable acid, such as for example trifluoroacetic acid, and triisopropylsilane, in the presence of a suitable solvent, such as for example methylene chloride.

Intermediates of formula (IIb), in particular (IIb-1) or (IIb-2), can be prepared according to the following reaction scheme (5).

Scheme 5

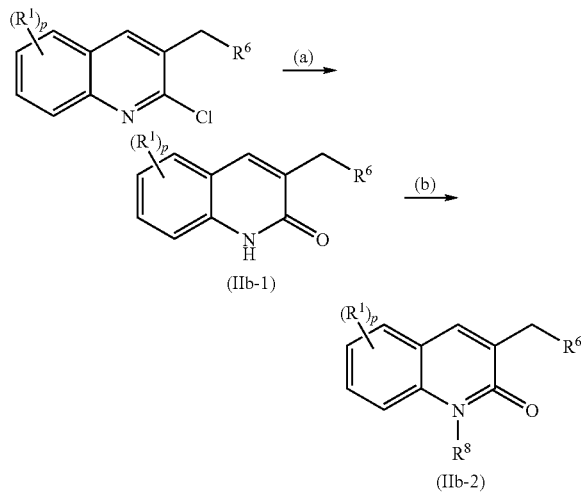

Reaction scheme (5) comprises step (a) in which the quinoline moiety is converted in the quinolinone moiety by reaction with a suitable acid, such as for example hydrochloric acid. In a next step (b), a $R^8$ substituent is introduced by reacting the intermediate obtained in step (a) with a suitable alkylating agent, such as for example alkyliodide, e.g. methyliodide, in the presence of a suitable base, such as for example NaOH or benzyltriethylammonium chloride, a suitable solvent, such as for example tetrahydrofuran.

Intermediates of formula (IIb) wherein $R^8$ and $R^9$ are taken together to form the radical —CH=CH—N=, said intermediates being represented by formula (IIb-3), can be prepared according to the following reaction scheme (6).

Scheme 6

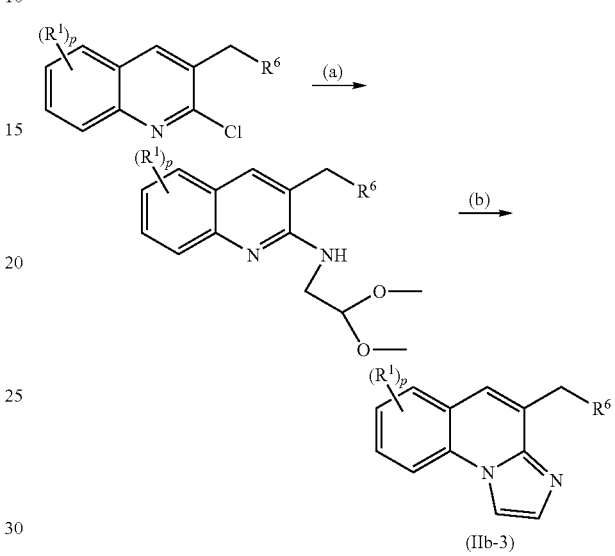

Reaction scheme (6) comprises step (a) in which the intermediate is reacted with $NH_2$—$CH_2$—$CH(OCH_3)_2$. In a next step (b), the fused imidazolyl moiety is formed by reaction with acetic acid in the presence of a suitable solvent, such as for example xylene.

The intermediates of formula (III) are compounds that are either commercially available or may be prepared according to conventional reaction procedures generally known in the art. For example, intermediates of formula (III) may be prepared according to the following reaction scheme (7):

Scheme 7

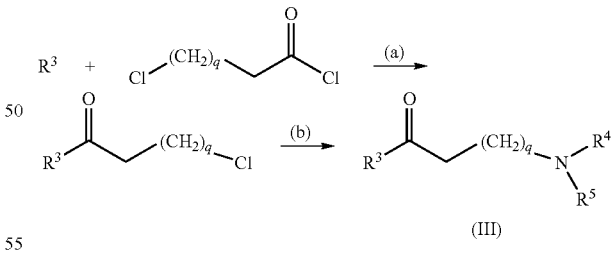

Reaction scheme (7) comprises step (a) in which $R^3$, in particular an appropriately substituted aryl, more in particular an appropriately substituted phenyl, is reacted by Friedel-Craft reaction with an appropriate acylchloride such as 3-chloropropionyl chloride or 4-chlorobutyryl chloride, in the presence of a suitable Lewis acid, such as for example $AlCl_3$, $FeCl_3$, $SnCl_4$, $TiCl_4$ or $ZnCl_2$ and a suitable reaction-inert solvent, such as methylene chloride or ethylene dichloride. The reaction may conveniently be carried out at a temperature ranging between room temperature and reflux temperature. In a next step (b), an amino group (—$NR^4R^5$) is introduced by reacting the intermediate obtained in step (a) with a primary or secondary amine (HNR⁴R⁵).

The intermediates of formula (III) may also be prepared according to the following reaction Scheme (7a):

Scheme 7a

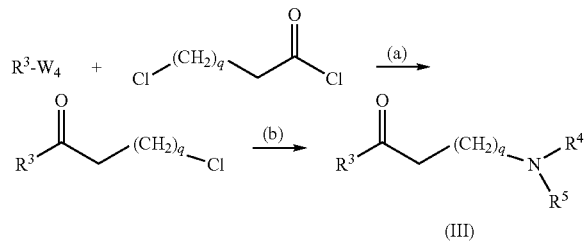

(III)

Reaction scheme (7a) comprises step (a) in which R³—W₄, wherein W₄ represents a suitable leaving group, such as for example halo, e.g. chloro or bromo, in particular an appropriately substituted aryl, more in particular an appropriately substituted naphthyl, e.g. 2-bromo-naphthalene, is reacted with an appropriate acylchloride such as 3-chloropropionyl chloride or 4-chlorobutyryl chloride or 5-bromo-pentanoyl chloride, in the presence of Mg, I₂ and a suitable solvent, such as for example tetrahydrofuran. The reaction may conveniently be carried out at a temperature ranging between room temperature and reflux temperature. In a next step (b), an amino group (—NR⁴R⁵) is introduced by reacting the intermediate obtained in step (a) with a primary or secondary amine (HNR⁴R⁵) in the presence of a suitable solvent, such as for example acetonitrile, and a suitable base, such as for example K₂CO₃.

The intermediates of formula (III) may also be prepared according to the following reaction Scheme (8):

Scheme 8

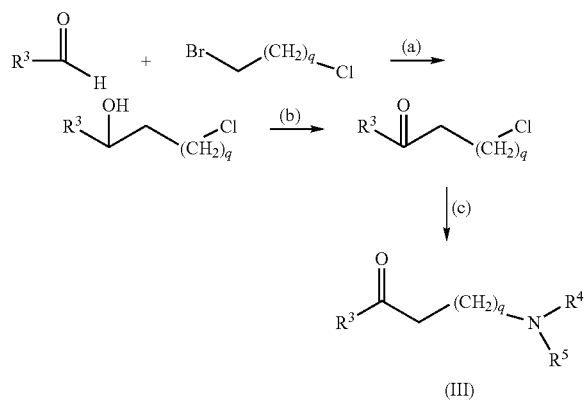

(III)

Reaction scheme (8) comprises step (a) in which R³—C (=O)—H, for instance an appropriately substituted arylcarboxaldehyde, more in particular an appropriately substituted phenyl or naphthylcarboxaldehyde, is reacted with an appropriate intermediate compound such as for example 1-bromo-4-chlorobutane, in the presence of Grignard reagent and a suitable solvent, such as for example diethyl ether, tetrahydrofuran. The reaction may conveniently be carried out at a low temperature for instance 5° C. In a next step (b), an oxidation is performed in the presence of Jones' reagent in a suitable solvent, such as for example acetone. In a next step (c), an amino group (—NR₄R₅) is introduced by reacting the intermediate compound obtained in step (b) with a primary or secondary amine HNR₄R₅ in the presence of a suitable solvent, such as for example acetonitrile, and a suitable base, such as for example K₂CO₃.

Alternatively, intermediates of formula (III) may be prepared according to the following reaction scheme (9):

Scheme 9

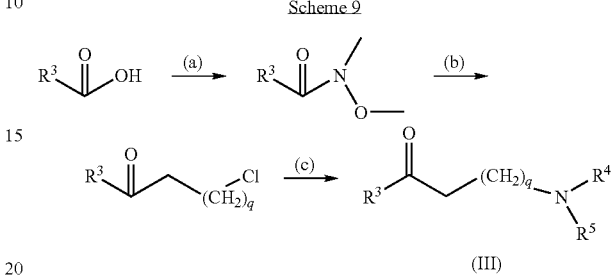

(III)

Reaction scheme (9) comprises step (a) in which for instance a suitable acid is reacted with NH(CH₃)(OCH₃) in the presence of 1,1'-carbonyldiimidazole and a suitable solvent, such as for example CH₂Cl₂. In a next step (b), the product obtained in step (a) is reacted with a suitable Grignard reagens, e.g. 4-chlorobutyl magnesium bromide, in the presence of a suitable solvent, such as for example tetrahydrofuran. In a next step (c), an amino group (—NR₄R₅) is introduced by reacting the intermediate obtained in step (b) with a primary or secondary amine HNR₄R₅ in the presence of a suitable solvent, such as for example acetonitrile, and a suitable base, such as for example K₂CO₃.

Alternatively, intermediates of formula (III) wherein q is 1, said intermediates being represented by formula (III-a), may be prepared according to the following reaction scheme (10):

Scheme 10

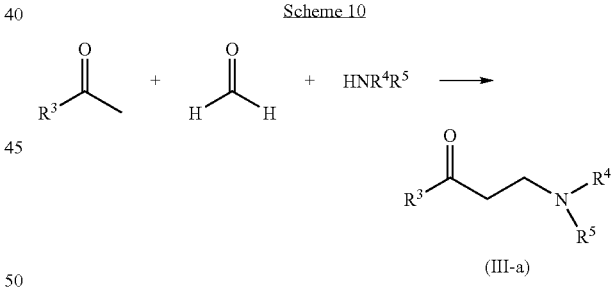

(III-a)

Reaction scheme (10) comprises the step in which a suitable acetyl derivative of R³ such as for example acetylcyclohexane, is reacted with paraformaldehyde and a suitable primary or secondary amine HNR⁴R⁵, preferably in its salt form, in the presence of a suitable acid, such as for example hydrochloric acid and the like, and a suitable solvent, such as for example an alcohol, e.g. ethanol.

Intermediates of formula (III) wherein R³ represents R³ᵃ'—CH₂—CH₂— (which is possible for those intermediates of formula (III) wherein R³ represents alkyl, arylalkyl, aryl-O-alkyl, aryl-alkyl-O-alkyl, Het-alkyl, Het-O-alkyl or Het-alkyl-O-alkyl and R³ᵃ' is the same as R³ but with 2 carbon atoms less in the alkyl chain attached to the remainder of the molecule and wherein q represents 1, said intermediates being represented by formula (III-b), can be prepared according to the following reaction scheme (11):

Scheme 11

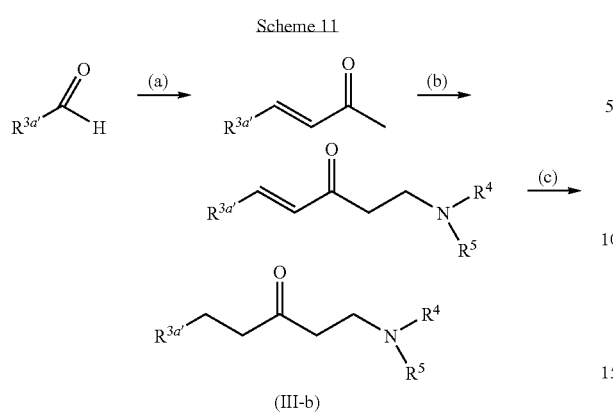

(III-b)

Reaction scheme (11) comprises step (a) wherein a suitable aldehyde is reacted with acetone in the presence of a suitable base, such as for example sodium hydroxide. In a next step (b), the product obtained in step (a) is reacted with a primary or secondary amine $HNR^4R^5$ in the presence of $CH_2(=O)$, a suitable acid, such as for example hydrochloric acid and the like, and a suitable solvent, such as for example an alcohol, e.g. ethanol. In a next step (c), the product obtained in step (b) is hydrogenated ($H_2$) in the presence of a suitable catalyst, such as for example palladium on charcoal, and a suitable solvent, such as for example water and an alcohol, e.g. ethanol.

Intermediates of formula (III) wherein $R^3$ represents a halo substituted phenyl, may be converted into an intermediate of formula (III) wherein $R^3$ represents phenyl substituted with aryl, by reaction with arylboronic acid in the presence of a suitable base, such as for example potassium phosphate, a suitable catalyst, such as for example palladium acetate, and a suitable ligand, such as for example 2-dicyclohexylphosphino-2',6'-dimethoxybiphenyl, in an appropriate solvent, such as for example toluene.

Intermediates of formula (III) wherein $R^3$ represents a halo substituted phenyl, may also be converted into an intermediate of formula (III) wherein $R^3$ represents phenyl substituted with $C_{2-6}$alkenyl optionally substituted with phenyl, by reaction with an appropriate $C_{2-6}$alkene, such as for example styrene, in the presence of a suitable base, such as for example triethylamine, a suitable catalyst, such as for example palladium acetate, and a suitable ligand, such as for example tri-o-tolylphosphine, in an appropriate solvent, such as for example DMF.

Intermediates of formula (IV-a) or (IV-b) can be prepared according to the reaction procedure described in scheme (1) hereinabove or according to the procedures described in WO 2004/011436.

Intermediates of formula (V-a) may be prepared according to the following reaction scheme (12):

Scheme 12

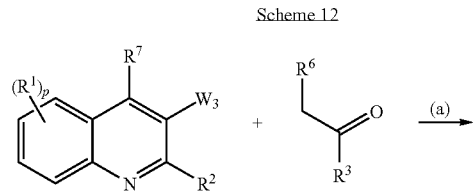

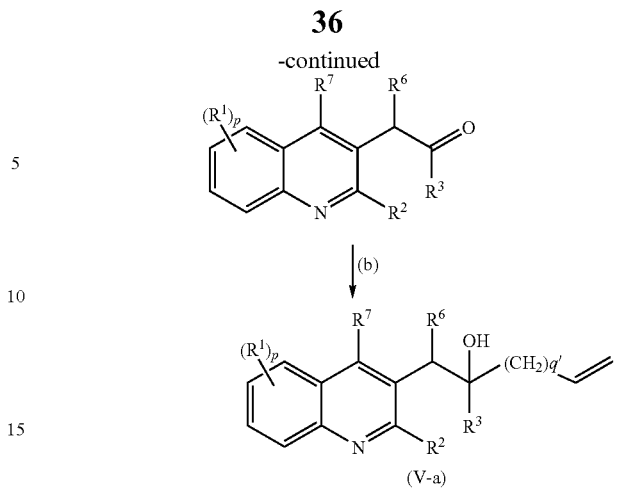

(V-a)

Reaction scheme (12) comprises the step of reacting an appropriately substituted quinoline wherein $W_3$ represents a suitable leaving group, such as for example halo, e.g. bromo, with an appropriately substituted deoxybenzoin in the presence of a suitable catalyst, such as for example palladium diacetate, a suitable ligand, such as for example X-PHOS, a suitable base, such as for example cesium carbonate, a suitable solvent, such as for example xylene, under $N_2$ flow. In a next step (b), the product obtained in step (a) is reacted with a suitable Grignard reagens (e.g. $CH_2=CH-(CH_2)_q-Mg-Br$, such as for example allylmagnesium bromide), in a suitable solvent, such as for example tetrahydrofuran.

Intermediates of formula (V-b) can be prepared accordingly.

Intermediates of formula (VI-a) can be prepared according to the following reaction scheme (13):

Scheme 13

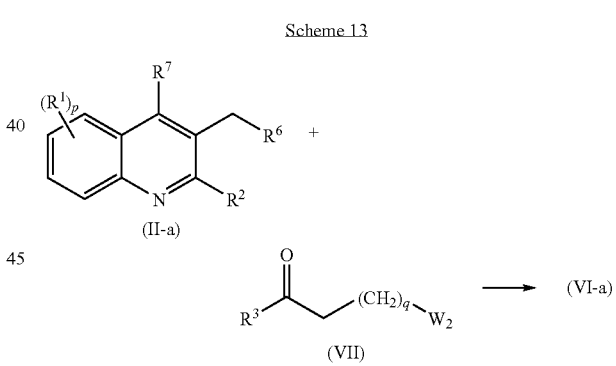

In reaction scheme (13), an intermediate of formula (II-a) is reacted with an intermediate of formula (VII), for its synthesis reference is made to schemes 7, 8 and 9, in the presence of n-BuLi in a suitable solvent, such as for example tetrahydrofuran, and a suitable base, such as for example diisopropyl amine. Stirring may enhance the rate of the reaction. The reaction may conveniently be carried out at a temperature ranging between –20 and –70° C.

Intermediates of formula (VI-b) can be prepared accordingly.

The following examples illustrate the present invention without being limited thereto.

EXPERIMENTAL PART

Of some compounds or intermediates the absolute stereochemical configuration of the stereogenic carbon atoms therein or the configuration at the double bond was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, NMR. It is considered to be within the knowledge of the skilled person to recognize the most appropriate method to determine the actual stereochemical configuration.

In case "A" and "B" are stereoisomeric mixtures, in particular mixtures of enantiomers, they can be further separated whereby the respective first fractions isolated are designated "A1" respectively "B1" and the second as "A2" respectively "B2", without further reference to the actual stereochemical configuration. However, said "A1", "A2" and "B1", "B2" isomeric forms, in particular said "A1", "A2" and "B1", "B2" enantiomeric forms, can be unambiguously characterized by a person skilled in the art, using art-known methods such as, for example, X-ray diffraction.

In some cases, when a final compound or an intermediate, indicated as a particular diastereoisomer or enantiomer, is converted into another final compound/intermediate, the latter may inherit the indication for diastereoisomer (A,B) or enantiomer (A1, A2, B1, B2) from the former.

Hereinafter "DMF" means N,N-dimethylformamide, "THF" means tetrahydrofuran, "TEMPO" means 2,2,6,6-tetramethyl-1-piperidinyloxy, "DIPE" means diisopropyl ether and "DCM" means dichloromethane.

A. Preparation of the Intermediate Compounds

Example A1 a. Preparation of Intermediate 1

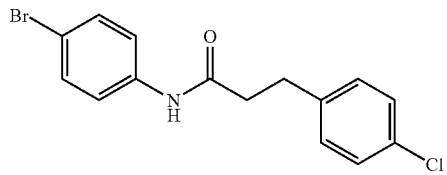

4-chlorobenzenepropanoyl chloride (0.466 mol) was added slowly at 5° C. to a solution of 4-bromobenzenamine (0.388 mol) in Et$_3$N (70 ml) and CH$_2$Cl$_2$ (700 ml). The mixture was stirred at room temperature for 1 hour. H$_2$O was added. The precipitate was filtered off, washed with H$_2$O and dried. The residue was recrystallized from diethyl ether. The precipitate was filtered off and dried. Yield: 110 g of intermediate 1 (83%) (m.p. 194° C.).

b. Preparation of Intermediate 2

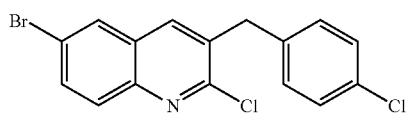

POCl$_3$ (192.6 ml) was added slowly at 5° C. to DMF (35.4 ml). Intermediate 1 (prepared according to A1.a) (0.296 mol) was added. The mixture was stirred at 80° C. for 12 hours, poured out slowly on ice and extracted with CH$_2$Cl$_2$. The organic layer was separated, dried (MgSO$_4$), filtered and the solvent was evaporated. The product was used without further purification. Yield: 150 g of intermediate 2.

c. Preparation of Intermediate 3

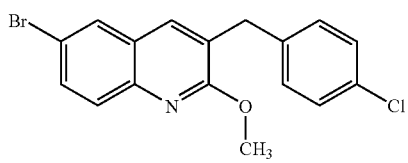

A mixture of intermediate 2 (prepared according to A1.b) (0.409 mol) in CH$_3$ONa solution 30% in CH$_3$OH (300 ml) and CH$_3$OH (300 ml) was stirred and refluxed for 15 hours. The mixture was poured out on ice and extracted with CH$_2$Cl$_2$. The organic layer was separated, dried (MgSO$_4$), filtered and the solvent was evaporated. The residue (150 g) was purified by column chromatography over silica gel (eluent: cyclohexane/CH$_2$Cl$_2$ 90/10; 35-70 μm). The pure fractions were collected and the solvent was evaporated. The residue was crystallized from diethyl ether. The precipitate was filtered off and dried. Yield: 27 g of intermediate 3 (18%) (m.p. 100° C.).

d. Preparation of Intermediate 21

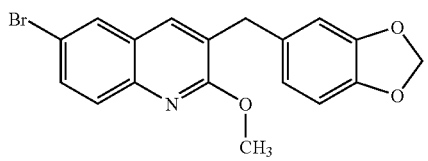

Intermediate 21 was prepared according to the same protocol as intermediate 3 (described in A1.c).

e. Preparation of Intermediate 15

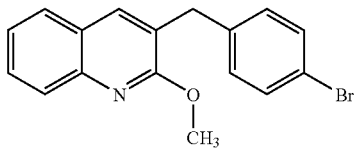

A mixture of

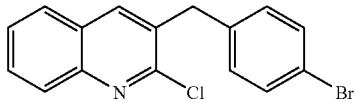

(73 g) (prepared according to A1b), 200 ml of anhydrous methanol and 100 ml of a 5 M solution of sodium methylate was heated under reflux with stirring for 2 days. The formed precipitate was filtered off, washed with methanol and water, and air dried. The residue was chromatographically purified (SiO$_2$, eluent: chloroform 100%). Yield: 53 g of Intermediate 15 (87%, mp=102-103° C.).

Example A2 a-1. Preparation Of Intermediate 4

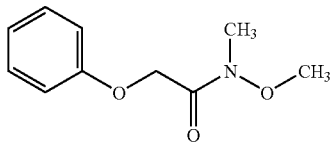

1,1'-carbonyldiimidazole (24 g, 0.148 mol) was added portionwise to a mixture of phenoxyacetic acid (15 g, 0.0985 mol; CAS [122-59-8]) in CH$_2$Cl$_2$ (150 ml) while cooled on a ice-bath at 5° C. The mixture was stirred for 1 hour at 5° C. and N,O-dimethylhydroxylamine hydrochloride (14.4 g, 0.148 mol) was added and the suspension was stirred at room temperature for 20 hours. The mixture was poured out into HCl 1 N and extracted with CH$_2$Cl$_2$. The organic layer was washed with K$_2$CO$_3$ 10%, dried over MgSO$_4$, filtered, and the solvent was evaporated. The residue was purified by column chromatography over silica gel (eluent: CH$_2$Cl$_2$). The pure fractions were collected and the solvent was evaporated. Yielding: 16.6 g of intermediate 4 (86%).

a-2. Preparation of Intermediate 5

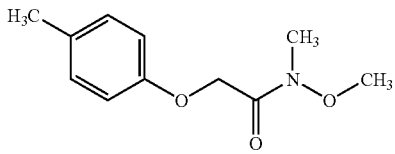

Intermediate 5 was prepared according to the same procedure as described for intermediate 4 in A2.a-1, starting from 4-methylphenoxy acetic acid [940-64-7]. Yield: 98%.

a-3. Preparation of Intermediate 11

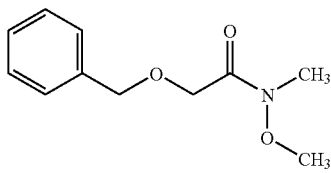

Intermediate 11 was prepared according to the same procedure as described for intermediate 4 in A2.a-1, starting from benzyloxyacetic acid [30379-55-6]. Yield: 95%.

b-1. Preparation of Intermediate 6

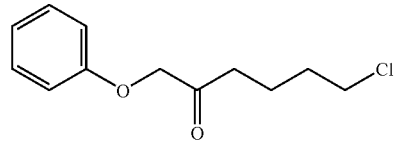

A solution of 1-bromo-4-chlorobutane (12.65 ml, 0.110 mol) in THF/diethyl ether (50/50, 100 ml) was added slowly to a solution of magnesium (2.68 g, 0.110 mol) in THF (30 ml) maintaining a reflux of diethyl ether. The mixture was stirred at room temperature for 30 minutes and then cooled at 5° C. A solution of intermediate 4 (16.56 g, 0.0848 mol) in THF (35 ml) was added. The reaction mixture was then stirred at 50° C. for 4 hours, and cooled down to room temperature. The mixture was hydrolyzed with NH$_4$Cl 10%, and extracted with EtOAc. The organic layer was dried over MgSO$_4$, filtered, and the solvent was evaporated. The residue was used without further purification. Yield: 19 g of intermediate 6 (99%).

b-2. Preparation of Intermediate 7

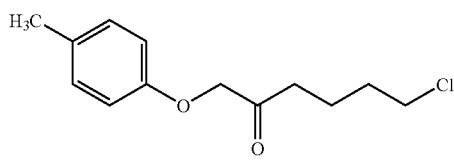

Intermediate 7 was prepared according to the same procedure as described for intermediate 6 in A2.b-1, starting from intermediate 5 and 1-bromo-4-chlorobutane. Yield: 98%.

b-3. Preparation of Intermediate 12

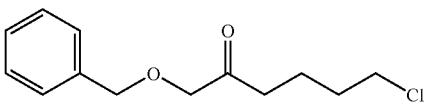

Intermediate 12 was prepared according to the same procedure as described for intermediate 6 in A2.b-1, starting from intermediate 11 and 1-bromo-4-chlorobutane. Yield: 90%.

c-1. Preparation of Intermediate 8

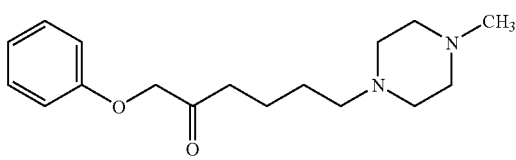

A solution of intermediate 6 (9.6 g, 0.0423 mol), 1-methylpiperazine (4.7 ml, 0.0423 mol) and potassium carbonate (6.4 g, 0.0465 mol) in acetonitrile (100 ml) was heated for 18 hours at 80° C. and then cooled down to room temperature. The mixture was poured out into water, and diethyl ether was added. The organic layer was acidified with HCl 1 N and extracted with diethyl ether. Then the aqueous layer obtained was basified with NaOH 3 N and extracted with diethyl ether. The organic layer was dried over $MgSO_4$, filtered, and the solvent was evaporated. The residue was used without further purification. Yield: 3.82 g of intermediate 8 (31%).

c-2. Preparation of Intermediate 9

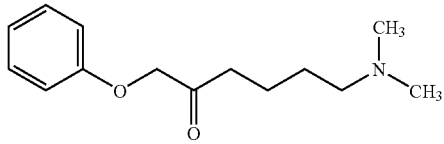

Intermediate 9 was prepared according to the same procedure as described for intermediate 8 in A2.c-1, also starting from intermediate 6. Yield: 33%.

c-3. Preparation of Intermediate 10

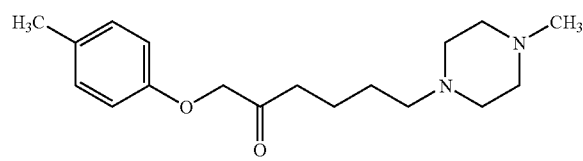

Intermediate 10 was prepared according to the same procedure as described for intermediate 8 in A2.c-1, starting from intermediate 7. Yield: 33%.

c-4. Preparation of Intermediate 13

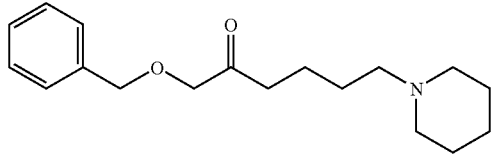

Intermediate 13 was prepared according to the same procedure as described for intermediate 8 in A2.c-1, starting from intermediate 12. Yield: 27%.

c-5. Preparation of Intermediate 14

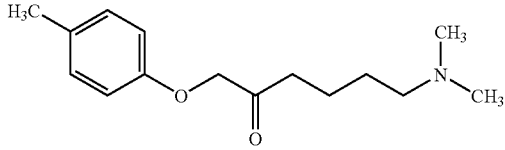

Intermediate 14 was prepared according to the same procedure as described for intermediate 8 in A2.c-1, starting from intermediate 7. Yield: 31%.

c-6. Preparation of Intermediate 23

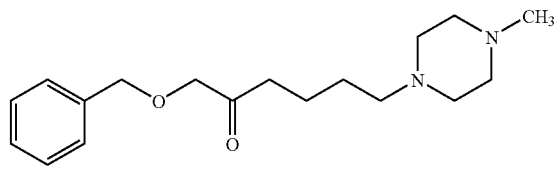

Intermediate 23 was prepared according to the same procedure as described for intermediate 8 in A2.c-1, starting from intermediate 12. Yield: 31%.

Example A3 a. Preparation of Intermediate 22

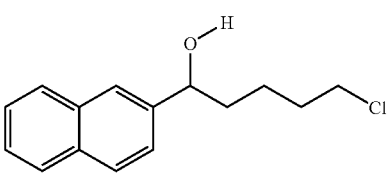

To a stirred solution of Grignard reagent at 5° C., prepared from Mg turnings (0.14 mol) and 1-bromo-4-chlorobutane (0.14 mol) in diethylether (150 ml), was added dropwise a solution of 2-naphtylcarboxaldehyde (0.0935 mol) in THF (150 ml). After the mixture was stirred for 4 hours at 5° C. a solution of ammonium chloride (10% aqueous) was added slowly. The organic layer was separated, washed with brine, dried over magnesium sulfate, filtered, and the solvent was evaporated. The residue was purified by column chromatography over silica gel (eluent:cyclohexane/EtOAc: 90/10; 15-40 μm). The pure fractions were collected and the solvent was evaporated. Yield: 8.2 g of intermediate 22 (35%).

b. Preparation of Intermediate 16

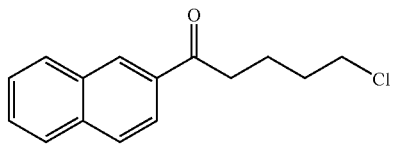

Jones' reagent (0.024 mol), prepared by dissolving 40 g of $CrO_3$ in 80 ml of water and 20 ml of concentrated sulfuric acid, was added drop wise to a cooled solution of intermediate 22 (0.061 mol) in acetone (120 ml). After the addition, the reaction mixture was stirred for 1 hour at 0° C. Water was added and the mixture was extracted with diethyl ether. The organic layer was separated, washed with brine, dried over magnesium sulfate, filtered, and the solvent was evaporated. Yield: 3.8 g of intermediate 16 (96%).

c. Preparation of Intermediate 17

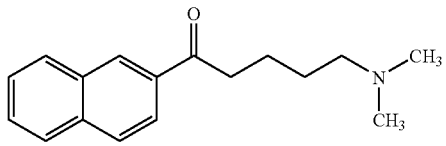

A mixture of intermediate 16 (0.0308 mol), dimethylamine hydrochloride (0.123 mol) and potassium carbonate (0.154 mol) in acetonitrile (150 ml) was stirred under reflux overnight. Then the reaction mixture was cooled to room temperature, poured out into water and extracted with diethylether. The organic layer was extracted with HCl 1 N, the resulting aqueous layer was basified with NaOH 3 N and extracted with diethylether, washed with brine, dried over $MgSO_4$, filtered, and the solvent was evaporated. Yield: 4.2 g of intermediate 17 (53%).

Example A4

Preparation of Intermediate 20

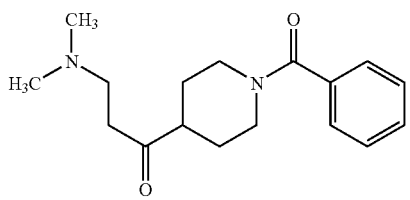

A mixture of 4-acetyl-1-benzoylpiperidine (0.0086 mol; [33037-82-0]), formaldehyde (0.0133 mol), dimethylamine hydrochloride (0.026 mol) and concentrated HCl (1 drop) in EtOH (30 ml) was stirred and refluxed for 72 hours. The solvent was evaporated. The residue was taken up in $CH_2Cl_2$/$H_2O$/NaOH 3 N. The organic layer was separated, dried ($MgSO_4$), filtered, and the solvent was evaporated. The residue (11.7 g) was purified by column chromatography over silica gel (eluent: $CH_2Cl_2$/$CH_3OH$/$NH_4OH$ 95/5/0.1; 20-45 μm). The pure fractions were collected and the solvent was evaporated. Yielding: 5.5 g of intermediate 20 (44%; oil).

Example A5 a-1. Preparation Of Intermediate 18

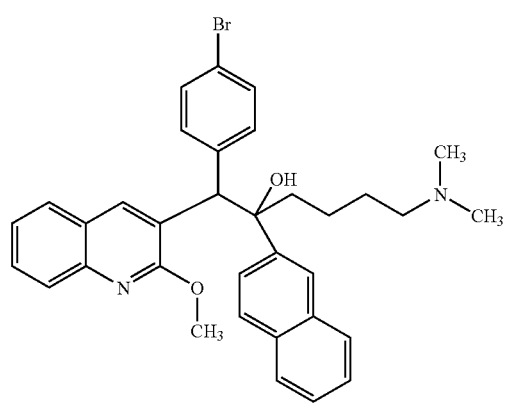

(mixture of dia A and dia B)

A solution of intermediate 15 (0.00661 mol) in THF (20 ml) was added to a solution of lithium diisopropylamide (commercially available, 2 M in THF/heptane, 0.00793 mol) in THF (27 ml) at −70° C. The mixture was stirred at −70° C. for 2 hours. A solution of intermediate 17 (0.00661 mol) in THF (20 ml) was added. The mixture was stirred at −70° C. for 3 hours. Water was added and the mixture was extracted with EtOAc. The organic layer was separated, washed with brine, dried over $MgSO_4$, filtered and the solvent was evaporated. The residue was purified by column chromatography over silica gel (eluent: $CH_2Cl_2$/$CH_3OH$ 50/1; 15-40 μm). The pure fractions were collected and the solvent was evaporated. Yield: Intermediate 18 (a mixture of dia A and dia B) (30%).

a-2. Preparation Of Intermediate 19

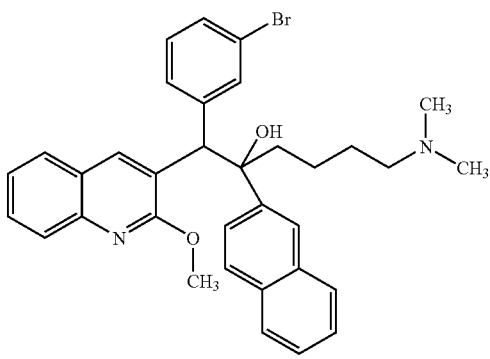

(mixture of dia A and dia B)

Intermediate 19 was prepared according to the same protocol as intermediate 18 (described in A5.a-1).

Example A6 a. Preparation of Intermediate 24

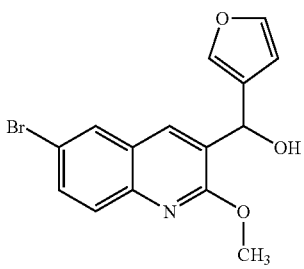

nBuLi 1.6 M in hexane (7.8 ml, 0.0124 mol) was added slowly at −20° C. under $N_2$ flow to a solution of 2,2,6,6-tetramethylpiperidine (2.1 ml, 0.0124 mol) in THF (32 ml). The mixture was stirred at −20° C. for 20 minutes, and then cooled at −70° C. A solution of 6-bromo-2-methoxyquinoline (CAS 99455-05-7) (2.5 g, 0.0104 mol) in THF (24 ml) was added slowly. The mixture was stirred at −70° C. for 90 minutes. A solution of 3-furancarboxaldehyde (1.2 g, 0.0124 mol) in THF (18 ml) was added slowly. The mixture was stirred overnight at room temperature, hydrolyzed with ice water, and extracted with EtOAc. The organic layer was separated, dried over $MgSO_4$, filtered, and the solvent was evaporated. The residue was purified by column chromatography over silica gel (eluent:cyclohexane/EtOAc: 50/50; 15-40 µm). The desired fractions were collected and the solvent was evaporated. Yield: 1.46 g of intermediate 24 (yield: 39%) as a white solid.

b. Preparation of Intermediate 25

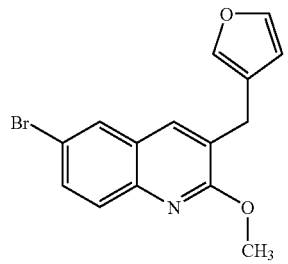

Trifluoroacetic acid (2.3 ml; 0.003 mol) was added to a solution of intermediate 24 (0.5 g; 0.0015 mol) and triisopropylsilane (6.1 ml; 0.003 mol) in $CH_2Cl_2$ (15 ml). The mixture was stirred overnight at room temperature, hydrolyzed with ice water, and extracted with EtOAc. The organic layer was separated, dried over $MgSO_4$, filtered, and the solvent was evaporated. The residue was purified by column chromatography over silica gel (eluent: cyclohexane/EtOAc from 100/0 to 0/100; 15-40 µm). The desired fractions were collected and the solvent was evaporated. 0.30 g of intermediate 25 (yield: 61%) as a pale yellow solid.

Example A7 a. Preparation of Intermediate 26

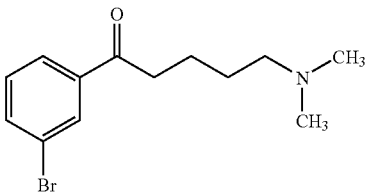

A mixture of 1-(3-bromophenyl)-5-chloro-1-pentanone (18.0 g; 0.07 mol), dimethylamine hydrochloride (22.8 g; 0.28 mol), and potassium carbonate (47.7 g, 0.35 mol) in acetonitrile (25 ml) was stirred under reflux for 48 hours, was then cooled to room temperature, poured out into water and extracted with EtOAc. The organic layer was separated, washed with brine, dried over magnesium sulfate, filtered and the solvent was evaporated. The crude product was taken up in DIPE and the precipitate was filtered off and dried under vacuum. Yield: 16.8 g of intermediate 26 (90%).

b-1. Preparation of Intermediate 27

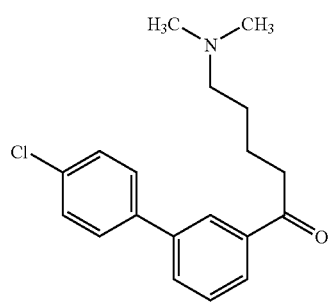

In a three-neck flask under N₂ flow were introduced 4-chlorophenylboronic acid (2.49 g; 15.9 mmol), potassium phosphate (4.5 g; 21.2 mmol), palladium acetate (72 mg; 0.32 mmol) and 2-dicyclohexylphosphino-2',6'-dimethoxybiphenyl (275 mg; 0.67 mmol). Then, 21.2 ml of anhydrous toluene was added via a syringe. After 2 minutes, intermediate 26 (3.0 g; 10.6 mmol) was added and the mixture was stirred for 3 hours at 100° C. The reaction was quenched with water and diluted with dichloromethane. The organic layer was then washed with water and brine, dried over magnesium sulphate, filtered and concentrated. The crude product was purified by chromatography on silica gel (CH₂Cl₂/CH₃OH/NH₄OH from 97/3/0.3 to 90/10/1). Yield: 2.27 g (68%) of intermediate 27.

b-2. Preparation of Intermediate 28

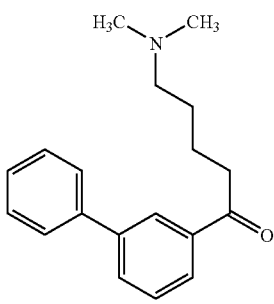

Intermediate 28 was prepared according to the same procedure as described for intermediate 27 (in A7.b-1), starting from intermediate 26 and phenylboronic acid instead of 4-chlorophenylboronic acid. Yield: 61%.

b-3. Preparation of Intermediate 29

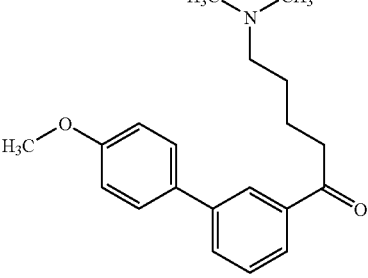

Intermediate 29 was prepared according to the same procedure as described for intermediate 27 (in A7.b-1), starting from intermediate 26 and 4-methoxyphenylboronic acid instead of 4-chlorophenylboronic acid. Yield: 85%.

b-4. Preparation of Intermediate 30

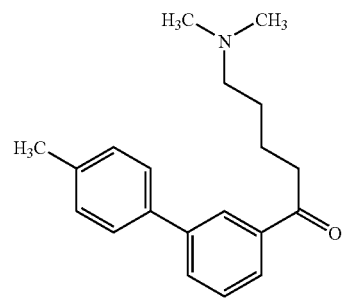

Intermediate 30 was prepared according to the same procedure as described for intermediate 27 (in A7.b-1), starting from intermediate 26 and 4-methylphenylboronic acid instead of 4-chlorophenylboronic acid. Yield: 79%.

Example A8 a-1. Preparation of Intermediate 31

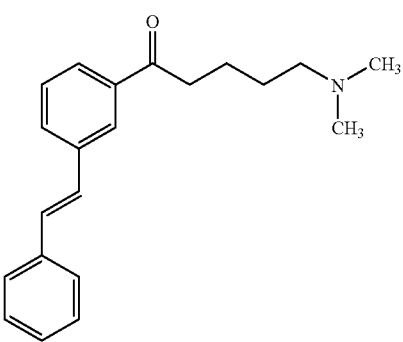

In a round-bottom flask were introduced palladium acetate (71.8 mg; 0.32 mmol); tri-o-tolylphosphine (289 mg; 0.95 mmol) and 30 ml of DMF. After 2 minutes, 3.0 g (10.6 mmol) of intermediate 26, 1.3 g (12.7 mmol) of styrene and 2.2 ml (15.9 mmol) of triethylamine were added to the stirred solution. Then, the reaction mixture was heated at 100° C. overnight. The mixture was poured into ice-water and diluted with ethyl acetate. The aqueous layer was then washed three times with ethyl acetate and the gathered organic fractions were washed with water and brine, dried over magnesium sulfate, filtered and concentrated. The crude product was purified by chromatography on silica gel ($CH_2Cl_2/CH_3OH/NH_4OH$ from 97/3/0.3 to 90/10/1). Yield: 2.75 g of intermediate 31 (85%; isomer (E)).

a-2. Preparation of Intermediate 36

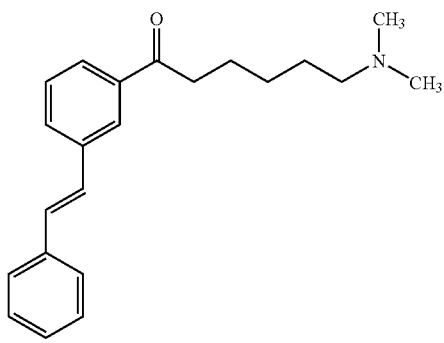

Intermediate 36 was prepared according to the same procedure as described for intermediate 31 (see A8.a-1), starting from intermediate 34 (see A9.c).

Example A9 a. Preparation of Intermediate 32

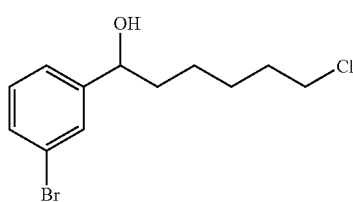

In a three-neck flask under $N_2$ flow were introduced magnesium (4.8 g, 0.202 mol) in 15 ml of THF and a catalytic amount of 12. A few drops of 1-bromo-5-chloropentane were added to initiate the reaction. After the solution had lost its color, more 1-bromo-5-chloropentane (26.6 ml, 0.2 mol) in 75 ml of THF were added dropwise keeping the temperature at about 10° C. The mixture was stirred for 1 hour at this temperature. Then the solution of 3-bromobenzaldehyde (15.8 ml, 1.35 mol) in 75 ml of THF was added dropwise at 10° C. and the mixture was stirred half a day at room temperature. The reaction was quenched with aqueous ammonium chloride (10% solution), diluted with ethyl acetate and filtered on Celite. The organic layer was then washed with water and brine, dried over magnesium sulfate, filtered and concentrated. The crude product was purified by chromatography on silica gel (cyclohexane/EtOAc 80/20). Yield: 15 g of intermediate 32 (38%).

b. Preparation of Intermediate 33

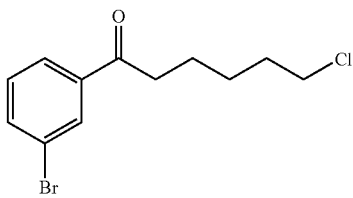

In a round-bottom flask intermediate 32 (15.0 g; 51.4 mmol) and TEMPO (80 mg; 0.51 mmol) in 30 mL of DCM were stirred. Then, the aqueous solution of sodium periodate (30 ml; 13.2 g; 61.7 mmol) and sodium bromide (0.52 g; 5.1 mmol) were added to the reaction mixture which was vigorously stirred for 24 hours at room temperature. The reaction was diluted with water and DCM. The organic layer was then washed with sodium sulfate, dried over magnesium sulfate, filtered and concentrated. Yielding 14.83 g of intermediate 33 (100%).

c. Preparation of Intermediate 34

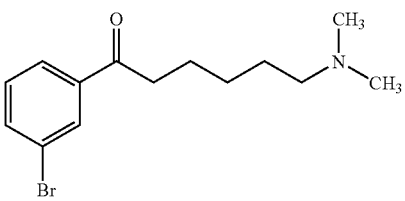

A mixture of intermediate 33 (14.83 g; 51.2 mmol), dimethylamine hydrochloride (16.7 g, 0.21 mol) and potassium carbonate (36.2 g, 0.26 mol) in acetonitrile (150 ml) was stirred under reflux for 48 hours and was then cooled to room temperature. The mixture was poured out into water and extracted with EtOAc. The organic layer was separated, washed with brine, dried over magnesium sulfate, filtered and the solvent was evaporated. The crude product was taken up in DIPE and the precipitate was filtered off and dried under vacuum. Yield: 16.8 g of intermediate 34 (97%).

d. Preparation of Intermediate 35

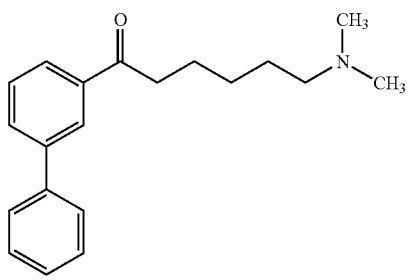

Intermediate 35 was prepared according to the same procedure as described for intermediate 27 (A7.b-1), starting from intermediate 34 and phenylboronic acid. Yield: 11%.

B. Preparation of the Compounds

Example B1

Preparation of Compounds 3 and 4

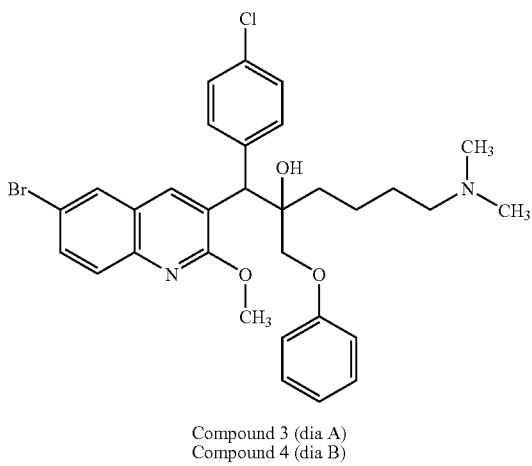

Compound 3 (dia A)
Compound 4 (dia B)

nBuLi 1.6 M in hexane (4.3 ml, 0.0069 mol) was added slowly at −20° C. under $N_2$ flow to a solution of diisopropylamine (0.97 ml, 0.0069 mol) in THF (12 ml). The mixture was stirred at −20° C. for 20 minutes, and then cooled at −70° C. A solution of intermediate 3 (1.89 g, 0.00575 mol) in THF (20 ml) was added slowly. The mixture was stirred at −70° C. for 90 minutes. A solution of intermediate 9 (1.625 g, 0.0069 mol) in THF (17 ml) was added slowly. The mixture was stirred at −70° C. for 3 hours, hydrolyzed at −30° C. with ice water, and extracted with EtOAc. The organic layer was separated, dried over $MgSO_4$, filtered, and the solvent was evaporated. The residue was first purified by column chromatography over silica gel (15-40 μm, 90 g, $CH_2Cl_2/CH_3OH/NH_4OH$: 95%/5%/0.5%) and then the purification was carried out with SFC, on a 2-ethylpyridine column (6 μm; 20×150 mm). The Mobile phase was $CO_2$/methanol (+0.5% V/V Isopropylamine) 93/7 V/V. Two fractions were collected and the solvent was evaporated. Fractions were crystallized separately from diisopropylether, yielding 0.21 g of compound 3 (diastereoisomer A; yield: 6.2%; white foam) and 0.23 g of compound 4 (diastereoisomer B; yield: 6.8%; mp: 118° C.; white solid).

Example B2

Preparation of Compounds 21 and 22

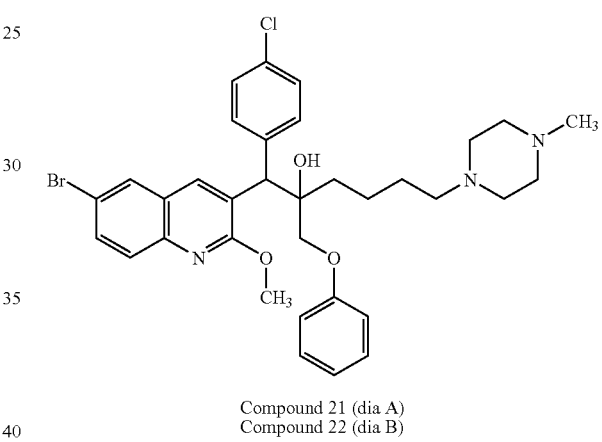

Compound 21 (dia A)
Compound 22 (dia B)

nBuLi 1.6 M in hexane (4.1 ml, 0.00658 mol) was added slowly at −20° C. under $N_2$ flow to a solution of diisopropylamine (0.92 ml, 0.00658 mol) in THF (11 ml). The mixture was stirred at −20° C. for 20 minutes, and then cooled at −70° C. A solution of intermediate 3 (1.98 g, 0.00547 mol) in THF (20 ml) was added slowly. The mixture was stirred at −70° C. for 90 minutes. A solution of intermediate 8 (1.91 g, 0.00658 mol) in THF (19 ml) was added slowly. The mixture was stirred at −70° C. for 3 hours, hydrolyzed at −30° C. with ice water, and extracted with EtOAc. The organic layer was separated, dried over $MgSO_4$, filtered, and the solvent was evaporated. The residue was first purified by column chromatography over silica gel Kromasil (5 μm, 19×150 mm; $CH_2Cl_2/CH_3OH/NH_4OH$ 96/4/0.4 V/V/V) and then over a Sunfire™ C18 column from Waters (5 μm19×150 mm) with a flow rate of 20 ml/min. Two mobile phases (mobile phase A: 100% Methanol; mobile phase B: 100% 63 mM ammonium hydrogen carbonate pH=8 (in ultra pure water) were employed to run a gradient condition from 87% A, 13% B to 100% A in 14 minutes, and reequilibrated with initial conditions for 6 minutes. Two fractions were collected and the solvent was evaporated. The two fractions were crystallized separately from diisopropylether, yielding 0.045 g of compound 21 (diastereoisomer A; yield: 1.3%; white foam) and 0.23 g of compound 22 (diastereoisomer B; yield: 1.3%; mp: 158° C.; white solid).

Example B3

Preparation of Compounds 27 and 28

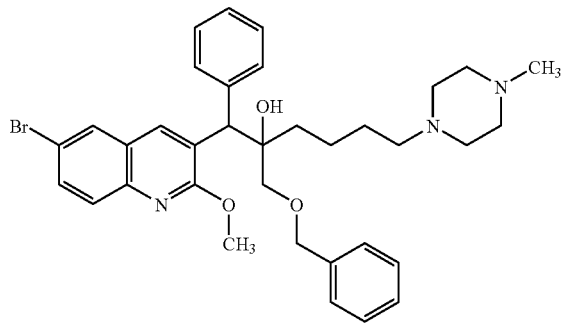

Compound 27 (dia A)
Compound 28 (dia B)

nBuLi 1.6 M in hexane (5.3 ml, 0.0085 mol) was added slowly at −20° C. under $N_2$ flow to a solution of diisopropylamine (1.2 ml, 0.0085 mol) in THF (15 ml). The mixture was stirred at −20° C. for 20 minutes, and then cooled at −70° C. A solution of 6-bromo-2-methoxy-3-(phenylmethyl)-quinoline(intermediate compound 3 (Ex. A3) of WO2004/011436) (2.32 g, 0.00708 mol) in THF (23 ml) was added slowly. The mixture was stirred at −70° C. for 90 minutes. A solution of intermediate 23 (2.6 g, 0.0085 mol) in THF (26 ml) was added slowly. The mixture was stirred at −70° C. for 3 hours, hydrolyzed at −30° C. with ice water, and extracted with EtOAc. The organic layer was separated, dried over $MgSO_4$, filtered, and the solvent was evaporated. The residue was twice purified by column chromatography over silica gel (15-40 μm, 300 g, $CH_2Cl_2/CH_3OH/NH_4OH$ 93/7/0.1 v/v/v). Two fractions were collected and the solvent was evaporated. Fractions were crystallized separately from DIPE, yielding 0.38 g of compound 27 (diastereoisomer A; yield: 8.6%; white foam) and 0.21 g of compound 28 (diastereoisomer B; yield: 4.8%; mp: 122° C.; white solid).

Example B4 a) Preparation of Compounds 25 and 26

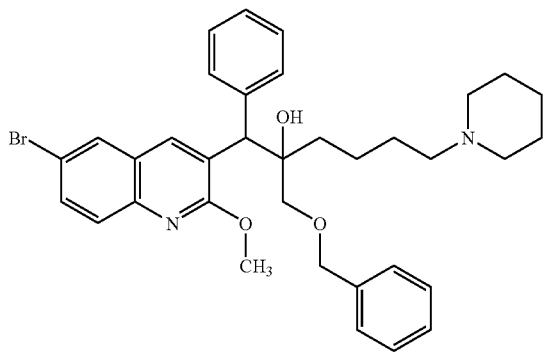

Compound 25 (dia A)
Compound 26 (dia B)

nBuLi 1.6 M in hexane (4.99 ml, 0.0079 mol) was added dropwise at −20° C. to a solution of diisopropylamine (0.0079 mol) in THF (13 ml) under $N_2$ flow. The mixture was stirred at −20° C. for 20 minutes, then cooled to −70° C. A solution of 6-bromo-2-methoxy-3-(phenylmethyl)-quinoline (intermediate compound 3 (Ex. A3) of WO2004/011436) (0.0065 mol) in THF (22 ml) was added. The mixture was stirred at −70° C. for 90 minutes. A solution of intermediate 13 (0.0079 mol) in THF (20 ml) was added. The mixture was stirred at −70° C. for 2 hours, then poured out on ice at −30° C. and extracted with EtOAc. The organic layer was separated, dried ($MgSO_4$), filtered and the solvent was evaporated. The residue was purified twice by column chromatography over silica gel (eluent: $CH_2Cl_2/CH_3OH/NH_4OH$ 95/5/0.1 to 93/7/0.1; 15-40 μm). Three fractions were collected and the solvent was evaporated. Yield: 0.5 g of fraction 1, 0.41 g of fraction 2 and 0.37 g of fraction 3. Fraction 1 and fraction 3 were crystallized from DIPE. The precipitate was filtered off and dried. Yield: 0.33 g of compound 25 (8.3%; dia A) and 0.25 g of compound 26 (6.3%; dia B).

b) Preparation of Compounds 1 and 2

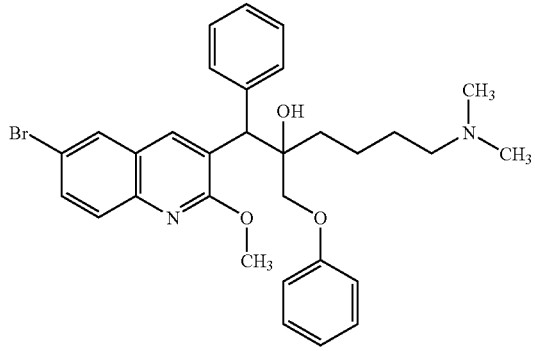

Compound 1 (dia A)
Compound 2 (dia B)

Compounds 1 and 2 were prepared according to the procedure for compounds 25 and 26 as described in B4.a, but using intermediate 9 (instead of intermediate 13) and using a different work-up procedure. The separated organic layer was washed with saturated aqueous NaCl, dried ($MgSO_4$), filtered and the solvent was evaporated. The residue was purified by column chromatography over silica gel (eluent: $CH_2Cl_2/CH_3OH/NH_4OH$ 95/5/0.1; 15-40 μm), then over kromasil (eluent: $CH_2Cl_2/CH_3OH/NH_4OH$ 96/4/0.4; 5 μm). Three fractions were collected and the solvent was evaporated. The first desired fraction was crystallized from DIPE. The precipitate was filtered off and dried. Yield: Compound 1 (8.5%; dia A; mp: 148° C.). The second desired fraction was crystallized from DIPE. The precipitate was filtered off and dried. Yield: Compound 2 (1.9%; dia B; mp: 151° C.).

c) Preparation of Compounds 19 and 20

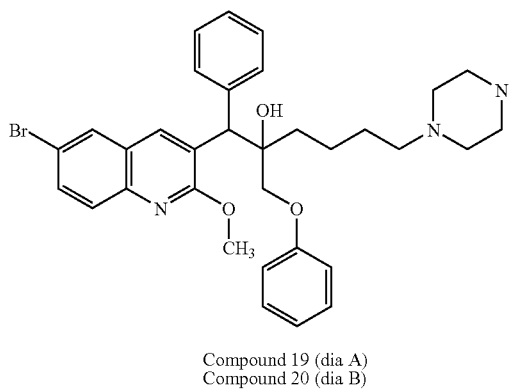

Compound 19 (dia A)
Compound 20 (dia B)

Compounds 19 and 20 were prepared according to the procedure for compounds 25 and 26 as described in B4.a, but using intermediate 8 (instead of intermediate 13) and using a different work-up procedure. The separated organic layer was washed with saturated aqueous NaCl, dried ($MgSO_4$), filtered and the solvent was evaporated. The residue was purified by column chromatography over silica gel (eluent: $CH_2Cl_2$/$CH_3OH$/$NH_4OH$ 95/5/0.1; 15-40 µm), then over kromasil (eluent: $CH_2Cl_2$/$CH_3OH$/$NH_4OH$ 96/4/0.4 to 91/9/0.9; 5 µm). Two fractions were collected and the solvent was evaporated. Fraction 1 was crystallized from DIPE. The precipitate was filtered off and dried. Yield: Compound 19 (7.3%; dia A). Fraction 2 was crystallized from DIPE. The precipitate was filtered off and dried. Yield: Compound 20 (5.9%; dia B; mp: 144° C.).

d) Preparation of Compounds 23 and 24

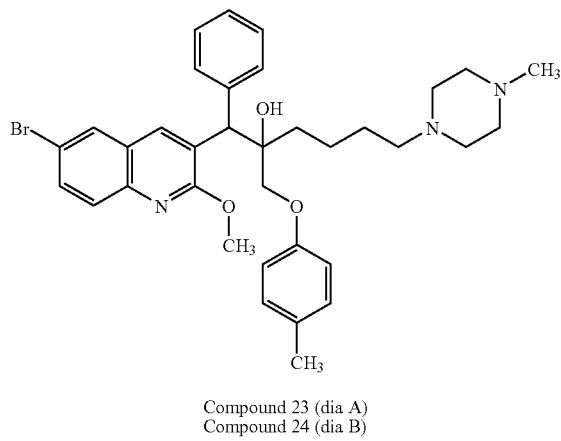

Compound 23 (dia A)
Compound 24 (dia B)

Compounds 23 and 24 were prepared according to the procedure for compounds 25 and 26 as described in B4.a, but using intermediate 10 (instead of intermediate 13) and using a different work-up procedure. After removal of the solvent of the separated organic layer, the residue was purified by column chromatography over silica gel (eluent: $CH_2Cl_2$/$CH_3OH$/$NH_4OH$ 95/5/0.1). The pure fractions were collected and the solvent was evaporated. The residue was purified by column chromatography over Kromasil (eluent: $CH_2Cl_2$/$CH_3OH$/$NH_4OH$ 96/4/0.4; 5 µm). Two fractions were collected and the solvent was evaporated. Both residues were crystallized from DIPE. The precipitate was filtered off and dried. Yield: Compound 23 (3.1%; dia A) and compound 24 (2.1%; dia B) (mp: 168° C.).

e) Preparation of Compounds 5 and 6

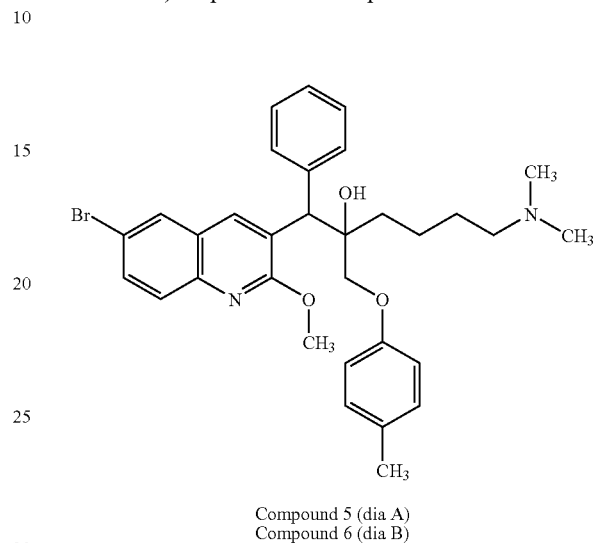

Compound 5 (dia A)
Compound 6 (dia B)

Compounds 5 and 6 were prepared according to the same procedure as for compounds 23 and 24, but using intermediate 14 (instead of intermediate 10). Working-up procedure: The residue was first purified by column chromatography over silica gel (eluent: $CH_2Cl_2$/$CH_3OH$/$NH_4OH$ 95/5/0.1; 15-40 µm), and then over a Kromasil column (eluent: $CH_2Cl_2$/$CH_3OH$/$NH_4OH$ 96/4/0.4; 5 µm). Two fractions were collected and the solvent was evaporated. Fraction 1 was crystallized from DIPE. The precipitate was filtered off and dried. Yield: Compound 5 (5.8%; mp: 146° C.; dia A). Fraction 2 was crystallized from DIPE. The precipitate was filtered off and dried, yielding compound 6 (1.1%; mp: 130° C.; dia B).

Example B5 a. Preparation of Compounds 14 and 15

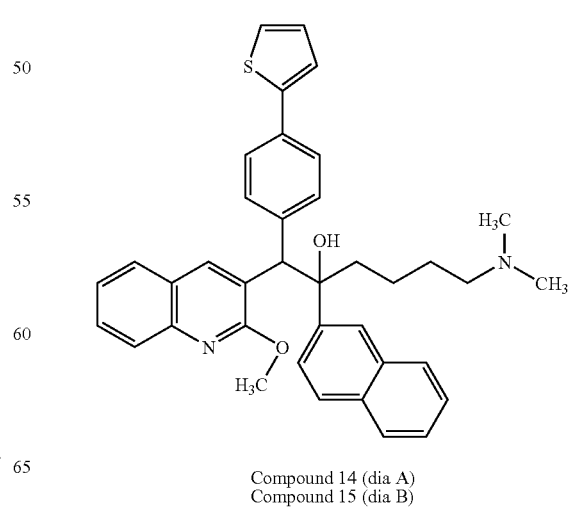

Compound 14 (dia A)
Compound 15 (dia B)

Intermediate 18 (mixture of dia A and B) (0.00103 mol) was dissolved in dimethoxyethane (1.5 ml) and CH₃OH (1.5 ml). Na₂CO₃ (2.0 M solution in water), thiophene-2-boronic acid (0.00154 mol) and Pd(PPh₃)₂Cl₂ (0.00005 mol) were added to this solution. The reaction mixture was stirred in a microwave oven at 90° C. for 2×9 minutes (P=300 W). Then the mixture was cooled to room temperature and poured out into H₂O. CH₂Cl₂ was added and the mixture was filtered over a short pad of Celite. The filtrate was decanted and the organic layer was dried (MgSO₄), filtered and the solvent was evaporated. Column purification: The residue was purified by flash chromatography (eluent: CH₂Cl₂/CH₃OH 50/1). Two fractions were collected and the solvent was evaporated. Yielding: 0.070 g of compound 14 (dia A, 12%) and 0.135 g of compound 15 (dia B, 22%).

b. Preparation of Compounds 12 and 13

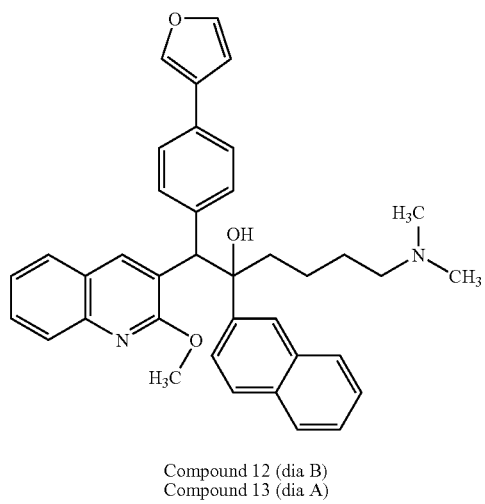

Compound 12 (dia B)
Compound 13 (dia A)

Compounds 12 and 13 were prepared according to the procedure for compounds 14 and 15 as described in B5.a, starting from intermediate 18 and furan-3-boronic acid. Column purification: The residue was first purified by flash chromatography (eluent: CH₂Cl₂/CH₃OH 50/1), but the compounds 12 and 13 were not separated from each other. Therefore, this mixture of diastereoisomers was further purified with an additional work-up: The residue was purified by column chromatography over Kromasil (eluent: CH₂Cl₂/CH₃OH/NH₄OH from 96/4/0.4 to 91/9/0.9; 10 μm). Two fractions were collected and the solvent was evaporated. Fraction 1 was crystallized from DIPE. The precipitate was filtered off and dried. Yield: Compound 13 (37 mg; mp: 197° C.; dia A). Fraction 2 was crystallized from DIPE. The precipitate was filtered off and dried compound 12 (29 mg; dia B).

c. Preparation of Compounds 10 and 11

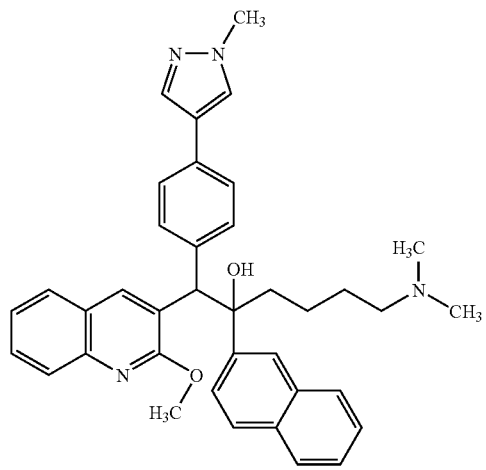

Compound 11 (dia A)
Compound 10 (dia B)

Compounds 10 and 11 were prepared according to the procedure for compounds 14 and 15 as described in B5.a, starting from intermediate 18 and 1-methyl-4-(4,4,5,5-tetramethyl-1,3,2-dioxaborolan-2-yl)-1H-pyrazole. Column purification: The residue was first purified by flash chromatography (eluent: CH₂Cl₂/CH₃OH 50/1), but the compounds 11 and 10 were not separated from each other. Therefore, this mixture of diastereoisomers was further purified with an additional work-up: The residue was purified by column chromatography over Kromasil (eluent: CH₂Cl₂/CH₃OH/NH₄OH from 96/4/0.4 to 91/9/0.9; 10 μm). Two fractions were collected and the solvent was evaporated. Fraction 1 was crystallized from DIPE. The precipitate was filtered off and dried. Yield: Compound 11 (15 mg; dia A). Fraction 2 was crystallized from DIPE. The precipitate was filtered off and dried, yielding compound 10 (12 mg; mp: 190° C.; dia B).

d. Preparation of Compounds 8 and 9

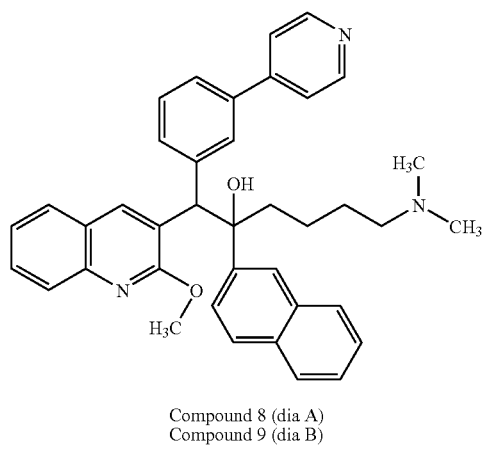

Compound 8 (dia A)
Compound 9 (dia B)

Compounds 8 and 9 were prepared according to the procedure for compounds 14 and 15 as described in B5.a, starting from intermediate 19 (0.7 g, 0.00119 mol) and 4-pyridineboronic acid (0.221 g, 0.00180 mol). Column purification: After removal of the solvent, the residue was purified by flash column chromatography (eluent: from CH$_2$Cl$_2$/CH$_3$OH 50/1+1% Et$_3$N to CH$_2$Cl$_2$/CH$_3$OH 48/1+1% Et$_3$N to CH$_2$Cl$_2$/CH$_3$OH 46/1+1% Et$_3$N to CH$_2$Cl$_2$/CH$_3$OH 45/1+1% Et$_3$N). Both diastereoisomers were separated from each other under these conditions. The products were dried (vacuum, room temperature) and crystallized from ether, yielding white solids. Yield: Compound 8 (58 mg; 8%; dia A) and compound 9 (169 mg; 24%; dia B).

e. Preparation of Compound 7 and 7b

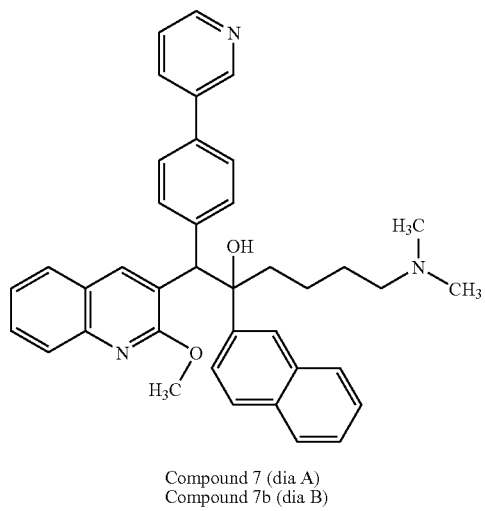

Compound 7 (dia A)
Compound 7b (dia B)

Compound 7 was prepared according to the procedure for compound 14 as described in B5.a, starting from intermediate 18 and 3-pyridineboronic acid. Column purification: After removal of the solvent, the residue was purified by flash chromatography (eluent: CH$_2$Cl$_2$/MeOH 50/1). The desired fraction was collected and the solvent was evaporated, yielding 0.045 g of compound 7 (dia A) and 0.030 g of compound 7b (dia B).

Alternative column procedure: The residue can also be separated into diastereoisomers by column chromatography over Kromasil (eluent: CH$_2$Cl$_2$/CH$_3$OH/NH$_4$OH 96/4/0.4 to 91/9/0.9; 10 μm).

f. Preparation of Compound 16

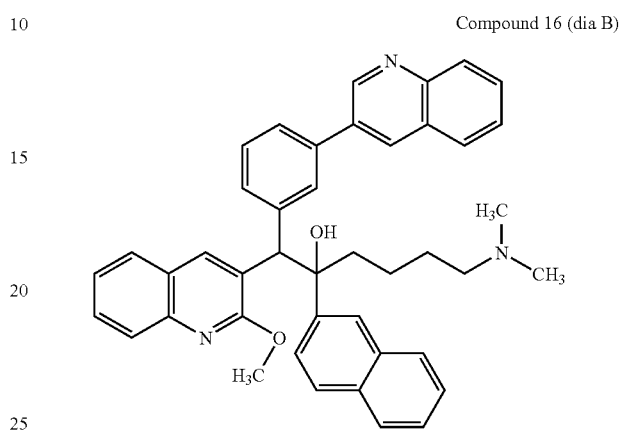

Compound 16 (dia B)

Compound 16 was prepared according to the procedure for compound 14 as described in B5.a, starting from intermediate 19 and 3-quinolineboronic acid. Column purification: The residue was first purified by flash chromatography (eluent: CH$_2$Cl$_2$/CH$_3$OH 50/1), and then the residue was further purified over Kromasil (eluent: CH$_2$Cl$_2$/CH$_3$OH/NH$_4$OH 96/4/0.4 to 91/9/0.9; 10 μm). The second fraction was crystallized from DIPE. The precipitate was filtered off and dried. Yield: Compound 16 (16 mg; mp: 141° C.; dia B).

g. Preparation of Compounds 43 and 48

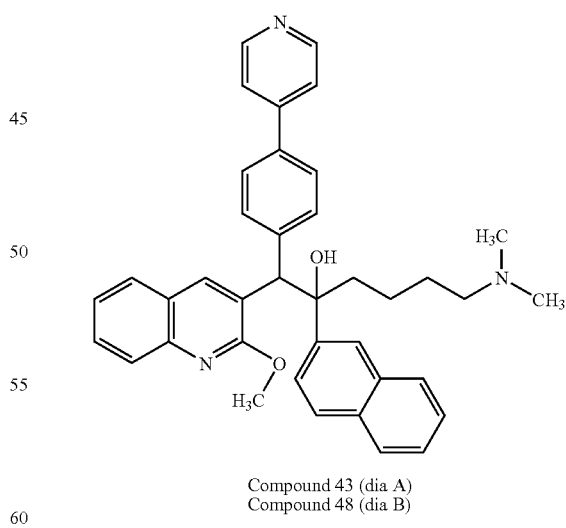

Compound 43 (dia A)
Compound 48 (dia B)

Compounds 43 and 48 were prepared according to the procedure for compounds 14 and 15 as described in B5.a, starting from intermediate 18 and 4-pyridineboronic acid. Column purification: The residue was first purified by flash chromatography (eluent: CH$_2$Cl$_2$/CH$_3$OH from 50/1 to 40/1), but the compounds 43 and 48 were not separated from each other. Therefore, this mixture of diastereoisomers was further purified with an additional work-up: The residue was purified by column chromatography over silica gel (eluent: CH$_2$Cl$_2$/CH$_3$OH/NH$_4$OH 96/4/0.4 to 91/9/0.9; 10 μm). Two fractions were collected and the solvent was evaporated. Yield: Compound 43 (dia A; 2.2% yield) and compound 48 (dia B; 5.8% yield; m.p.: 210° C.).

h. Preparation of Compounds 49 and 50

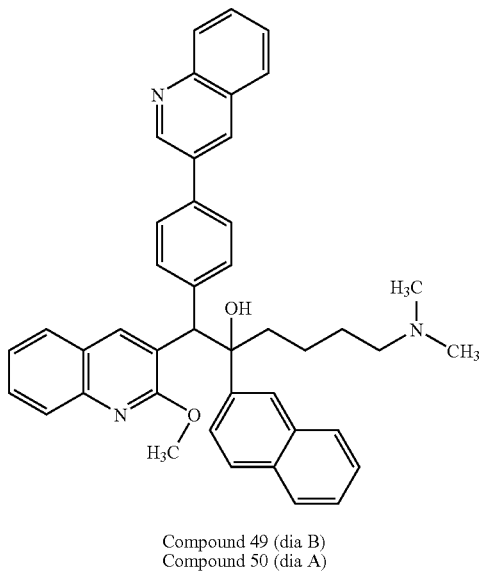

Compound 49 (dia B)
Compound 50 (dia A)

Compounds 49 and 50 were prepared according to the procedure for compounds 14 and 15 as described in B5.a, starting from intermediate 18 and 3-quinolineboronic acid. Column purification: The residue was first purified by flash chromatography (eluent: CH$_2$Cl$_2$/CH$_3$OH 50/1) to remove impurities, but the compounds 49 and 50 were not separated from each other. Therefore, this mixture of diastereoisomers was further purified with reversed phase chromatography (XBridge™ C18 column from Waters (5 μm; 30×150 mm) with a flow rate of 40 ml/min. Two mobile phases (mobile phase A: 100% acetonitrile; mobile phase B: 100% 63 mM ammonium hydrogen carbonate pH=10.2 (in ultra pure water) were employed to run a gradient condition from 80% A, 20% B to 100% A in 14 minutes, and reequilibrated with initial conditions for 6 minutes. The desired fractions were collected and the solvent was evaporated. Yield: Compound 50 (9.6%, dia A) and compound 49 (12%, dia B).

Example B7

Preparation of Compounds 29 and 30

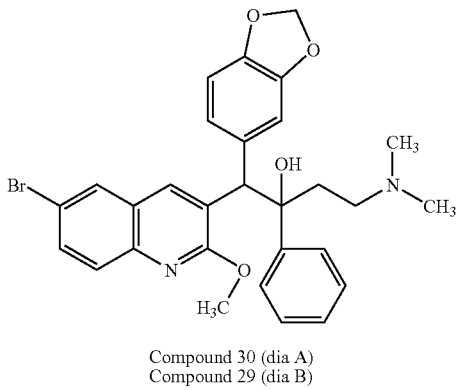

Compound 30 (dia A)
Compound 29 (dia B)

nBuLi 1.6 M in hexane (2.24 ml, 0.0036 mol) was added slowly at −20° C. under N$_2$ flow to a solution of diisopropylamine (0.503 ml, 0.0036 mol) in THF (8 ml). The mixture was stirred at −20° C. for 20 minutes, and then cooled at −70° C. A solution of intermediate 21 (0.003 mol) in THF (10 ml) was added slowly. The mixture was stirred at −70° C. for 90 minutes. A solution of 3-(dimethylamino)-1-phenyl-1-propanone (0.64 g, 0.0036 mol) in THF (7 ml) was added slowly. The mixture was stirred at −70° C. for 3 hours, hydrolyzed at −30° C. with ice water, and extracted with EtOAc. The organic layer was separated, dried over MgSO$_4$, filtered, and the solvent was evaporated. The residue (1.5 g) was purified by column chromatography over silica gel (SiO$_2$ 15-40 μm, eluent: CH$_2$Cl$_2$/CH$_3$OH/NH$_4$OH: 99/1/0.1). The pure fractions were collected and the solvent was evaporated. Products were crystallized from MeOH to afford 0.088 g of compound 30 (dia A; yield: 4%, mp: 159° C.) and 0.110 g of compound 29 (dia B; yield: 5%, mp: 186° C.).

Example B8 a. Preparation of Compounds 51 and 52

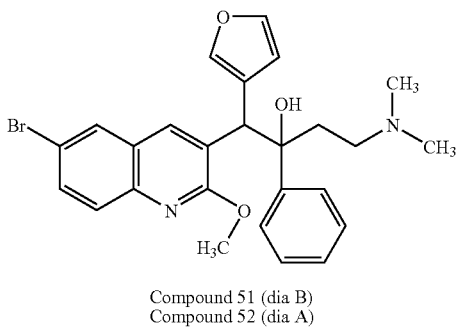

Compound 51 (dia B)
Compound 52 (dia A)

Lithium diisopropylamine (1.7 ml of a 2.0 M solution in THF/heptane; 0.0034 mol) was dissolved in THF (10 ml; dry) and cooled with an ice-bath at −70° C. Intermediate 25 (0.836 g, 0.0026 mol) was added dropwise as a solution in THF (8 ml; dry) and the mixture was stirred for 2 hours at −70° C. Then 3-(dimethylamino)-1-phenyl-1-propanone (0.466 g, 0.0026 mol) was added dropwise as a solution in THF (3.72 ml; dry) and the reaction mixture was stirred for 3 hours at −70° C. Then H$_2$O was added (quenching) at −70° C., followed by EtOAc. The layers were separated and the organic layer was washed with brine, dried (MgSO$_4$), filtered and the solvent was evaporated. Column purification: The residue was purified by flash chromatography (eluent: cyclohexane/2-propanol/NH$_4$OH 97/3/0.2). The desired fractions were collected and the solvent was evaporated. Yield: 0.081 g of compound 52 (dia A; 3.6%) and compound 51 (dia B; 6%).

b. Preparation of Compounds 53 and 54

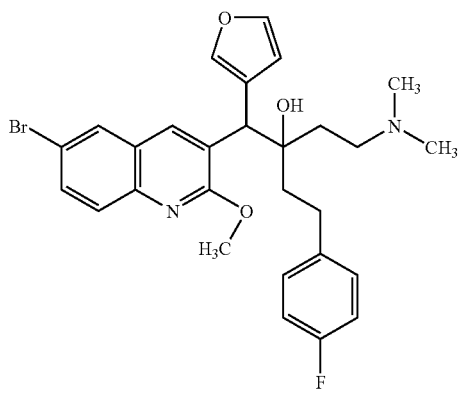

Compound 53 (dia A)
Compound 54 (dia B)

Compounds 53 and 54 were prepared according to the procedure for compounds 51 and 52 as described in B8.a, starting from 1-(dimethylamino)-5-(4-fluorophenyl)-3-pentanone (prepared in the same way as described in J. Am. Chem. Soc., 1950, 72, 718-721). Column purification: The residue was purified by column chromatography over silica gel (eluent: CH$_2$Cl$_2$/CH$_3$OH/NH$_4$OH 96/4/0.4 to 91/9/0.9; 10 μm). Two fractions were collected and the solvent was evaporated. Yield: Compound 53 (12%; mp: 122° C.; dia A) and compound 54 (12%; mp: 129° C.; dia B).

Example B9 a. Preparation of Compounds 34 and 33

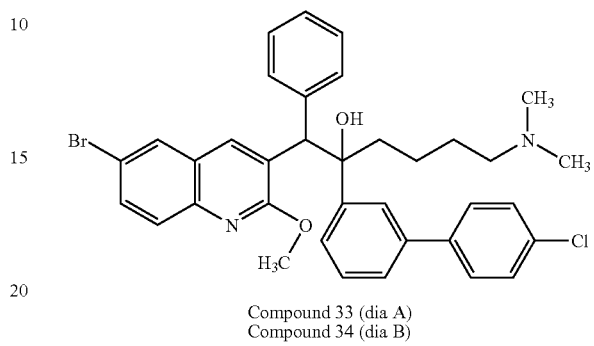

Compound 33 (dia A)
Compound 34 (dia B)

nBuLi 1.6 M in hexane (8.6 ml, 0.014 mol) was added slowly at −20° C. under N$_2$ flow to a solution of diisopropylamine (1.9 ml, 0.014 mol) in THF (5 ml). The mixture was stirred at −20° C. for 20 minutes, then cooled at −70° C. A solution of 6-bromo-2-methoxy-3-(phenylmethyl)-quinoline (1.81 g, 0.0055 mol) in THF (15 ml) was added slowly. The mixture was stirred at −70° C. for 90 minutes. A solution of intermediate 27 (2.27 g, 0.0072 mol) in THF (20 ml) was added slowly. The mixture was stirred at −70° C. for 1 hour, hydrolyzed at −30° C. with ice water, and extracted with EtOAc. The organic layer was separated, dried over MgSO$_4$, filtered, and the solvent was evaporated. The residue (4.3 g) was purified by column chromatography (eluent: CH$_2$Cl$_2$/CH$_3$OH/NH$_4$OH 95/5/0.5). Two fractions were collected and the solvent was evaporated. Both fractions were crystallized separately from diisopropylether, yielding 0.049 g of compound 33 (diastereoisomer A; yield 3%) as a white solid and 0.32 g of compound 34 (diastereoisomer B; yield 2%) as a white solid.

b. Preparation of Compounds 31 and 32

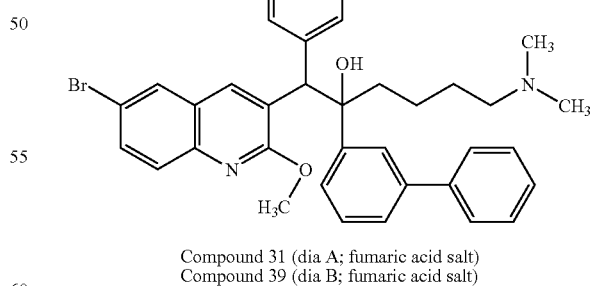

Compound 31 (dia A; fumaric acid salt)
Compound 39 (dia B; fumaric acid salt)

Compounds 31 and 32 were prepared according to the procedure for compounds 33 and 34 as described in B9.a, but using intermediate 28 (instead of intermediate 27) and using a different column procedure: The residue was purified by column chromatography over silica gel (eluent: CH$_2$Cl$_2$/CH$_3$OH/NH$_4$OH 96/4/0.5; 15-40 μm). Two fractions were collected and the solvent was evaporated. Fraction 1 was crystallized from 2-propanone/2-butenedioic acid (E), to obtain the fumaric acid salt. The precipitate was filtered off and dried. Yield: Compound 31 (86 mg; dia A; fumaric acid salt). Fraction 2 was crystallized from 2-propanone/2-butenedioic acid (E), to obtain the fumaric acid salt. The precipitate was filtered off and dried. Yield: Compound 32 (72 mg; dia B; fumaric acid salt).

c. Preparation of Compounds 38 and 39

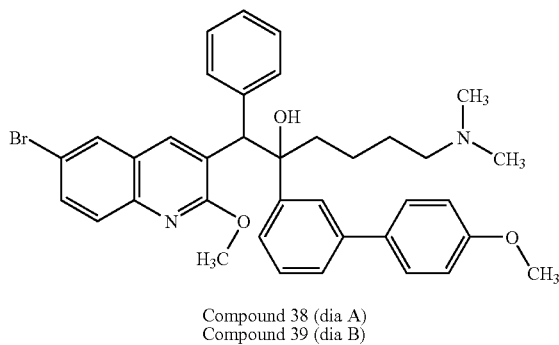

Compound 38 (dia A)
Compound 39 (dia B)

Compounds 38 and 39 were prepared according to the procedure for compounds 33 and 34 as described in B9.a, but using intermediate 29 (instead of intermediate 27) and using a different column procedure: The residue was purified by column chromatography over kromasil (eluent: $CH_2Cl_2$/$CH_3OH$/$NH_4OH$ from 97/3/0.3 to 95/5/0.5; 10 μm). Two impure fractions of dia A and dia B were collected and the solvent was evaporated. The dia A and dia B fractions were purified separately by reversed phase chromatography (Xbridge™ C18 column from Waters (5 μm; 30×150 mm) with a flow rate of 40 ml/min. Two mobile phases (mobile phase A: 100% methanol; mobile phase B: 100% 63 mM ammonium hydrogen carbonate (5 g/l) pH=10.2 (in ultra pure water) were employed to run a gradient condition from 90% A, 10% B to 100% A in 14 minutes, and reequilibrated with initial conditions for 6 minutes. Fraction 1 was crystallized from DIPE. The precipitate was filtered off and dried. Yield: Compound 38 (216 mg; 5%; dia A). Fraction 2 was crystallized from DIPE. The precipitate was filtered off and dried. Yield: Compound 39 (281 mg; 6%; dia B).

d. Preparation of Compounds 40 and 42

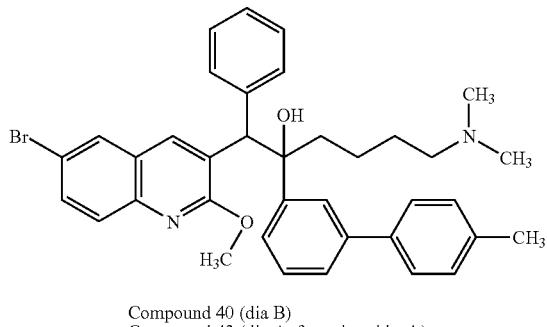

Compound 40 (dia B)
Compound 42 (dia A; fumaric acid salt)

Compounds 40 and 42 were prepared according to the procedure for compounds 33 and 34 as described in B9.a, but using intermediate 30 (instead of intermediate 27) and using a different column procedure: The residue was purified by column chromatography over kromasil (eluent: $CH_2Cl_2$/$CH_3OH$/$NH_4OH$ 97/3/0.1; 10 μm). Two fractions were collected and the solvent was evaporated. Fraction 1 was crystallized from 2-propanone/2-butenedioic acid (E), to obtain the fumaric acid salt. The precipitate was filtered off and dried. Yield: Compound 42 (485 mg; 10%; dia A; fumaric acid salt). Fraction 2 was crystallized from DIPE. The precipitate was filtered off and dried. Yield: Compound 40 (295 mg; 7%; dia B).

e. Preparation of Compounds 35 and 36

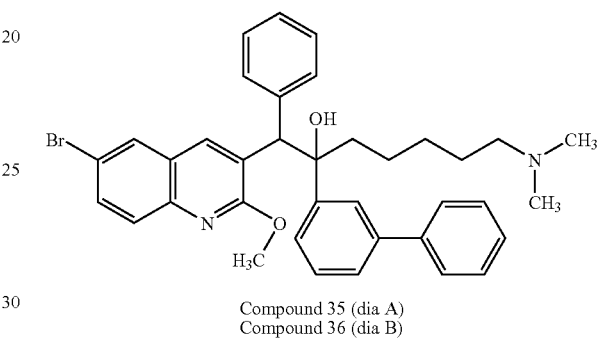

Compound 35 (dia A)
Compound 36 (dia B)

Compounds 35 and 36 were prepared according to the procedure for compounds 33 and 34 as described in B9.a, but using intermediate 35 (instead of intermediate 27) and using a different column procedure: The residue was purified by column chromatography over kromasil (eluent: $CH_2Cl_2$/$CH_3OH$/$NH_4OH$ 97/3/0.5; 10 μm). Two fractions were collected and the solvent was evaporated. Fraction 1 and fraction 2 were both purified by SFC chiral chromatography (2-ethylpyridine 150×21 mm, eluent: $CO_2$/MeOH/2-propylamine 85/15/0.3). Yield: Compound 35 (15 mg; dia A) and compound 36 (21 mg; dia B).

f. Preparation of Compounds 37 and 56

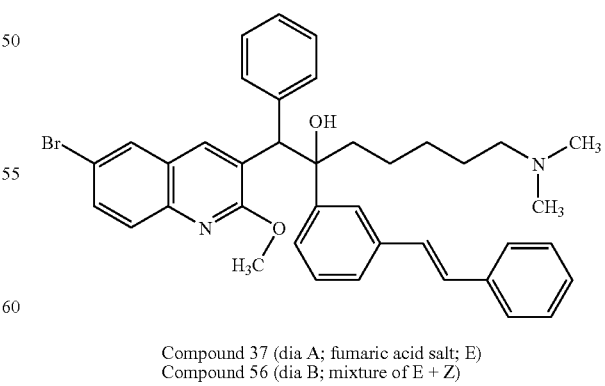

Compound 37 (dia A; fumaric acid salt; E)
Compound 56 (dia B; mixture of E + Z)

Compound 37 was prepared according to the procedure for compounds 33 and 34 as described in B9.a, but using intermediate 36 (instead of intermediate 27) and using a different column procedure: The residue was purified by column chromatography over kromasil (eluent: $CH_2Cl_2/CH_3OH/NH_4OH$ 95/5/0.5; 10 μm). The first fraction was collected and the solvent was evaporated. Fraction 1 was crystallized from 2-propanone/2-butenedioic acid (E), to obtain the fumaric acid salt. The precipitate was filtered off and dried. Yield: 230 mg of compound 37 (Dia A; fumaric acid salt; (E)). Fraction 2 was crystallized from DIPE. The precipitate was filtered off and dried.

Yield: 16 mg of compound 56 (Dia B; (E)+6% (Z)).

Example B10

Preparation of Compounds 41, 45, 46, 47, 44 and 55

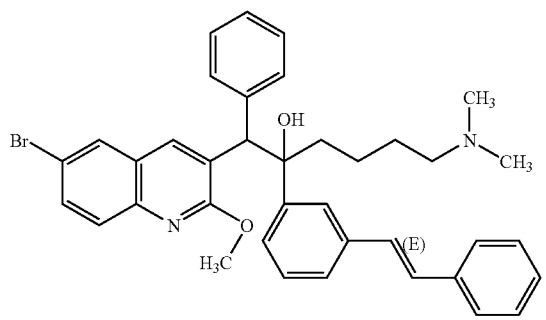

Compound 55 (Dia A)
Compound 41 (Dia B)
Compound 45 (A1)
Compound 46 (A2)
Compound 47 (B1; fumaric acid salt)
Compound 44 (B2; fumaric acid salt)

Compounds 45, 46, 47 and 44 were prepared according to the procedure for compounds 33 and 34 as described B9.a, but using intermediate 31 (instead of intermediate 27) and using a different column procedure. The residue was purified by column chromatography over silica gel (eluent: $CH_2Cl_2/CH_3OH/NH_4OH$ 97/3/0.3; 15-40 μm). Two fractions were collected and the solvent was evaporated, yielding 2.6 g of compound 55 (22%; Dia A (E) (Fraction 1)) and 3.0 g of compound 41 (25%; Dia B (E)(Fraction 2).

To obtain the corresponding enantiomers, compound 55 was purified by SFC (Supercritical Fluid Chromatography) chiral chromatography (ChiralPak AD-H, 250×21 mm, eluent: $CO_2$/2-propanol/2-propylamine 60/40/0.3). Two fractions were collected and the solvent was evaporated, yielding 0.673 g of compound 45 (enantiomer A1; yield 6%) and 0.712 g of compound 46 (enantiomer A2; yield 6%). To obtain the corresponding enantiomers, compound 41 was purified by SFC chiral chromatography (ChiralPak AD-H 250×21 mm, eluent: $CO_2$/2-propanol/2-propylamine 70/30/0.3). Two fractions were collected and the solvent was evaporated. The enantiomer B1 was crystallized from the first fraction from 2-propanone/2-butenedioic acid (E), to obtain the fumaric acid salt. The precipitate was filtered off and dried. Yield: 0.690 g of compound 47 (enantiomer B1; yield 4%; fumaric acid salt). The enantiomer B2 was crystallized from the second fraction from 2-propanone/2-butenedioic acid (E), to obtain the fumaric acid salt. The precipitate was filtered off and dried. Yield: 1.489 g of compound 44 (Yield: 10%; fumaric acid salt; B2).

Tables 1 to 4 list compounds of formula (Ia) according to the present invention and which were prepared according to one of the above procedures (Ex. No.).

For a number of compounds, melting points were obtained with a Kofler hot bench, consisting of a heated plate with linear temperature gradient, a sliding pointer and a temperature scale in degrees Celsius.

TABLE 1

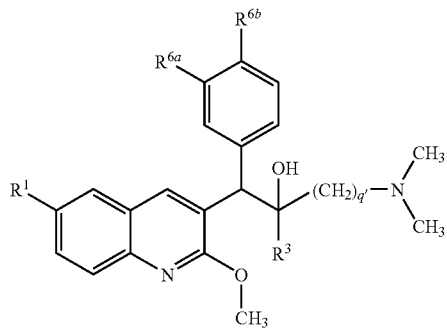

| Comp. nr. | Ex. nr. | $R^1$ | $R^3$ | $R^{6a}$ | $R^{6b}$ | q' | Stereochemistry, melting points and salt forms |
|---|---|---|---|---|---|---|---|
| 1 | B4.b | ----Br | 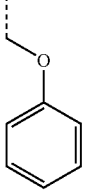 | ----H | ----H | 4 | dia A; 148° C. |

TABLE 1-continued
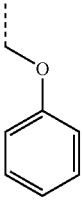
| Comp. nr. | Ex. nr. | R¹ | R³ | R⁶ᵃ | R⁶ᵇ | q' | Stereochemistry, melting points and salt forms |
|---|---|---|---|---|---|---|---|
| 2 | B4.b | —Br | 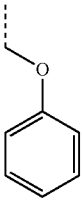 | —H | —H | 4 | dia B; 151° C. |
| 3 | B1 | —Br | 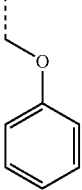 | —H | —Cl | 4 | dia A |
| 4 | B1 | —Br | 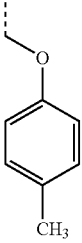 | —H | —Cl | 4 | dia B; 118° C. |
| 5 | B4.e | —Br | 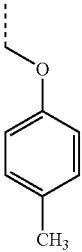 | —H | —H | 4 | dia A; 146° C. |
| 6 | B4.e | —Br | 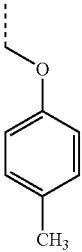 | —H | —H | 4 | dia B; 130° C. |

TABLE 1-continued
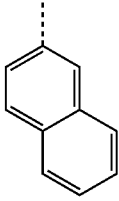
| Comp. nr. | Ex. nr. | R¹ | R³ | R⁶ᵃ | R⁶ᵇ | q' | Stereochemistry, melting points and salt forms |
|---|---|---|---|---|---|---|---|
| 7 | B5.e | ----H | naphthalen-2-yl | ----H | pyridin-3-yl | 4 | dia A |
| 7b | B5.e | ----H | naphthalen-2-yl | ----H | pyridin-3-yl | 4 | dia B; 192° C. |
| 8 | B5.d | ----H | naphthalen-2-yl | pyridin-4-yl | ----H | 4 | dia A |
| 9 | B5.d | ----H | naphthalen-2-yl | pyridin-4-yl | ----H | 4 | dia B |
| 10 | B5.c | ----H | naphthalen-2-yl | ----H | 1-methyl-1H-pyrazol-4-yl | 4 | dia B; 190° C. |

TABLE 1-continued
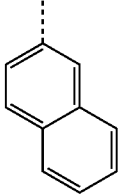
| Comp. nr. | Ex. nr. | R¹ | R³ | R⁶ᵃ | R⁶ᵇ | q' | Stereochemistry, melting points and salt forms |
|---|---|---|---|---|---|---|---|
| 11 | B5.c | ----H | 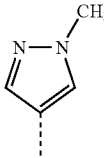 | ----H | 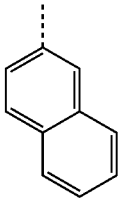 | 4 | dia A |
| 12 | B5.b | ----H |  | ----H | 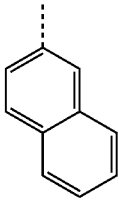 | 4 | dia B |
| 13 | B5.b | ----H | 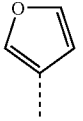 | ----H | 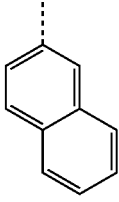 | 4 | diaA; m.p. 197° C. |
| 14 | B5.a | ----H | 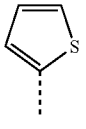 | ----H | 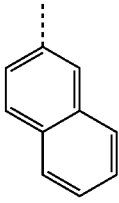 | 4 | dia A |
| 15 | B5.a | ----H | 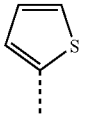 | ----H | | 4 | dia B |

TABLE 1-continued
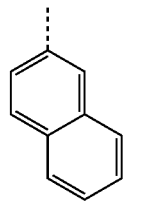
| Comp. nr. | Ex. nr. | R¹ | R³ | R⁶ᵃ | R⁶ᵇ | q' | Stereochemistry, melting points and salt forms |
|---|---|---|---|---|---|---|---|
| 16 | B5.f | ----H | 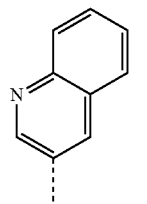 | 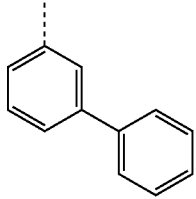 | ----H | 4 | dia B; 141° C. |
| 31 | B9.b | ----Br | 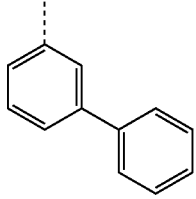 | ----H | ----H | 4 | dia A; 119° C. fumaric acid salt |
| 32 | B9.b | ----Br | 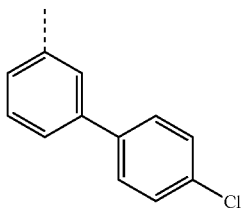 | ----H | ----H | 4 | dia B; 139° C. fumaric acid salt |
| 33 | B9.a | ----Br | 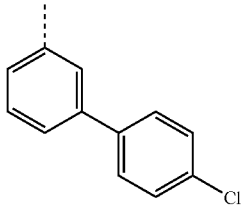 | ----H | ----H | 4 | dia A; 159° C. |
| 34 | B9.a | ----Br |  | ----H | ----H | 4 | dia B; 147° C. |

TABLE 1-continued
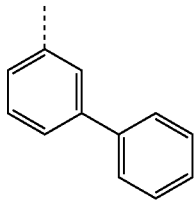
| Comp. nr. | Ex. nr. | R¹ | R³ | R⁶ᵃ | R⁶ᵇ | q' | Stereochemistry, melting points and salt forms |
|---|---|---|---|---|---|---|---|
| 35 | B9.e | ----Br | 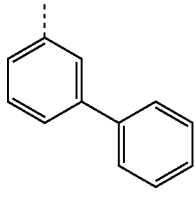 | ----H | ----H | 5 | dia A |
| 36 | B9.e | ----Br | 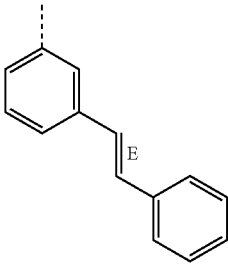 | ----H | ----H | 5 | dia B |
| 37 | B9.f | ----Br | 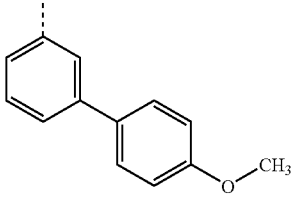 | ----H | ----H | 5 | dia A; (E); 155° C. fumaric acid salt |
| 38 | B9.c | ----Br | 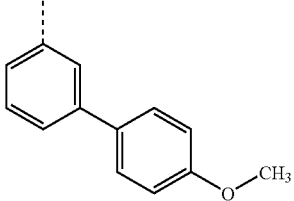 | ----H | ----H | 4 | dia A; 146° C. |
| 39 | B9.c | ----Br |  | ----H | ----H | 4 | dia B; 139° C. |

TABLE 1-continued

| Comp. nr. | Ex. nr. | R¹ | R³ | R⁶ᵃ | R⁶ᵇ | q' | Stereochemistry, melting points and salt forms |
|---|---|---|---|---|---|---|---|
| 40 | B9.d | —Br | 4'-methyl-biphenyl-3-yl | —H | —H | 4 | dia B; 157° C. |
| 41 | B10 | —Br | 3-(E-styryl)phenyl | —H | —H | 4 | dia B; (E); 153° C. |
| 55 | B10 | —Br | 3-(E-styryl)phenyl | —H | —H | 4 | dia A; (E); 159° C. |
| 42 | B9.d | —Br | 4'-methyl-biphenyl-3-yl | —H | —H | 4 | dia A; 121° C. fumaric acid salt |
| 43 | B5.g | —H | naphthalen-2-yl | —H | pyridin-4-yl | 4 | dia A |

TABLE 1-continued

[Structure: quinoline core with R¹ at 6-position, 2-methoxy group, 3-position bearing CH(Ar)-C(OH)(R³)-(CH₂)q'-N(CH₃)₂, where Ar has R⁶ᵃ and R⁶ᵇ substituents]

| Comp. nr. | Ex. nr. | R¹ | R³ | R⁶ᵃ | R⁶ᵇ | q' | Stereochemistry, melting points and salt forms |
|---|---|---|---|---|---|---|---|
| 44 | B10 | —Br | 3-styryl-phenyl (E) | —H | —H | 4 | B2; (E), 140° C. fumaric acid salt |
| 45 | B10 | —Br | 3-styryl-phenyl (E) | —H | —H | 4 | A1; (E); 107° C. |
| 46 | B10 | —Br | 3-styryl-phenyl (E) | —H | —H | 4 | A2; (E); 109° C. |
| 47 | B10 | —Br | 3-styryl-phenyl (E) | —H | —H | 4 | B1; (E); 142° C. fumaric acid salt |

TABLE 1-continued

| Comp. nr. | Ex. nr. | R¹ | R³ | R⁶ᵃ | R⁶ᵇ | q' | Stereochemistry, melting points and salt forms |
|---|---|---|---|---|---|---|---|
| 48 | B5.g | ----H | 2-naphthyl | ----H | 4-pyridyl | 4 | dia B; 210° C. |
| 49 | B5.h | ----H | 2-naphthyl | ----H | 3-quinolinyl | 4 | dia B |
| 50 | B5.h | ----H | 2-naphthyl | ----H | 3-quinolinyl | 4 | dia A |
| 56 | B9.f | ----Br | 3-styrylphenyl (E+Z) | ----H | ----H | 5 | dia B; (E) + 6% (Z) |

TABLE 2
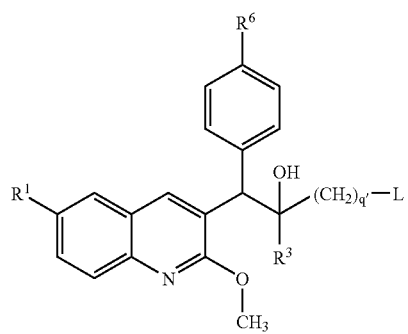
| Comp. nr. | Ex. nr. | R$^1$ | R$^3$ | R$^6$ | q' | L | Stereochemistry and melting points |
|---|---|---|---|---|---|---|---|
| 19 | B4.c | —Br | 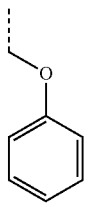 | —H | 4 | 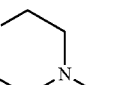 | dia A |
| 20 | B4.c | —Br | 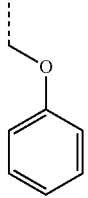 | —H | 4 | 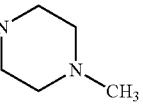 | dia B; 144° C. |
| 21 | B2 | —Br | 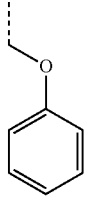 | —Cl | 4 | 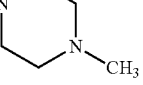 | dia A |
| 22 | B2 | —Br | 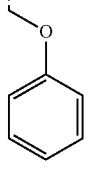 | —Cl | 4 | 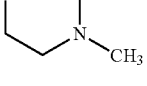 | dia B |
| 23 | B4.d | —Br | 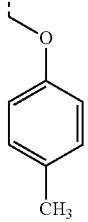 | —H | 4 | 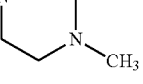 | dia A |

TABLE 2-continued

| Comp. nr. | Ex. nr. | R¹ | R³ | R⁶ | q' | L | Stereochemistry and melting points |
|---|---|---|---|---|---|---|---|
| 24 | B4.d | —Br | -CH₂-O-(4-methylphenyl) | —H | 4 | 4-methylpiperazin-1-yl | dia B; 168° C. |
| 25 | B4.a | —Br | -CH₂-O-benzyl | —H | 4 | piperidin-1-yl | dia A |
| 26 | B4.a | —Br | -CH₂-O-benzyl | —H | 4 | piperidin-1-yl | dia B |
| 27 | B3 | —Br | -CH₂-O-benzyl | —H | 4 | 4-methylpiperazin-1-yl | dia A |
| 28 | B3 | —Br | -CH₂-O-benzyl | —H | 4 | 4-methylpiperazin-1-yl | dia B; 122° C. |

TABLE 3

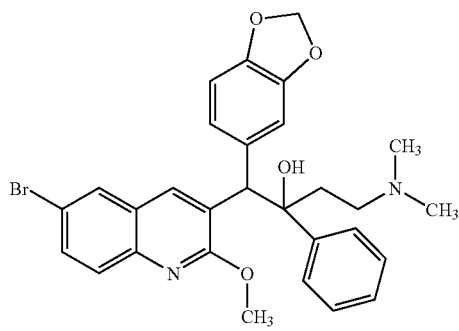

| Comp. nr. | Ex. nr. | Stereochemistry and melting points |
|---|---|---|
| 29 | B7 | dia B; 185-186° C. |
| 30 | B7 | dia A; 158-159° C. |

TABLE 4

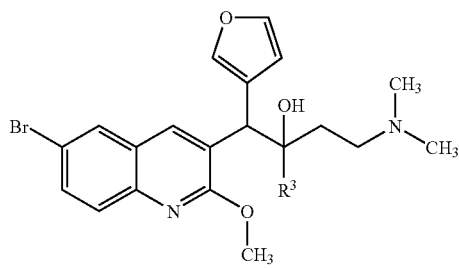

| Comp. nr. | Ex. nr. | R³ | Stereochemistry and melting points |
|---|---|---|---|
| 51 | B8.a | 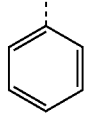 | dia B |
| 52 | B8.a | 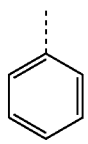 | dia A |
| 53 | B8.b | 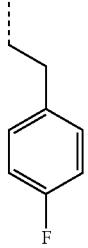 | dia A; 122° C. |

TABLE 4-continued

| 54 | B8.b | | dia B; 129° C. |
|---|---|---|---|

Analytical Methods
LCMS

The mass of some compounds was recorded with LCMS (liquid chromatography mass spectrometry). The methods used are described below.

General Procedure A

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3.15 kV and the source temperature was maintained at 110° C. on the ZQ™ (simple quadrupole Zspray™ mass spectrometer from Waters). Nitrogen was used as the nebulizer gas. Data acquisition was performed with a Waters-Micromass MassLynx-Openlynx data system.

General Procedure B

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

General Procedure C

The HPLC measurement was performed using an Agilent 1100 series liquid chromatography system comprising a binary pump with degasser, an autosampler, a column oven, a UV detector and a column as specified in the respective methods below. Flow from the column was split to a MS spectrometer. The MS detector was configured with an electrospray ionization source. The capillary voltage was 3 kV, the quadrupole temperature was maintained at 100° C. and the desolvation temperature was 300° C. Nitrogen was used as the nebulizer gas. Data acquisition was performed with an Agilent Chemstation data system.

General Procedure D

The LC measurement was performed using a HPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method 1

In addition to general procedure A: Reversed phase HPLC was carried out on a Sunfire C18 column (3.5 μm, 4.6×100 mm) with an initial flow rate of 0.8 ml/min. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A (hold for 1 minute) to 100% B in 4 minutes, hold at 100% B at a flow rate of 1.2 ml/min for 4 minutes and reequilibrated with initial conditions for 3 minutes. An injection volume of 10 μl was used. Cone voltage was 20 V for positive and negative ionization mode. Mass spectra were acquired by scanning from 100 to 1000 in 0.4 seconds using an interscan delay of 0.3 seconds.

Method 2

In addition to general procedure A: Reversed phase HPLC was carried out on a Sunfire C18 column (3.5 μm, 4.6×100 mm) with an initial flow rate of 0.8 ml/min. Two mobile phases (mobile phase A: 25% 7 mM ammonium acetate+50% acetonitrile+25% formic acid (2 ml/l); mobile phase B: 100% acetonitrile) were employed to run a gradient condition from 100% A (hold for 1 minute) to 100% B in 4 minutes, hold at 100% B at a flow rate of 1.2 ml/min for 4 minutes and reequilibrated with initial conditions for 3 minutes). An injection volume of 10 μl was used. Cone voltage was 20 V for positive and negative ionization mode. Mass spectra were acquired by scanning from 100 to 1000 in 0.4 seconds using an interscan delay of 0.3 seconds.

Method 3

In addition to general procedure B: Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

Method 4

In addition to general procedure C: Reversed phase HPLC was carried out on a YMC-Pack ODS-AQ C18 column (4.6×50 mm) with a flow rate of 2.6 ml/min. A gradient run was used from 95% water and 5% acetonitrile to 95% acetonitrile in 7.30 minutes and was hold for 1.20 minutes. Mass spectra were acquired by scanning from 100 to 1000. Injection volume was 10 μl. Column temperature was 35° C.

Method 5

In addition to general procedure A: Reversed phase HPLC was carried out on a Sunfire C18 column (3.5 μm, 4.6×100 mm) with an initial flow rate of 0.8 ml/min. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A (hold for 1 minute) to 100% B in 4 minutes, hold at 100% B at a flow rate of 1.2 ml/min for 4 minutes and reequilibrated with initial conditions for 3 minutes. An injection volume of 10 μl was used. Positive ionization mode was used with four different cone voltages (20, 40, 50, 55 V). Mass spectra were acquired by scanning from 100 to 1000 in 0.4 seconds using an interscan delay of 0.1 seconds.

Method 6

In addition to general procedure D: Reversed phase HPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltages were 20, 30, 45, 60 V for positive ionization mode. Mass spectra were acquired by scanning from 100 to 1000 in 0.2 seconds using an interscan delay of 0.1 seconds.

Method 7

In addition to general procedure D: Reversed phase HPLC was carried out on a Thermo Hypersil Gold C18 column (1.9 μm, 2.1×100 mm) with a flow rate of 0.40 ml/min. Two mobile phases (mobile phase A: 95% 7 mM ammonium acetate/5% acetonitrile; mobile phase B: 100% acetonitrile) were employed to run a gradient condition from 72% A and 28% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltages were 20, 30, 45, 60 V for positive ionization mode. Mass spectra were acquired by scanning from 100 to 1000 in 0.2 seconds using an interscan delay of 0.1 seconds.

Method 8

In addition to general procedure D: Reversed phase HPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 100% 7 mM ammonium acetate; mobile phase B: 100% acetonitrile) were employed to run a gradient condition from 75% A and 25% B (hold for 0.5 minutes) to 8% A and 92% B in 3.5 minutes, hold for 2 minutes and reequilibrated with initial conditions for 2 minutes. An injection volume of 2 μl was used. Cone voltages were 20, 30, 45, 60 V for positive ionization mode. Mass spectra were acquired by scanning from 100 to 1000 in 0.2 seconds using an interscan delay of 0.1 seconds.

Method 9

In addition to general procedure D: Reversed phase HPLC was carried out on a Thermo Hypersil Gold C18 column (1.9 μm, 2.1×100 mm) with a flow rate of 0.50 ml/min. Two mobile phases (mobile phase A: 95% 7 mM ammonium acetate/5% acetonitrile; mobile phase B: 100% acetonitrile) were employed to run a gradient condition from 40% A and 60% B (hold for 0.5 minutes) to 5% A and 95% B in 3.5 minutes, hold for 2 min and back to the initial conditions in 0.5 min, hold for 1.5 minutes. An injection volume of 2 μl was used. Cone voltages were 20, 30, 45, 60 V for positive ionization mode. Mass spectra were acquired by scanning from 100 to 1000 in 0.2 seconds using an interscan delay of 0.1 seconds.

Method 10

In addition to general procedure A: Reversed phase HPLC was carried out on a Varian Pursuit Diphenyl column (5 μm, 4×100 mm) with a flow rate of 0.8 ml/min. Two mobile phases (mobile phase A: 100% 7 mM ammonium acetate; mobile phase B: 100% acetonitrile) were employed to run a gradient condition from 80% A, 20% B (hold for 0.5 minutes) to 90% B in 4.5 minutes, 90% B for 4 minutes and reequilibrated with initial conditions for 3 minutes. An injection volume of 10 μl was used. Cone voltages were 20, 40, 50, 55 V for positive ionization mode. Mass spectra were acquired by scanning from 100 to 1000 in 0.3 seconds using an interscan delay of 0.05 seconds.

When a compound is a mixture of isomers which give different peaks in the LCMS method, only the retention time of the main component is given in the LCMS table.

TABLE 5

LCMS: (MH⁺), protonated molecular ion (of the free base), and retention time ($R_t$, in minutes)

| Compound No | LCMS method | (MH⁺) | $R_t$ (min) |
|---|---|---|---|
| 1 | 2 | 563 | 3.79 |
| 2 | 2 | 563 | 3.82 |
| 3 | 1 | 597 | 5.35 |
| 4 | 1 | 597 | 5.43 |
| 5 | 1 | 577 | 5.26 |
| 6 | 1 | 577 | 5.31 |
| 7 | 3 | 582 | 1.11 |
| 7b | 4 | 582 | 3.28 |
| 8 | 4 | 582 | 2.81 |
| 9 | 4 | 582 | 2.98 |
| 10 | 5 | 585 | 4.67 |
| 11 | 5 | 585 | 4.45 |
| 12 | 5 | 571 | 5.02 |
| 13 | 5 | 571 | 5.10 |
| 14 | 4 | 587 | 4.37 |
| 15 | 4 | 587 | 4.36 |
| 16 | 5 | 632 | 5.12 |
| 19 | 2 | 618 | 3.39 |
| 20 | 2 | 618 | 3.45 |
| 21 | 1 | 652 | 5.40 |
| 22 | 1 | 652 | 5.38 |
| 23 | 1 | 632 | 5.18 |
| 24 | 1 | 632 | 5.21 |
| 25 | 1 | 617 | 5.20 |
| 26 | 1 | 617 | 5.21 |
| 27 | 1 | 632 | 4.96 |
| 28 | 1 | 632 | 4.95 |
| 29 | 3 | 549 | 1.21 |
| 30 | 3 | 549 | 1.19 |
| 31 | 5 | 609 | 5.45 |
| 32 | 5 | 609 | 5.45 |
| 33 | 6 | 643 | 5.85 |
| 34 | 6 | 643 | 5.96 |
| 35 | 7 | 623 | 5.79 |
| 36 | 7 | 623 | 5.76 |
| 37 | 7 | 649 | 5.46 |
| 38 | 8 | 639 | 4.84 |
| 39 | 8 | 639 | 4.80 |
| 40 | 8 | 623 | 5.44 |
| 41 | 8 | 635 | 5.39 |
| 42 | 6 | 623 | 5.34 |
| 43 | 7 | 582 | 3.75 |
| 44 | 9 | 635 | 3.57 |
| 45 | 9 | 635 | 3.62 |
| 46 | 9 | 635 | 3.63 |
| 47 | 9 | 635 | 3.84 |
| 48 | 7 | 582 | 3.72 |
| 49 | 10 | 632 | 10.25 |
| 50 | 10 | 632 | 11.12 |
| 51 | 6 | 495 | 5.25 |
| 52 | 6 | 495 | 5.34 |
| 53 | 7 | 541 | 4.04 |
| 54 | 7 | 541 | 4.02 |
| 55 | 6 | 635 | 5.50 |
| 56 | 9 | 649 | 4.18 |

Optical Rotation

The optical rotation was measured using a polarimeter. $[\alpha]_D^{20}$ indicates the optical rotation measured with light at the wavelength of the D-line of sodium (589 nm) at a temperature of 20° C. The cell pathlength is 1 dm. Behind the actual value the concentration and solvent of the solution which was used to measure the optical rotation are mentioned (see Table 6).

TABLE 6

Optical rotation data

| Comp. Nr. | $[\alpha]_D^{20}$ | Concentration | Solvent |
|---|---|---|---|
| 44 | −67.26 | 0.452 w/v % | DMF |
| 45 | +64.06 | 0.409 w/v % | DMF |
| 46 | −65.06 | 0.395 w/v % | DMF |
| 47 | +78.46 | 0.494 w/v % | DMF |

D. Pharmacological Examples

D.1. In-Vitro Method for Testing Compounds Against *M. tuberculosis*

Flat-bottom, sterile 96-well plastic microtiter plates were filled with 100 µl of Middlebrook (1×) broth medium. Subsequently, stock solutions (10× final test concentration) of compounds were added in 25 µl volumes to a series of duplicate wells in column 2 so as to allow evaluation of their effects on bacterial growth. Serial five-fold dilutions were made directly in the microtiter plates from column 2 to 11 using a customised robot system (Zymark Corp., Hopkinton, Mass.). Pipette tips were changed after every 3 dilutions to minimize pipetting errors with high hydrophobic compounds. Untreated control samples with (column 1) and without (column 12) inoculum were included in each microtiter plate. Approximately 5000 CFU per well of *Mycobacterium tuberculosis* (strain H37RV), in a volume of 100 µl in Middlebrook (1×) broth medium, was added to the rows A to H, except column 12. The same volume of broth medium without inoculum was added to column 12 in row A to H. The cultures were incubated at 37° C. for 7 days in a humidified atmosphere (incubator with open air valve and continuous ventilation). One day before the end of incubation, 6 days after inoculation, Resazurin (1:5) was added to all wells in a volume of 20 µl and plates were incubated for another 24 hours at 37° C. On day 7 the bacterial growth was quantitated fluorometrically.

The fluorescence was read in a computer-controlled fluorometer (Spectramax Gemini EM, Molecular Devices) at an excitation wavelength of 530 nm and an emission wavelength of 590 nm. The percentage growth inhibition achieved by the compounds was calculated according to standard methods and expressed as $IC_{90}$ (µg/ml) which defines the 90% inhibitory concentration for bacterial growth. The results are shown in Table 7.

D.2. In-Vitro Method for Testing Compounds for Anti-Bacterial Activity Against Strain *M. Smegmatis* ATCC607

Flat-bottom, sterile 96-well plastic microtiter plates were filled with 180 µl of sterile deionized water, supplemented with 0.25% BSA. Subsequently, stock solutions (7.8× final test concentration) of compounds were added in 45 µl volumes to a series of duplicate wells in column 2 so as to allow evaluation of their effects on bacterial growth. Serial five-fold dilutions (45 µl in 180 µl) were made directly in the microtiter plates from column 2 to 11 using a customised robot system (Zymark Corp., Hopkinton, Mass.). Pipette tips were changed after every 3 dilutions to minimize pipetting errors with high hydrophobic compounds. Untreated control samples with (column 1) and without (column 12) inoculum were included in each microtiter plate. Approximately 250 CFU per well of bacteria inoculum, in a volume of 100 µl in 2.8× Mueller-Hinton broth medium, was added to the rows A to H, except column 12. The same volume of broth medium without inoculum was added to column 12 in row A to H. The cultures were incubated at 37° C. for 48 hours in a humidified 5% $CO_2$ atmosphere (incubator with open air valve and continuous ventilation). At the end of incubation, two days after inoculation, the bacterial growth was quantitated fluorometrically. Therefore Alamar Blue (10×) was added to all wells in a volume of 20 μl and plates were incubated for another 2 hours at 50° C.

The fluorescence was read in a computer-controlled fluorometer (Cytofluor, Biosearch) at an excitation wavelength of 530 nm and an emission wavelength of 590 nm (gain 30). The percentage growth inhibition achieved by the compounds was calculated according to standard methods and expressed as $IC_{90}$ (μg/ml) which defines the 90% inhibitory concentration for bacterial growth. The results are shown in Table 7.

D.3. In-Vitro Method for Testing Compounds for Anti-Bacterial Activity Against Various Non-Mycobacterial Strains Preparation of Bacterial Suspensions for Susceptibility Testing:

The bacteria used in this study were grown overnight in flasks containing 100 ml Mueller-Hinton Broth (Becton Dickinson—cat. no. 275730) in sterile de-ionized water, with shaking, at 37° C. Stocks (0.5 ml/tube) were stored at −70° C. until use. Bacteria titrations were performed in microtiter plates to detect the $TCID_{50}$, in which the TCID50 represents the dilution that gives rise to bacterial growth in 50% of inoculated cultures.

In general, an inoculum level of approximately 100 $TCID_{50}$ was used for susceptibility testing.
Anti Bacterial Susceptibility Testing: $IC_{90}$ Determination Microtitre Plate Assay Flat-bottom, sterile 96-well plastic microtiter plates were filled with 180 μl of sterile deionized water, supplemented with 0.25% BSA. Subsequently, stock solutions (7.8× final test concentration) of compounds were added in 45 μl volumes in column 2. Serial five-fold dilutions (45 μl in 180 μl) were made directly in the microtiter plates from column 2 to reach column 11. Untreated control samples with (column 1) and without (column 12) inoculum were included in each microtiter plate. Depending on the bacteria type, approximately 10 to 60 CFU per well of bacteria inoculum (100 TCID50), in a volume of 100 μl in 2.8× Mueller-Hinton broth medium, was added to the rows A to H, except column 12. The same volume of broth medium without inoculum was added to column 12 in row A to H. The cultures were incubated at 37° C. for 24 hours under a normal atmosphere (incubator with open air valve and continuous ventilation). At the end of incubation, one day after inoculation, the bacterial growth was quantitated fluorometrically. Therefore resazurin (0.6 mg/ml) was added in a volume of 20 μl to all wells 3 hours after inoculation, and the plates were re-incubated overnight. A change in colour from blue to pink indicated the growth of bacteria. The fluorescence was read in a computer-controlled fluorometer (Cytofluor Biosearch) at an excitation wavelength of 530 nm and an emission wavelength of 590 nm. The % growth inhibition achieved by the compounds was calculated according to standard methods. The $IC_{90}$ (expressed in μg/ml) was defined as the 90% inhibitory concentration for bacterial growth. The results are shown in Table 7.
Agar Dilution Method.

$MIC_{99}$ values (the minimal concentration for obtaining 99% inhibition of bacterial growth) can be determined by performing the standard Agar dilution method according to NCCLS standards* wherein the media used includes Mueller-Hinton agar.

*Clinical laboratory standard institute. 2005. Methods for dilution Antimicrobial susceptibility tests for bacteria that grows Aerobically: approved standard-sixth edition Time Kill Assays Bactericidal or bacteriostatic activity of the compounds may be determined in a time kill assay using the broth microdilution method*. In a time kill assay on *Staphylococcus aureus* and methicillin resistant *S. aureus* (MRSA), the starting inoculum of *S. aureus* and MRSA is $10^6$ CFU/ml in Muller Hinton broth. The antibacterial compounds are used at the concentration of 0.1 to 10 times the MIC (i.e. $IC_{90}$ as determined in microtitre plate assay). Wells receiving no antibacterial agent constitute the culture growth control. The plates containing the microorganism and the test compounds are incubated at 37° C. After 0, 4, 24, and 48 hrs of incubation samples are removed for determination of viable counts by serial dilution ($10^{-1}$ to $10^{-6}$) in sterile PBS and plating (200 μl) on Mueller Hinton agar. The plates are incubated at 37° C. for 24 hrs and the number of colonies are determined. Killing curves can be constructed by plotting the $\log_{10}$ CFU per ml versus time. A bactericidal effect is commonly defined as 3-$\log_{10}$ decrease in number of CFU per ml as compared to untreated inoculum. The potential carryover effect of the drugs is removed by serial dilutions and counting the colonies at highest dilution used for plating.

*Zurenko, G. E. et al. In vitro activities of U-100592 and U-100766, novel oxazolidinone antibacterial agents. *Antimicrob. Agents Chemother.* 40, 839-845 (1996).

Determination of Cellular ATP Levels

In order to analyse the change in the total cellular ATP concentration (using ATP bioluminescence Kit, Roche), assays are carried out by growing a culture of *S. aureus* (ATCC29213) stock in 100 ml Mueller Hinton flasks and incubate in a shaker-incubator for 24 hrs at 37° C. (300 rpm). Measure $OD_{405}$ nm and calculate the CFU/ml. Dilute the cultures to $1 \times 10^6$ CFU/ml (final concentration for ATP measurement: $1 \times 10^5$ CFU/100 μl per well) and add test compound at 0.1 to 10 times the MIC (i.e. $IC_{90}$ as determined in microtitre plate assay). Incubate these tubes for 0, 30 and 60 minutes at 300 rpm and 37° C. Use 0.6 ml bacterial suspension from the snap-cap tubes and add to a new 2 ml eppendorf tubes. Add 0.6 ml cell lysis reagent (Roche kit), vortex at max speed and incubate for 5 minutes at room temperature. Cool on ice. Let the luminometer warm up to 30° C. (Luminoskan Ascent Labsystems with injector). Fill one column (=6 wells) with 100 μl of the same sample. Add 100 μl Luciferase reagent to each well by using the injector system. Measure the luminescence for 1 sec.

TABLE 7

$IC_{90}$ values (μg/ml).

| Comp. No. | STA 1 B29213 | SPN 1 6305 | MSM 1 ATCC607 |
|---|---|---|---|
| 3 | 9.5 | 11.9 | 1.7 |
| 22 | 32.7 | 11.6 | 8.2 |
| 21 | 2.1 | 2.6 | 2.1 |
| 4 | 1.9 | 2.4 | 1.9 |
| 27 | 4.5 | 2.2 | 2.0 |
| 26 | 2.0 | 2.0 | 2.0 |
| 28 | 10.0 | 12.6 | 4.5 |
| 1 | 8.9 | 8.9 | 2.2 |
| 2 | 4.5 | 2.2 | 1.8 |
| 19 | 4.4 | 2.5 | 2.0 |
| 20 | 49.1 | 9.8 | 9.8 |
| 23 | 2.0 | 2.0 | 2.0 |
| 24 | 39.9 | 10.0 | 10.0 |

TABLE 7-continued

| | IC$_{90}$ values (µg/ml). | | |
|---|---|---|---|
| Comp. No. | STA 1 B29213 | SPN 1 6305 | MSM 1 ATCC607 |
| 5 | 4.1 | 4.1 | 1.8 |
| 6 | 9.2 | 5.2 | 1.8 |
| 25 | 2.5 | 2.0 | 2.0 |
| 7 | 1.8 | 1.8 | 1.8 |
| 7b | 1.8 | 1.85 | 1.5 |
| 8 | 9.2 | 1.8 | 1.8 |
| 14 | 1.9 | 2.3 | 1.9 |
| 9 | 1.8 | 1.8 | 1.5 |
| 15 | 1.9 | 2.3 | 1.9 |
| 12 | 1.8 | 2.0 | 1.8 |
| 16 | 2.0 | 2.0 | 2.0 |
| 13 | 1.8 | 2.0 | 1.3 |
| 10 | 1.9 | 1.9 | 0.4 |
| 11 | 1.9 | 1.9 | 1.9 |
| 29 | 3.1 | 0.4 | 1.7 |
| 30 | 55.0 | 1.7 | 0.4 |
| 31 | 1.93 | 0.86 | 1.93 |
| 32 | 1.93 | 1.93 | 0.97 |
| 33 | 2.04 | 1.82 | 2.04 |
| 34 | 0.91 | 0.72 | 1.29 |
| 35 | 1.97 | | 1.76 |
| 36 | 1.97 | | 1.76 |
| 37 | 2.05 | | 1.63 |
| 38 | 2.02 | 2.02 | 10.14 |
| 39 | 2.02 | 2.02 | 2.02 |
| 40 | 1.97 | 1.97 | 7.85 |
| 41 | 2.01 | 2.01 | 0.40 |
| 42 | 2.21 | | 0.79 |
| 43 | 4.60 | | 0.37 |
| 44 | 1.79 | | 0.90 |
| 45 | 2.01 | | 2.01 |
| 46 | 2.01 | | 2.01 |
| 47 | 2.01 | | 2.01 |
| 48 | 1.84 | | 1.04 |
| 49 | 2.00 | | 2.00 |
| 50 | 25.15 | | 22.42 |
| 51 | 39.35 | | 1.57 |
| 52 | 49.54 | | 0.06 |
| 53 | 8.58 | | 1.71 |
| 54 | 8.58 | | 1.92 |
| 55 | 2.01 | 0.898 | 1.792 |

STA 29213 means *Staphylococcus aureus* (ATCC29213); SPN 6305 means *Streptococcus pneumoniae* (ATCC6305); MSM 607 means *M. Smegmatis* (ATCC607); ATCC means American type tissue culture.

The invention claimed is:

1. A compound of formula (Ia) or (Ib)

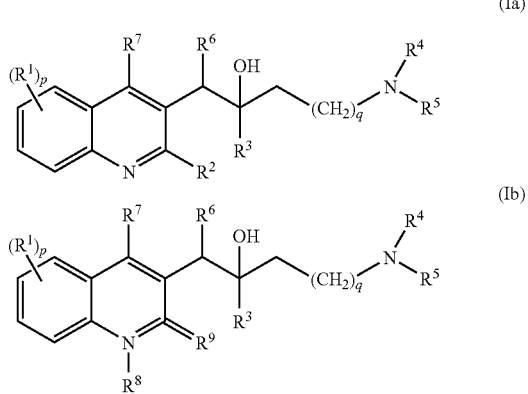

including any stereochemically isomeric form thereof, wherein

P is an integer equal to 1, 2, 3 or 4;

q is an integer equal to zero, 1, 2, 3 or 4;

$R^1$ is hydrogen, cyano, halo, alkyl, haloalkyl, hydroxy, alkyloxy, alkylthio, alkylthioalkyl, arylalkyl, di(aryl)alkyl or aryl;

$R^2$ is hydrogen, alkyloxy, aryl, aryloxy, hydroxy, mercapto, alkyloxyalkyloxy, alkylthio, mono or di(alkyl)amino, pyrrolidino or a radical of formula

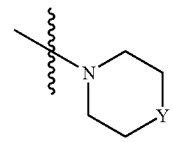

wherein Y is $CH_2$, O, S, NH or N-alkyl;

$R^3$ is alkyl, arylalkyl, aryl-O-alkyl, aryl-alkyl-O-alkyl, aryl, aryl-aryl, Het, Het-alkyl, Het-O-alkyl, Het-alkyl-O-alkyl or

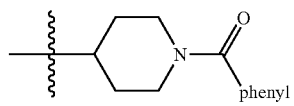

$R^4$ and $R^5$ each independently are hydrogen, alkyl or benzyl; or $R^4$ and $R^5$ together and including the N to which they are attached may form a radical selected from the group of pyrrolidinyl, pyrrolyl, imidazolidinyl, pyrazolidinyl, imidazolyl, pyrazolyl, triazolyl, piperidinyl, piperazinyl, imidazolidinyl, morpholinyl and thiomorpholinyl, each radical optionally substituted with alkyl, halo, haloalkyl, hydroxy, alkyloxy, amino, mono- or dialkylamino, alkylthio, alkyloxyalkyl, alkylthioalkyl and pyrimidinyl;

$R^6$ is aryl$^1$ or Het;

$R^7$ is hydrogen, halo, alkyl, aryl or Het;

$R^8$ is hydrogen or alkyl;

$R^9$ is oxo; or $R^8$ and $R^9$ together form the radical —CH═CH—N═;

aryl is a homocycle selected from phenyl, naphthyl, acenaphthyl or tetrahydronaphthyl, each being optionally substituted with 1, 2 or 3 substituents, each substituent being independently selected from hydroxy, halo, cyano, nitro, amino, mono- or dialkylamino, alkyl, $C_{2-6}$alkenyl optionally substituted with phenyl, haloalkyl, alkyloxy, haloalkyloxy, carboxyl, alkyloxycarbonyl, aminocarbonyl, morpholinyl or mono- or dialkylaminocarbonyl;

aryl$^1$ is a homocycle selected from phenyl, naphthyl, acenaphthyl or tetrahydronaphthyl, each being optionally substituted with 1, 2 or 3 substituents, each substituent being independently selected from hydroxy, halo, cyano, nitro, amino, mono- or dialkylamino, alkyl, haloalkyl, alkyloxy, alkylthio, haloalkyloxy, carboxyl, alkyloxycarbonyl, aminocarbonyl, morpholinyl, Het or mono- or dialkylaminocarbonyl;

Het is a monocyclic heterocycle selected from N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl or pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle being optionally substituted with 1, 2 or 3 substituents, each substituent independently selected from halo, hydroxy, alkyl or alkyloxy;

provided that if $R^3$ is alkyl, arylalkyl, aryl, Het, Het-alkyl or

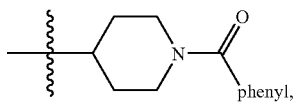

then $R^6$ is Het; phenyl substituted with Het; naphthyl substituted with Het; or acenaphthyl or tetrahydronaphthyl, each being optionally substituted with 1, 2 or 3 substituents, each substituent being independently selected from hydroxy, halo, cyano, nitro, amino, mono- or dialkylamino, alkyl, haloalkyl, alkyloxy, alkylthio, haloalkyloxy, carboxyl, alkyloxycarbonyl, aminocarbonyl, morpholinyl, Het or mono- or dialkylaminocarbonyl;

a N-oxide thereof or a pharmaceutically acceptable salt thereof.

2. A compound according to claim 1 wherein
$R^3$ is alkyl, arylalkyl, aryl-O-alkyl, aryl-alkyl-O-alkyl, aryl, Het, Het-alkyl, Het-O-alkyl, Het-alkyl-O-alkyl or

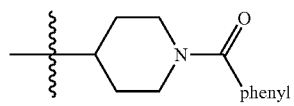

aryl is a homocycle selected from phenyl, naphthyl, acenaphthyl or tetrahydronaphthyl, each being optionally substituted with 1, 2 or 3 substituents, each substituent being independently selected from hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl or mono- or dialkylaminocarbonyl.

3. A compound according to claim 1 wherein alkyl represents $C_{1-6}$alkyl.

4. A compound according to claim 1 wherein $R^1$ is halo.

5. A compound according to claim 1 wherein p is equal to 1.

6. A compound according to claim 1 wherein $R^2$ is $C_{1-6}$alkyloxy.

7. A compound according to claim 6 wherein $R^2$ is methyloxy.

8. A compound according to claim 1 wherein $R^3$ is aryl-O—$C_{1-6}$alkyl, aryl$C_{1-6}$alkyl-O—$C_{1-6}$alkyl, aryl-aryl, Het-O—$C_{1-6}$alkyl or Het$C_{1-6}$alkyl-O—$C_{1-6}$alkyl.

9. A compound according to claim 8 wherein $R^3$ is aryl-O—$C_{1-6}$alkyl, aryl$C_{1-6}$alkyl-O—$C_{1-6}$alkyl, Het-O—$C_{1-6}$alkyl or Het$C_{1-6}$alkyl-O—$C_{1-6}$alkyl.

10. A compound according to claim 9 wherein $R^3$ is aryl-O—$C_{1-6}$alkyl or aryl$C_{1-6}$alkyl-O—$C_{1-6}$alkyl.

11. A compound according to claim 1 wherein $R^3$ is aryl.

12. A compound according claim 1 wherein q is equal to 1, 3 or 4.

13. A compound according to claim 1 wherein $R^4$ and $R^5$ represent $C_{1-6}$alkyl.

14. A compound according to claim 1 wherein $R^4$ and $R^5$ are taken together with the nitrogen atom to which they are attached and form a radical selected from the group consisting of piperidino or piperazino, each of said rings optionally substituted with $C_{1-6}$alkyl.

15. A compound according to claim 1 wherein $R^6$ is Het or optionally substituted phenyl.

16. A compound according to claim 1 wherein $R^7$ is hydrogen.

17. A compound according to claim 1 wherein the compound is a compound of formula (Ia).

18. A compound according to claim 1 wherein the compound is a compound of formula (Ia) wherein $R^1$ is hydrogen or halo; $R^2$ is $C_{1-6}$alkyloxy; $R^3$ is aryl-O—$C_{1-6}$alkyl, aryl$C_{1-6}$alkyl-O—$C_{1-6}$alkyl, aryl, or aryl-aryl; $R^4$ and $R^5$ are $C_{1-6}$alkyl; or $R^4$ and $R^5$ together with the nitrogen atom to which they are attached form a radical selected from the group consisting of piperidino or piperazino, each of said rings optionally substituted with $C_{1-6}$alkyl; $R^6$ is Het or optionally substituted phenyl; $R^7$ is hydrogen; q is 1, 3 or 4; p is 1.

19. A compound according to claim 1 wherein $R^1$ is placed in position 6 of the quinoline ring.

20. A compound according to claim 1 wherein the compound is selected from

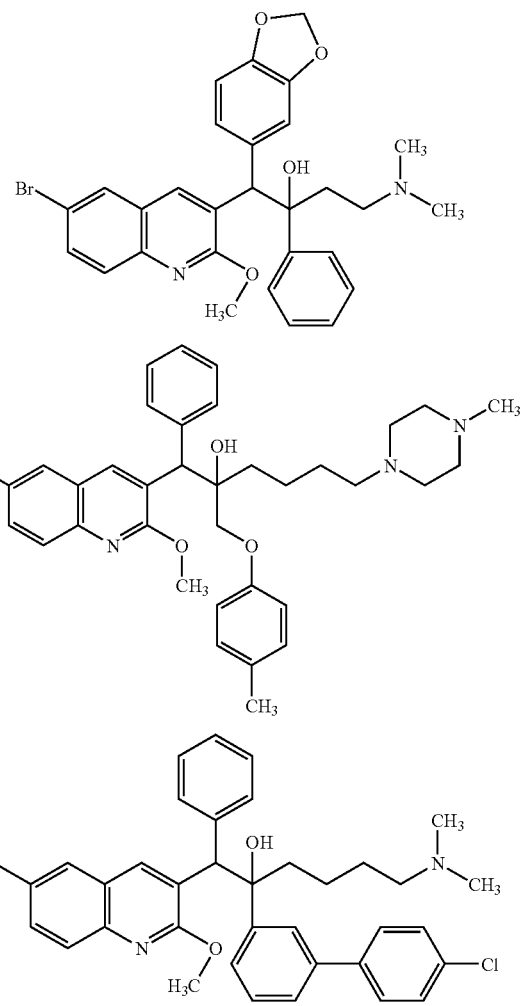

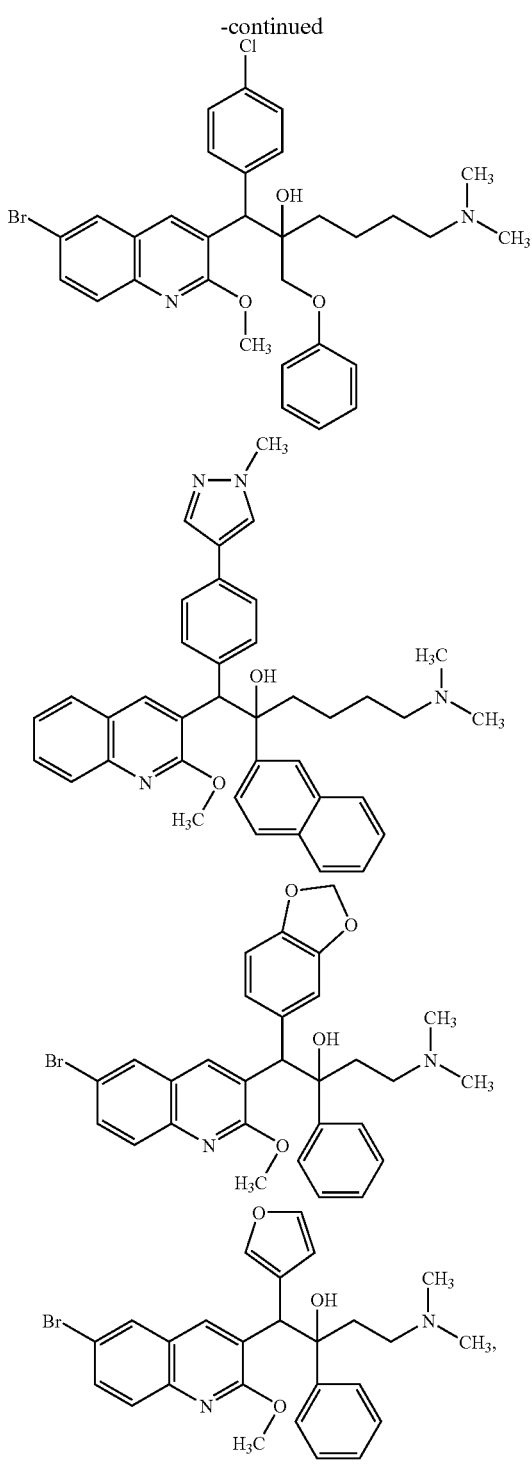

including any stereochemically isomeric form thereof,
a N-oxide thereof or a pharmaceutically acceptable salt thereof.

21. A method of treating a patient with a bacterial infection comprising administering to said patient a therapeutic amount of a compound according to claim 1.

22. A pharmaceutical composition comprising a pharmaceutically acceptable carrier and, as active ingredient, a therapeutically effective amount of a compound as defined in claim 1.

23. A method according to claim 21 wherein the bacterial infection is an infection with a gram-positive bacterium.

24. A method according to claim 23 wherein the gram-positive bacterium is *Streptococcus pneumoniae*.

25. A method according to claim 23 wherein the gram-positive bacterium is *Staphylococcus aureus*.

26. A process to prepare a compound according to claim 1 characterized by
a) reacting an intermediate of formula (IIa) or (IIb) with an intermediate of formula (III) according to the following reaction scheme

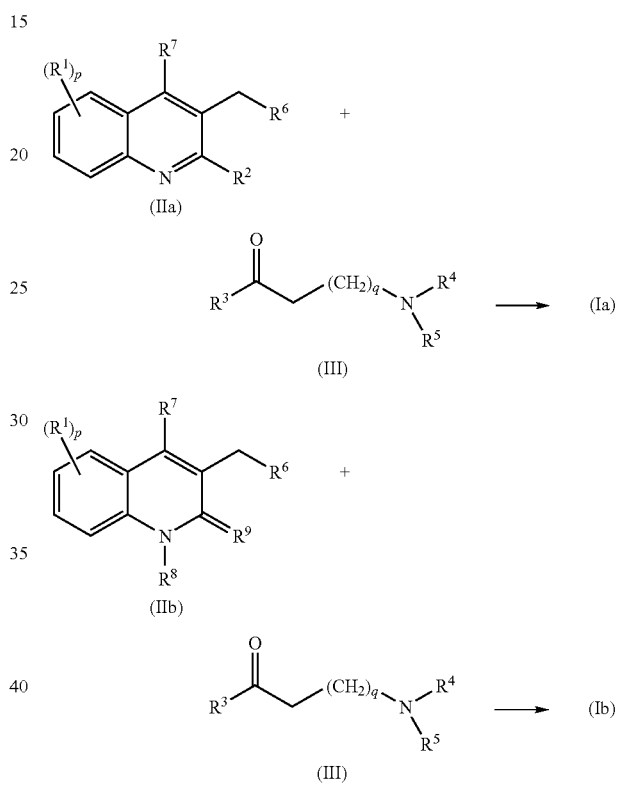

using nBuLi in a mixture of a suitable base and a suitable solvent, wherein all variables are defined as in claim 1, b) reacting an intermediate of formula (IV-a) or (IV-b) wherein $W^1$ represents a suitable leaving group, with Het-B(OH)$_2$ in the presence of a suitable catalyst, a suitable base, and a suitable solvent, according to the following reaction scheme

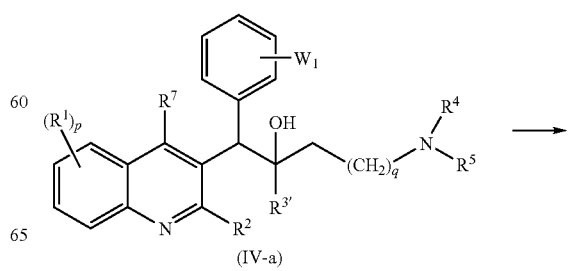

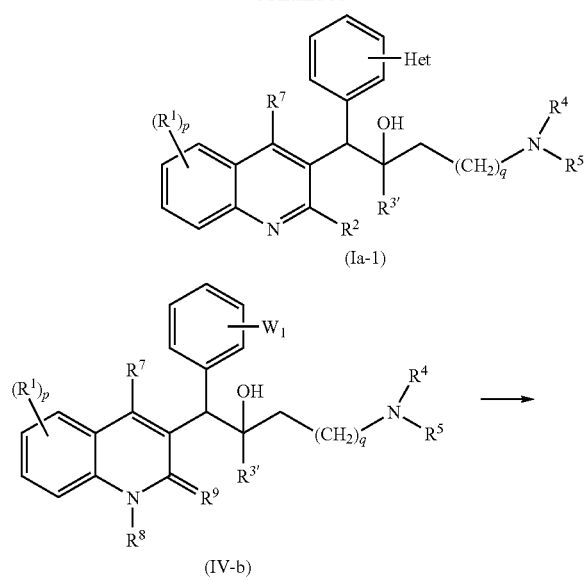

wherein all variables are defined as in claim 1 and wherein R³′ represents alkyl, arylalkyl, aryl, Het, Het-alkyl;

c) reacting an intermediate of formula (V-a) or (V-b) wherein q' is 0, 1 or 2, with a primary or secondary amine HNR⁴R⁵ in the presence of a suitable catalyst, optionally in the presence of a second catalyst (for the reduction), in the presence of a suitable ligand, in a suitable solvent, in the presence of CO and H₂ (under pressure),

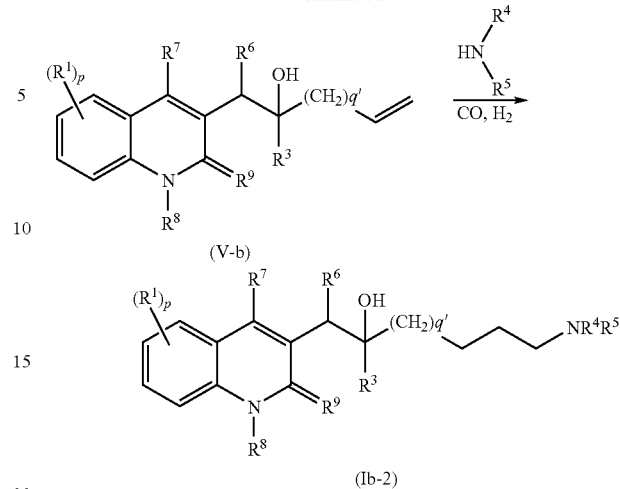

wherein all variables are defined as in claim 1;

d) reacting an intermediate of formula (VI-a) or (VI-b) wherein W₂ represents a suitable leaving group, with a suitable primary or secondary amine HNR⁴R⁵, optionally in the presence of a suitable solvent

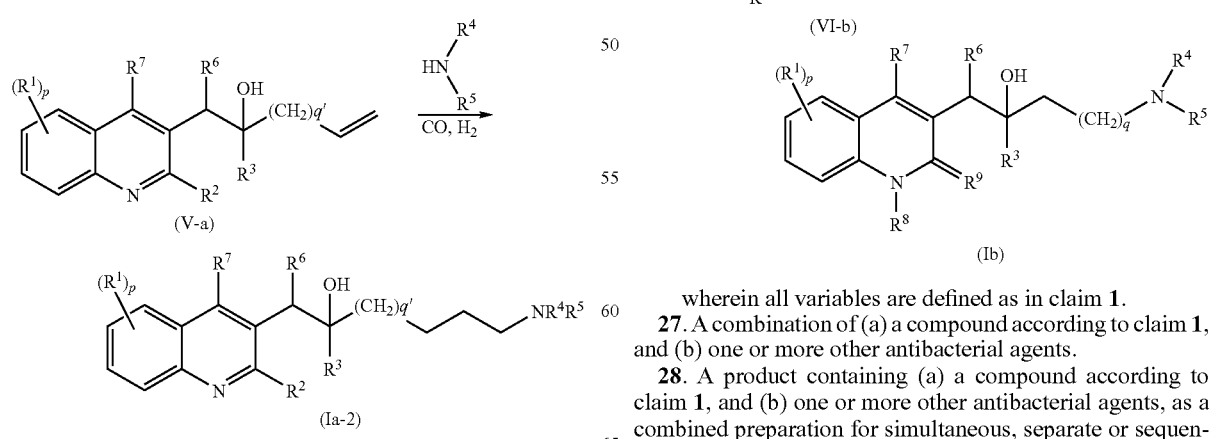

wherein all variables are defined as in claim 1.

27. A combination of (a) a compound according to claim 1, and (b) one or more other antibacterial agents.

28. A product containing (a) a compound according to claim 1, and (b) one or more other antibacterial agents, as a combined preparation for simultaneous, separate or sequential use in the treatment of a bacterial infection.

* * * * *